(12) United States Patent
Pogson et al.

(10) Patent No.: US 8,637,735 B2
(45) Date of Patent: Jan. 28, 2014

(54) METHOD FOR IMPROVING STRESS RESISTANCE IN PLANTS AND MATERIALS THEREFOR

(75) Inventors: Barry James Pogson, Aranda (AU); Philippa Bronwyn Wilson, Lyneham (AU); Jan Bart Rossel, Ngunnawal (AU)

(73) Assignee: The Australian National University, Acton (AU)

( * ) Notice: Subject to any disclaimer, the term of this patent is extended or adjusted under 35 U.S.C. 154(b) by 477 days.

(21) Appl. No.: 12/664,868

(22) PCT Filed: Jun. 19, 2008

(86) PCT No.: PCT/AU2008/000895
§ 371 (c)(1),
(2), (4) Date: May 24, 2010

(87) PCT Pub. No.: WO2008/154695
PCT Pub. Date: Dec. 24, 2008

(65) Prior Publication Data
US 2010/0257633 A1    Oct. 7, 2010

(30) Foreign Application Priority Data

Jun. 20, 2007 (AU) .................................. 2007903309
Mar. 26, 2008 (AU) .................................. 2008901466

(51) Int. Cl.
*C12N 15/82* (2006.01)
*A01H 9/00* (2006.01)
*A01H 5/00* (2006.01)

(52) U.S. Cl.
USPC ........... 800/285; 800/278; 800/295; 800/298; 800/306; 800/317; 800/320; 800/276; 800/286

(58) Field of Classification Search
None
See application file for complete search history.

(56) References Cited

FOREIGN PATENT DOCUMENTS

WO    WO-02/16655    2/2002

OTHER PUBLICATIONS

Xiong et al. (The Plant Journal, 40:536-545; 2004).*
Rossel et al, Plant, Cell and Environment, 29:269-281, 2006.*
Gil-Mascarell et al, The Plant Journal, 17(4)373-383, 1999.*
Atkinson et al, The interaction of plant biotic and abiotic stresses: from genes to the field, Journal of Experimental Botany, 2012.*
Arabidopsis.org, Germplasm: SALK_020882, pp. 1-2, 2003.*
Alonso et al Genome-Wide Insertional Mutagenesis of *Arabidopsis thaliana*, Science, 301: 653-657, 2003.*
Xiong et al 2001 Genes Dev, 15:1971-1984, 2001.*
Lee et al The Plant Journal, 17:301-308, 1999.*
Xiong, L., et al. A single amino acid substitution in the *Arabidopsis* FIERY1/HOS2 protein confers cold signaling specificity and lithium tolerance. The Plant Journal, 2004, vol. 40, No. 4, pp. 536-545.
Xiong, L. et al. FIERY1 encoding an inositol polyphosphate 1-phosphatase is a negative regulator of abscisic acid and stress signaling in *Arabidopsis*. Genes & Development, 2001, vol. 15, No. 15, pp. 1971-1984.
Tondelli, A. et al. Mappping regulatory genes as candidates for cold and drought stress tolerance in barley. Theoretical and applied genetics, 2006, vol. 112, No. 3, pp. 445-454.
Viswanathan, C. et al. Molecular genetic analysis of cold-regulated gene transcription. Philosophical transactions of the Royal Society of London, Series B, Biological Sciences, 2002, vol. 357, No. 1423, pp. 877-886.
Hunt, L. et al, ABA signaling: A messenger's FIERY fate. Current Biology, 2001, vol. 11, No. 23, pp. R968-R970.
Lee, H. et al. Cold-regulated expression and freezing tolerance in an *Arabidopsis thaliana* mutant. The Plant Journal, 1999, vol. 17, No. 3, pp. 301-308.
Quintero, F.J. et al. The SAL1 Gene of *Arabidopsis*, Encoding an Enzyme with 3'(2'), 5'-Bisphophate Nucleotidase and Inositol Polyphosphate 1-Phosphatase Activities, Increases Salt Tolerance in Yeast. The Plant Cell, 1996, vol. 8, No. 3, pp. 529-537.

* cited by examiner

*Primary Examiner* — Cathy Kingdon Worley
*Assistant Examiner* — Stephen Uyeno
(74) *Attorney, Agent, or Firm* — Edwards Wildman Palmer LLP; Jeffrey D. Hsi

(57) ABSTRACT

The present invention provides a method for obtaining a plant with increased stress resistance relative to a wild-type plant, comprising: (a) introducing at least one mutation or exogenous nucleic acid into the genome of one or more plant cells which results in reduced activity associated with SAL1 or a homologue thereof in said one or more plant cells; (b) regenerating one or more plants from said one or more plant cells; and (c) selecting one or more plants that have increased stress resistance relative to a wild-type plant.

10 Claims, 31 Drawing Sheets

Col-0 wild type
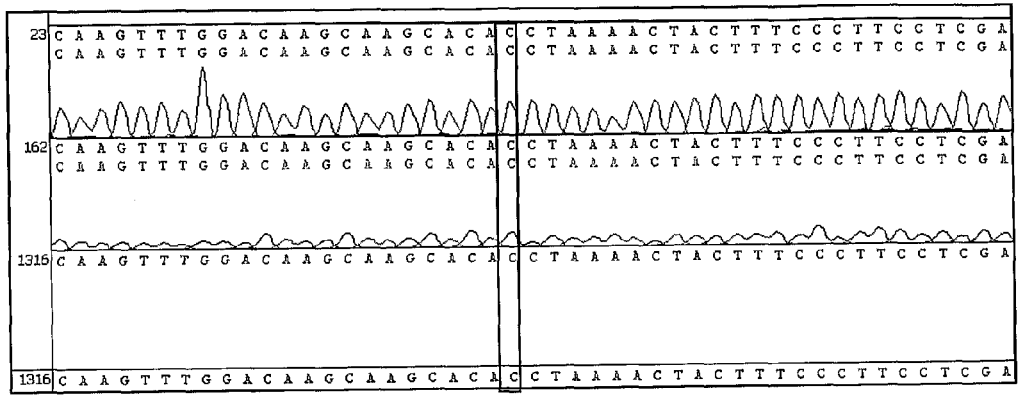
alx8 – original line (M6 pool)
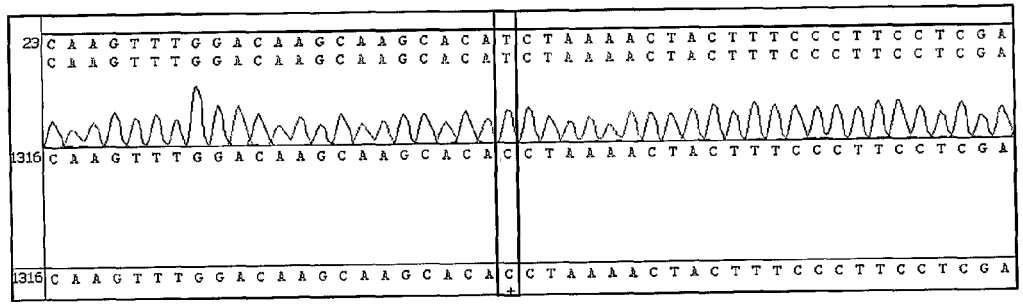
alx8 – 1ʳˢᵗ backcross
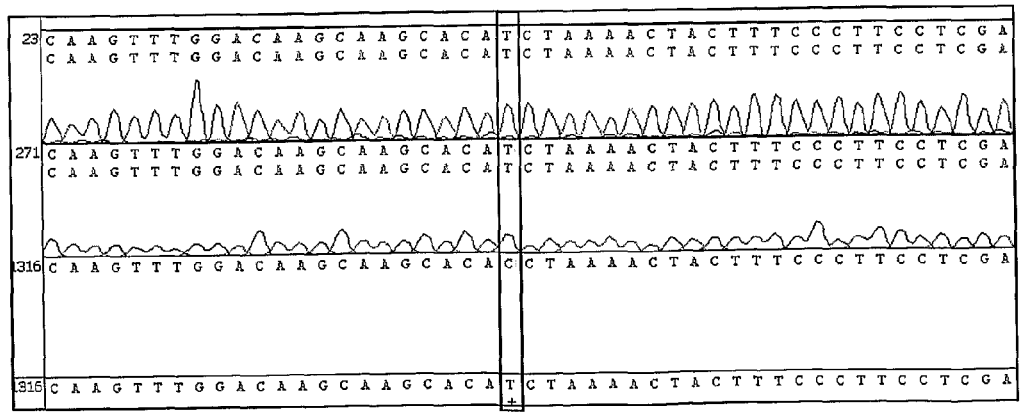
Fig. 1A

*alx8* – 3$^{rd}$ backcross with dCAPS (a->g)
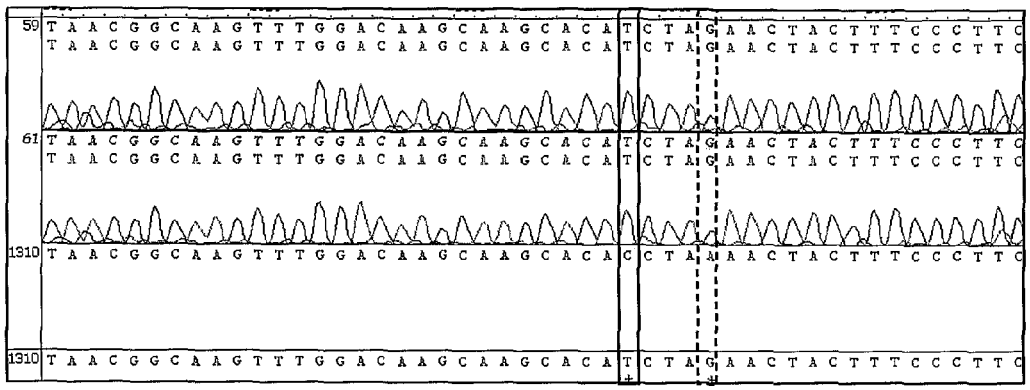
*alx8* – 4$^{th}$ backcross with dCAPS (a->g)
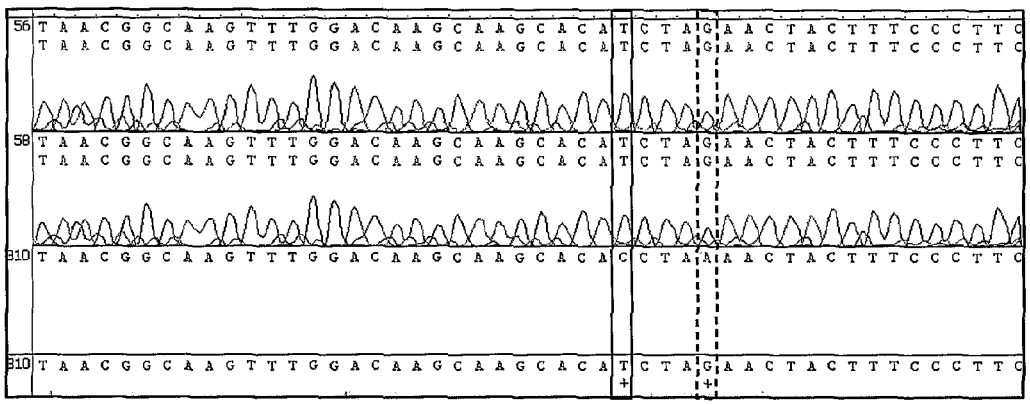
Col-0 WT with APX2-LUC
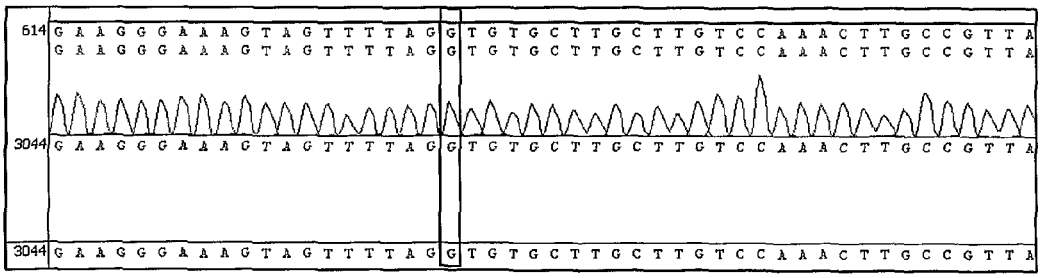
Fig. 1A (cont$^d$)

Figure 3 – Genomic Nucleotide Sequence of SAL1 – SEQ ID NO:1

```
1     gacatatatt tatcttcttg aaaagcgaat gatgtctata aattgttttc gaacagcgaa
61    ggctccgctt caatcatttg tagcagtaag aacgaattcg agacctagaa attcatcgaa
121   ccgtctcgtt tctgtattcg gacgcaagtc ttcttctcct tcatttgtta ctctcagagt
181   tgtttcatcg atggcttacg agaaagagct tgatgctgct aagaaagctg cttcactcgc
241   tgctcgtctc tgtcaggtta gggtttttttc gattcaatca tgacccatag attctaaagt
301   ttgattcttt aagaaaccca ttttgtaaat cttccaaatt tcgtttaaca ttttgtgttt
361   attgtgcatt gcatctgtaa ttgggaatag attctagtga tatagtgtaa tggtcctcta
421   catacgaagc tcgtgtaaat ctttgatcaa aatcttatct ttgtgttttg ggtttgtttc
481   agaaagttca aaaggctttg ttgcaatcag atgtgcaatc aaaatctgat aaaagtccag
541   tgaccgttgc tgattatggt tagtttgtta tacctgtccc tgattagaaa aagctcttct
601   ctttgaatgt tactgagatt gttaggaaat cacttaattt gatctgtctt gtgttgaatt
661   tcaggttcac aagcagttgt tagtttagtc ttagaaaaag agctcagttc tgaacccttt
721   tcattggtgg ctgaagaggt gaaactgctt aataaatcct tgttagatgt ctcacacttt
781   acttatcttt gagtttgtgt ttatggactc acattgtcta aatgatcta tataggactc
841   aggcgatcta cgcaaggatg gttctcagga tactctggag cgcatcacaa aactcgtgaa
901   cgacactttg gctaccgagg aatcgtttaa tggctctact ttgtctactg atgatctact
961   tagagccatt gactgtggaa catctgaagg tggtccaaat ggtcgacact gggtcttgga
1021  tccaattgat ggcactaaag ggtacgtttt aaaactaact agcctaaagt caaatcttct
1081  tatttcagag aaaatgtaaa tttgatagaa tgttgagtca gatgttatgt tcctgacact
1141  gagcattttc atgattttag atttctgagg ggagatcaat acgcagtagc actaggattg
1201  ctcgaggaag ggaaagtagt tttaggtgtg cttgcttgtc caaacttgcc gttagcatcc
1261  atagcaggaa acaacaagaa caaatcttcg tcagacgaaa ttggatgcct cttctttgct
1321  acaattggtt cagggacata tatgcagctc ctagattcaa aatcttctcc tgtaaaagtg
1381  caagtctcta gtgttgagaa tcctgaagag gcatcgttct tcgagtcatt cgaaggagct
1441  cactctctac atgacttatc cagctccatt gccaatgtaa attgcttctt tccttccatg
1501  tgattccagc taatagctaa ctaattttcc tcatccattt gatcatgttc tatgttgtaa
1561  tatacagaaa ctcggtgtca aagctccacc agtccgtatt gatagccaag caaagtatgg
```

Fig. 3

```
1621  agctttatca agaggagatg gagctatata cttacggttt cctcataaag gataccgcga
1681  aaagatttgg gaccatgtcg ctggtgctat agttgttaca ggtaacatta aagcttactc
1741  tctatgaagc taatttata  gtgtcgacat gcggatgtaa atagataagg aatgcaaggt
1801  tgattcttct ttttggtgca gaggcgggtg gaatagtgac agatgcagca ggaaagccac
1861  tggatttctc gaaagggaag tatcttgatt tggacacagg cattatcgtt gctaacgaga
1921  agctaatgcc tctgcttttg aaagcagttc gtgactccat agctgagcaa gagaaagctt
1981  cagctctctg atttgttttt ttctctcgta cgttctttgt ttctctgtaa ctgttgtttc
2041  attttctttc accgaatttc accagtgaga atttcttcca ttttcgaaaa agaaataaaa
2101  atgaaattct gttttgggct aa
```

Fig. 3 (cont$^d$)

Figure 4 – Amino Acid Sequence of SAL1 – SEQ ID NO:2

```
1    MMSINCFRTA KAPLQSFVAV RTNSRPRNSS NRLVSVFGRK SSSPSFVTLR
51   VVSSMAYEKE LDAAKKAASL AARLCQKVQK ALLQSDVQSK SDKSPVTVAD
101  YGSQAVVSLV LEKELSSEPF SLVAEEDSGD LRKDGSQDTL ERITKLVNDT
151  LATEESFNGS TLSTDDLLRA IDCGTSEGGP NGRHWVLDPI DGTKGFLRGD
201  QYAVALGLLE EGKVVLGVLA CPNLPLASIA GNNKNKSSSD EIGCLFFATI
                       D
251  GSGTYMQLLD SKSSPVKVQV SSVENPEEAS FFESFEGAHS LHDLSSSIAN
301  KLGVKAPPVR IDSQAKYGAL SRGDGAIYLR FPHKGYREKI WDHVAGAIVV
351  TEAGGIVTDA AGKPLDFSKG KYLDLDTGII VANEKLMPLL LKAVRDSIAE
401  QEKASAL*
```

Fig. 4

```
CLUSTAL W (1.83) multiple sequence alignment rice            MSQAAGNPYAAELAAAKKAVTLAARLCQAVQKDILQSGVQSKADQSPVTVADYGSQILVS 60
maize           --MASGNPYAAELAAAKKAVTLAAKLCQTVQQDIMHSGVQAKADKSPVTVADYGSQILVG 58
Arabidopsis     ------MAYEKELDAAKKAASLAARLCQKVQKALLQSDVQSKSDKSPVTVADYGSQAVVS 54
                    .*  ** *****.:***;***  **:   :::*.**:*;*;***********  :*.

rice            LVLKMEAPASSSFSMVAEEDSEELRKEGAEEILENITELVNETIVDDGTYS-IYFSKEGI 119
maize           FSLRMDV-SSGPFSLVAEEALDELRKDGAEEILEDITDLVNETIFDDGSYN-ISFTKEGI 116
Arabidopsis     LVLEKEL-SSEPFSLVAEEDSGDLRKDGSQDTLERITKLVNDTLATEESFNGSTLSTDDL 113
                : *: :  :* .**;****   :***;*;:: ** **.***;*:  : ::.   ::.:..:

rice            LSAIDDGKSEGGPSGRHWVLDPIDGTKGFLRGDQYAIALALLDEGKVVLGVLACPNLSLG 179
maize           LSAIDDGKSEGGPSGRHWVLDPIDGTKGFLRGDQYAIALALLDEGKVVLGVLACPNLPLS 176
Arabidopsis     LRAIDCGTSEGGPNGRHWVLDPIDGTKGFLRGDQYAVALGLLEEGKVVLGVLACPNLPLA 173
                * *** *.*****.***************************:**.** ;************.*.

rice            SIGNLNGG-SSGDQVGALFSATIGCGAEVESLQG-SPAQKISVCSIDNPVEASFFESYEG 237
maize           SINNINGN-SSGDKVGALFSATIGCGAQVESLDG-SPPQKISVCSIDNPVNASFFESYES 234
Arabidopsis     SIAGNNKNKSSSDEIGCLFFATIGSGTYMQLLDSKSSPVKVQVSSVENPEEASFFESFEG 233
                **  . *  . **.*;:*.** ****.*:  :: *:. *.. *:.*.*:;;** ;*****:*.

rice            AHSLRDLTGSIAEKLGVQAPPVRIDSQAKYGALARGDGAIYLRFPHKGYREKIWDHAAGS 297
maize           AHSMHDLTRSIAEKLGVQAPPVRIDSQAKYGALARGDGAIYLRFPHKGYREKIWDHAGGS 294
Arabidopsis     AHSLHDLSSSIANKLGVKAPPVRIDSQAKYGALSRGDGAIYLRFPHKGYREKIWDHVAGA 293
                ***:;**: ***;****:**************;*****************..*:

rice            IVVTEAGGLVTDASGNDLDFSKGRFLDLDTGIIATNKQLMPSLLKAVQDAIKEQNQAASP 357
maize           IVVTEAGGIVTDAAGKDLDFSKGRFLDLDTGIIATNKELMPSLLKAVQEAIKETNQAASL 354
Arabidopsis     IVVTEAGGIVTDAAGKPLDFSKGKYLDLDTGIIVANEKLMPLLLKAVRDSIAEQEKASAL 353
                ********;****;*: ******;:*********.:*;;*** *****:::* * ::*;:

rice            L 358
maize           L 355
Arabidopsis     -
```

Fig. 5

| Species | EST ID | Identity (%) |
|---|---|---|
| *Hordeum vulgare* (Barley) | TC141977 | 64% & 62% |
| *Triticum aestivum* (Wheat) | TC233967 | 68% & 68% |
| Oryza sativa (Rice) | TC298407 | 66% |
| Zea mays (Maize) | TC320492 | 69% & 67% |
| *Solanum tuberosum* (Potato) | TC136604 | 69% |
| *Picea* (Spruce) | TC17821 | 67% & 71% |
| *Pinus* (Pine) | TC67647 | 65% |
| *Allium cepa* (onion) | TC448 | 72% |
| *Lycopersicon esculentum* (Tomato) | TC176257 | 73% |
| *Glycine Max* (Soybean) | TC216235 | 74% |
| *Medicago truncatula* | TC95084 | 73% |
| *Gossypium hirsutum* (Cotton) | TC28214 | 74% & 77% |
| Populus (Poplar) | TC45863 | 75% |
| *Brassica napus* (Oilseed rape) | TC9828 | 88% |
| *Lotus japonicus* | TC13858 | 74% |

Fig. 6A

CLUSTAL W (1.83) multiple sequence alignment

```
Spruce     ------------------------GGTTCTCTGCGACTTGTGTGTATAAGTCTATAACAT 36
Pine       ------------------------------------------------------------
Medicago   ----------------TGGGGACGCAGAGTTTGTT---GGGAGGAACAAGAACGGTAGTA 41
Lotus      ------------------------------------------------------------
Soybean    --GAAAAAGATGGGTACTCAAACAACACTTTGGTGTAGAGCAAGAACTACTATAAGTGTA 58
SAL1       ---------------------------------GACATATATTTATCTTCTTGAAA 23
Oilseed    ------------------------------------------------------------
Poplar     ------------------------------------------------------------
Cotton     ------------------------------------------------------------
tomato     ------------------------------------------------------------
Potato     ------------------------------------------------------------
onion      ---------------------------------------------CAATTTGCAAAAGTC 15
Wheat      CTCGTGCCGAATTCGGCACGAGGCGCGTGGGCCTCCTCCTCGCTCCCTCCTCCCTCGCCC 60
barley     ------------------------------------------------------------
rice       ----------------------------------------------GTGGAATTCCGGTC 14
maize      -----------------------------CGCACATGGCTGCGCGCGTGGGCCTGCTCCC 31

Spruce     CAATCAATGGCGTGGTCGAGCCGATTCTCATTTCAATTTACGAGGACTTCTAGTGCCACC 96
Pine       ------------------------------------------------------------
Medicago   GCAATAAGGGATTGTTGCGAATCCATAAATACAATAATAATAATCAGGAAAAAATCCACC 101
Lotus      ----------------------------------------AGAATCTGGAAAACAACCATC 21
Soybean    GGAG----GTGATTGGAAGTTG--TTCGAATCC------AGAATCCGAAAAAGGGCACC 106
SAL1       AGCGAATGATGTCTATAAATTGTTTTCGAACAGCGAAGGCTCCGCTTCAATCATTTGTAG 83
Oilseed    -------------------------GGAACAGCCCAGGCACCGCTTCAGACATTCGCAT 34
Poplar     --------------------------------------------------GCGAAATC 8
Cotton     -----------GGAATTTTCTTACGAAATTTTTGAATTGCAAATTTAATAAATGTCTAT 48
tomato     ------------------------------------------------------------
Potato     ----------------------GCTTTCACATTATCATCTAGGACTATAAATTCCTTG 36
onion      CCTCCTCGTCTACACTGTGCTAACCTATCCCCCTTAATCTCGATTAAATGTTCCCCAATT 75
Wheat      GAAACCCACCTCGTGCTCGCCTCCCTTATCCCCTGCCTTCCCACCACCTTGGCCGCCCCA 120
barley     ----------------------------------------CAAANAATCCTCACTA 16
rice       GCGCCGTGCATCTCGTACGTGACGGGGAGGGGCGGCCTCAC--CCAGGGATGCTGCAACG 72
maize      GCACGCGATCCTCGTCTCCTCCCGAGCTCTACCCACGCCCCGAGCTCGCGTCCCTTATCC 91

Spruce     TCATTTGTTTTCCTTCCAACTACAA-CCCTACCTCTACAGATACATTTCCCCAGCGTGAG 155
Pine       ------------------------------------------------------------
Medicago   ACCGTCTCTGGTTTCTCATTATCAT-CATCAACGACA-AGAAGATCCTCTTCATTGTATT 159
Lotus      ACCNGTTGTGATCTTTCAT---CAA-GGGGAAGAAGA-AGAAGACCAGTTTCCTTGTCTT 76
Soybean    ACCG--------TGTCAA---CAA-GTAGAAGCAGA-AGCTGTTTTTGTTCTTCGC--C 150
SAL1       CAGTAAGAACGAATTCGAGACCTAGAAATTCATCGAACCGTCTCGTTTCTGTATTCGGAC 143
Oilseed    CAGT--------TTCGAAATTCAGATATTCACCGAACCCTATCGTTTCTGTATTGAAGA 76
Poplar     ACAATCACGAAAAACCCTTTTCTTG-TTTCCTC------TCCCCTTTTATTTTTCTCTAA 61
Cotton     AAATTGGTTGAGATTTGTTTCCCCC-TCTCTTAAAAA-GCCCCCTCTTTTTCATCTCTGT 106
tomato     --------------------------AAAATACA-AAACCCCACTTCCCCTTTTCAC 30
Potato     ACACAAAAAACCCTGCCATTGTTAA-CAAAAAATACA-AAACCCCATTTCCCCTTTTCAC 94
onion      AATTATCTCCCTGTCTTTTCTCCCA-CCAAATCTAGT-TCACTTTCTTGCTCCTCCGTAT 133
Wheat      CCTACCGCCGATTCGCCTCCTCCGCGCCGCTGCGCTCCCCCTCTGGTGGCCCCGCCAAG 180
barley     G--AAGGGAAAGACAAAGTTGCAGCGTCAGCGCGA-CCTGCCCGTGCCCGCCCCACCTAC 73
rice       GCGTCAAGGGGCTGAACAACGCCGC-CCGCACCACCGCCGACCGCCAGGCCGCCTGCCGC 131
maize      TCTTCCACCCGTCCCTTCCTACCTC--CGCCACGCCTCCTCCTCCGCCTCCCGCTCCTGC 149
```

Fig. 6B

```
Spruce     TGCGAGGAGGAGCATCACCACCAAGACAACAAGAGCGAAAATGGACATCGGTG-CATACG 214
Pine       ------------------------------CAAGAGTGAAGATGGAGAACAGGG-CATACG  30
Medicago   GTCGTCGTTGGTCACCATTAACGACAATACTTTCTTCTTCTTCTTTAATGTCTTCTTACG 219
Lotus      GTTGTTGTTCATCACT-------------------------TTCTTCAATGCCT---TACG 109
Soybean    GCTGACACTAATCGT--------------------------TTCTTCAATGCCT---TACG 182
SAL1       GCAAGTCTTCTTCTCCTTCATTTGTTACTCTCAGAGTTGTTTCATCGATGGCT---TACG 200
Oilseed    GGAAGTC---GTCTCCTTCATTTGTTACTCTAAGAGTAGTCTCATCCATGGCT---TACG 139
Poplar     CAAAACCAAAAGCAAAACC-TCAATTCCAAGAGTATTATCCTCTTCAATGTCT---TACA 117
Cotton     CACTTGCCTCCTCCTCCTC-CTTCTTCTTCTGCTGTGATTGTGG-CAATGTCT---TATG 161
tomato     TTTTGCTCACTCTAAGAGCATCTAAATCAACCTTAAGAGCTGTTACAATGTCG---TATG  87
Potato     TTTGTCTCACTCTAAGAGCATCTAAATCAACCTTAAGAGCTGTTTCAATGTCG---TATG 151
onion      CTCAATTAAAAGCCAAGACTGAATCTAGATCTTTATCCATTTCTGCCATGGCTTCGTACG 193
Wheat      CGCCACC--CCTCTTTTCCGCCCGCGCCATGTCAGGGTCCGCCGGTAGCCCCC-CGTACG 237
barley     CGCCGCCGGCCGCCCAATCGATTG-GCAATGTCGCGGCCCGCCGGCAATCCCC-CGTACG 131
rice       TGCCGCGAGACTCCGCGCCAGCGCCACCATGTCGCAGGCCGCCGGGAACCCC----TACG 187
maize      CGCGCGTCGCCGCGTTTTGTCGCAGTCCGCGCCATGG-CTTCGGGGAACCCC----TACG 204
                                                                   **

Spruce     AACAAGATCTTGCCATTGCAATCAAGGCCGCCTCTCTCGCAGCTCGTCTATGCCAGTCGG 274
Pine       AACAAGATCTTGCCATTGCAATCAGGGCTGCCTCTCTGGCAGCTCGTCTATGCCAGTCAG  90
Medicago   AGAAGGAACTCGCTGCTGCTAAGAAAGCTGCCACTCTCGCTGCTCGTCTTTGCCAGAAAG 279
Lotus      AGAAGGAGCTCGCTGCTGCCAAGAAAGCAGCCACTCTCGCTGCTCGTCTCTGTCAGAAAG 169
Soybean    AGAAGGAATTCGCCGCTGCAAAAAAAGCAGCCACTCTCGCTGCTCGTCTCTGCAAGAAAG 242
SAL1       AGAAAGAGCTTGATGCTGCTAAGAAAGCTGCTTCACTCGCTGCTCGTCTCTGTCAGAAAG 260
Oilseed    AGAAAGAGCTTGACGCTGCTAAGAAAGCTGCTTCCCTCACAGCTCGTCTCTGTCAGAAAG 199
Poplar     ATAAAGAACTTGCTGCTGCCAAGAAAGCTGTCTCTCTTGCTGCCCGCCTCTGCCAGAAGA 177
Cotton     ATAAAGAACTGGCTGCTGCAAAGAAAGCAGCCTCTCTCGCTGCTCGTCTCTGTCAGAAAG 221
tomato     ATAAAGAACTTGATGCTGCCAAGAATGCTGCTTCTCTTGCTGCTCGCCTTTGTCAAAAAG 147
Potato     ATAAAGAACTTGATGCTGCCAAGAATGCTGCTTCTCTTGCTGCTCGCCTCTGTCAAAAAG 211
onion      AGAAAGATCTTACCGCTGCCAAGAAGGCTGCTTCACTGGCTGCTCGTCTATGCCAAACGG 253
Wheat      CCGCCGAGCTTGCAGCCGCCAAGAAGGCCGTCGCCCTTGCCGCCCGCCTATGCCAGACTG 297
barley     CCGTCGAGCTCGGCGCCGCGAAGAAGGCCGTCTCCCTCGCCGCCCGCCTATGCCAGACGG 191
rice       CCGCTGAGCTCGCCGCCGCCAAGAAGGCCGTCACCCTCGCCGCCCGCCTCTGCCAGGCGG 247
maize      CCGCCGAGCTCGCCGCCGCCAAGAAGGCCGTCACCCTCGCCGCCAAACTCTGCCAGACAG 264
             **    *        ** *   *   ** *    * **    * **    ** **   *

Spruce     TGCAAAAGAGCCTTTTACAAACAGATACTCAAGCCAAGATGGACAGTTCTCCTGTCACTG 334
Pine       TGCAGAAGAGCCTTTTACAAACAGATACTCAAGCCAAGACGGACAGTTCTCCTGTCACTG 150
Medicago   TACAAAAAGCTCTTCTTCAATCTGATGTTCACTCTAAATCTGACAAAACTCCTGTCACTG 339
Lotus      TACAAAAGGCTCTTCTGCAATCCGATGTCCACTCAAAATCAGACAAAAGTCCTGTCACCG 229
Soybean    TACAGAAGGCTCTTCTGCAATCCGATGTGCACTCAAAGTCAGACAAAAGTCCTGTCACAG 302
SAL1       TTCAAAAGCTTTGTTGCAATCAGATGTGCAATCAAAATCTGATAAAAGTCCAGTGACCG 320
Oilseed    TTCAAAAGGCTTTGTTGCAATCAGATGTTCAATCAAAATCTGATAAAAGTCCAGTCACCG 259
Poplar     TGCAAAAAGCTATCTTGCAATCAGATGTCCAATCAAAATCAGATAAAAGTCCCGTCACTG 237
Cotton     TACAAAATGCTTTGCTGCAATCCGATGTTCAATCAAAGAATGATAAAAGTCCTGTAACTG 281
tomato     TCCAAAAAGCACTGTTGCAAGCAGATGTTCAATCAAAGTCTGACAAATCTCCAGTGACGG 207
Potato     TCCAAAAAGCACTGTTGCAAGCAGATGTTCAATCAAAGTCTGACAAATCTCCTGTGACGG 271
onion      TGCAGAAGGCGATATTGCAGTCGGATGTGCACTCAAAAGCAGATAAGACTCCTGTTACTG 313
Wheat      TACAACAGGAAATTCTGCAATCAGATATTCAGTCCAAGGCAGATAAAAGTCCTGTGACAG 357
barley     TGCAGCAGGAAATCGTGCAGTCAGACATTCAATCTAAGGCGGATAAGACTCCTGTCACCG 251
rice       TGCAAAAGGACATTCTGCAGTCTGGTGTTCAGTCTAAGGCGGATCAAAGTCCGGTGACAG 307
maize      TTCAACAGGATATTATGCATTCTGGCGTTCAGGCTAAGGCAGACAAAAGTCCTGTCACAG 324
            *  **   *        *   *  **   *      **   * **      *** ** ** *
```

Fig. 6B (cont$^d$)

```
Spruce      TTGCGGATTATGGTTCTCAGGCTTTAGTTAGCTTTGTGCTTGAGAGGGAACTA---CAAT 391
Pine        TTGCAGATTACGGTTCTCAGGCTTTAGTTAGCTTTGTACTTGAAAGGGAATTA---CCCT 207
Medicago    TTGCTGATTATGGTTCGCAGATCTTGGTCAGCTTGATGCTTCAGAGAGAGCTT---CCTT 396
Lotus       TCGCTGATTATGGTTCACAAACCTTGGTCAGCTTAATACTCGAGAGAGAACTT---CCTT 286
Soybean     TGGCTGATTATGGTTCACAAGCATTGGTCAGCTTTATACTTGAGAGAGAACTT---CCTT 359
SAL1        TTGCTGATTATGGTTCACAAGCAGTTGTTAGTTTAGTCTTAGAAAAAGAGCTC---AGTT 377
Oilseed     TTGCTGATTATGGTTCACAAGCAGTTGTCAGCATAGTCTTGGAAAGGGAACTC---ACTT 316
Poplar      TTGCTGATTATGGCTCTCAAGCACTAGTTAGTTATGCTCTGCAGCGGGAGCTT---CCTT 294
Cotton      TTGCTGATTATGGCTCACAAGCACTGGTTAGTTTTGTGCTGCAGCAGGAATTT---CCTG 338
tomato      TGGCTGATTATGGCTCACAGGCCGTGGTTAGCGTTGTTTTGCAGAAAGAGTTG---TGTT 264
Potato      TGGCTGATTATGGCTCACAGGCCGTGGTTAGCGTTGTTTTGCAGAAAGAGTTG---GGTT 328
onion       TGGCCGATTATGGTTCCCAAGTATTGGTCAGTCTTGTTTTGAGAAAAGAACTT---CCTT 370
Wheat       TAGCTGACTATGGATCTCAAGTATTGGTAAGCCTTGCGTTAAATATGGAAGTA---ACTT 414
barley      TAGCTGATTATGGATCTCAGGTATTGGTGAGTCTTGTGTTAAATATGGAAGTA---ACCT 308
rice        TTGCCGATTATGGGTCTCAAATATTGGTAAGCCTTGTCTTGAAAATGGAAGCACCAGCTT 367
maize       TGGCTGATTATGGATCTCAAATATTGGTCGGTTTTTCCTTAAAGATGGATGTA---TCAT 381
            * ** ** ** ** ** **     * **  *         *      **

Spruce      CGGGAGTGTTTTCCATGGTTGCAGAAGAGGATTCAGGAGATTTACAGAAGAATGATGCAC 451
Pine        CGGGATTGTTTTCCTTGGTTGCAGAAGAGGATTCAGGAGATTTACAGAAGAATGATGCAC 267
Medicago    CTGAACCATTTTCATTAGTAGCTGAGGAGGATTCAGGGGATCTTCGTAAGGAAAGTGGCC 456
Lotus       CTGAACCATTTTCATTAGTAGCTGAGGAGGATTCAGGCGATCTGCGTGAGGAAAGTGGCC 346
Soybean     CTGAACCATTTTCATTAGTAGCTGAGGACGATTCAGGTGATCTTCGTAAGGAGAGTGGTC 419
SAL1        CTGAACCCTTTTCATTGGTGGCTGAAGAGGACTCAGGCGATCTACGCAAGGATGGTTCTC 437
Oilseed     CTGAACCCTTTTCATTGGTCGCTGAAGAGGACTCAGCGGATCTACGCAAGGATGGTTCTG 376
Poplar      CTGAACTATTCTCCTTAGTGGCGGAGGAGGATTCAGAAGATCTCCTCAAGGATGGTGGCC 354
Cotton      ATAAC---TTCTCATTAGTTGCTGAGGAGGATTCTAAAGATCTTCGCAAGGATGGTGGCC 395
tomato      CTGCTTCATTTTCATTAGTGGCTGAGGAGGACTCTGGAGACCTTCGTAATGAAGAGGGAA 324
Potato      CTGCTTCATTTTCATTAGTGGCTGAGGAGGACTCTGGAGATCTTCGTAATGAAAAGGGAA 388
onion       TTGATTCCTTTTCAATGGTTGCTGAAGAGGATTCAGGAGACTTGCGAACAGATGCTGGTC 430
Wheat       CTGGTTCATTTTCTATGGTGGCCGAAGAGGACTCAGAAGACTTGAGAAAGGATAGCGCTG 474
barley      CTGGTTCCTTTTCTATGGTGGCCGAGGAGGATTCAGAAGACTTGAGAAAGGATGGCGCTG 368
rice        CTTCTTCCTTCTCTATGGTGGCTGAGGAGGACTCGGAAGAATTGAGGAAAGAAGGCGCAG 427
maize       CTGGACCATTTTCATTGGTGGCTGAAGAGGACTCAGATGAATTGAGAAAAGATGGCGCTG 441
                ** **    * ** ** ** ***** **    ** *         *

Spruce      AAGATATGGTGGAACGCATTACAGCACTTGTAAATGAAACCATTTCTAATGATAGTGCCT 511
Pine        AAGATATGGTGGAACGCATTACAGCACTTGTAAATGAAACCATTTCTAATGATGGTACCT 327
Medicago    AAGACATTGAAGCGCATTACAGATCTTGTCAATGATACTCTTGTTAATGAAGGATCAC 516
Lotus       ACGATACTTTGAAGCGGATTACAGAACTTGTCAATGATACTCTTGCTAATGAAGGATCAA 406
Soybean     AGGATACGCTGAAGCGCATTACAGAACTTGTCAATGATACCCTTGCTAGTGAAGGATCAA 479
SAL1        AGGATACTCTGGAGCGCATCACAAAACTCGTGAACGACACTTTGGCTACCGAGGAATCGT 497
Oilseed     AGGATATTCTTCAGCGCATCACGAAACTCGTCAACGACACTTTGGCTACTGAGGATCTAA 436
Poplar      AGGAAACACTAGAGCGAATCACAAAACTTGTTAACGATATTCTAGCTACCGATGGATCAT 414
Cotton      AGGAAATAGTAGAGCGCATTACAAAACTTGTGAACGATTCTCTAACTATTGATGGATCAT 455
tomato      AATCAACATTACAGCGTATCATGAAGCTTGTCAATGAAACACTTGCTAGTGATGGAACAT 384
Potato      AAGCAACATTACAGCGTATCATGAAGCTTGTCAATGAAACACTTGCTAGTGATGGAACAT 448
onion       AAGAAACATTGAAACGTATTACGAAGCTTGTAAATGACACTCTTTCTTCTGATAGTACTT 490
Wheat       AAGAAATTCTGGAACATATTACTGATCTTGTAAATGAAACTCTCGCTGAGGATGGTTCAT 534
barley      ACGAAATTCTGGAGCGCATTACTGATCTCGTAAACAAAACTCTCGCTGAGGATGGTTCAT 428
rice        AAGAAATTTTAGAAAATATCACCGAGCTCGTAAACGAAACTATCGTAGATGATGGTACAT 487
maize       AAGAAATTTTGGAAGATATTACTGACCTTGTCAATGAAACCATCTTTGATGATGGTTCAT 501
             *     *  *     ** *    ** ** **  *  *       **
```

Fig. 6B (cont<sup>d</sup>)

```
Spruce     ATAA------TATTTCTCCATTAACAACAGGAGATGTACTTGCAGCAATAGATAGAGGCA 565
Pine       ATGA------TATTTCTCCATTAACAACAGGAGATGTACTTGCAGCGATAGATAGAGGTA 381
Medicago   ATAA------CATTTCTGCTTTAACAACAGATGACGTGCTTAATGCCATTGATAATGGTA 570
Lotus      ATAG------CTTTTCTACTTTAACAACAGACAATGTGCTTAGAGCCATTGACAATGGTA 460
Soybean    ATAG------CTTTTCTACTTTAACAACAGATGATGTGCTTGCGGCCATTGACGGTGGTA 533
SAL1       TTAA------TGGCTCTACTTTGTCTACTGATGATCTACTTAGAGCCATTGACTGTGGAA 551
Oilseed    CCAAAGCCATTGACTCTACTTTAACCACAGATGATCTACTCAGAGCCATCGACTGTGGCA 496
Poplar     ATAG------TGATTCTACTTTTATCCACTGAAGTATTGTCAAGGCCATTGACTGTGGAA 468
Cotton     ACAA------TG---TTACTTTTACCACAGAAGATATTCTCAGGGCCATTGACAATGGCA 506
tomato     ATGG------TACTGCCCCATTATCTGAAGAAGATGTCCTTGCTGCCATTGATAGTGGTA 438
Potato     ATGG------TACTGCCCCATTATCTGAAGAAGATGTCCTTGCTGCCATTGATAGTGGTA 502
onion      ATAA------TGATATAATTTTATCTGAAGAAGATATACTTGTCGCTATTGATACTGGAA 544
Wheat      ACAA---------CATTACTTTATCTAAGGAAGGTATCCTCTCTGCAATTGATACTGGGA 585
barley     ACAA---------CATTTTATTATCTAAGGAAGCTATCCTCTCTGCACTTGATACCGGGA 479
rice       ACAG---------CATTTACTTCTCTAAGGAAGGTATCCTCTGCAATTGACGACGGCA 538
maize      ATAA---------CATTTCGTTTACAAAGGAAGGTATACTCTCTGCAATTGATGATGGGA 552
                        **  *      *    *   *     **  *  **     ** *

Spruce     AATCTGAAGGAGGGCCACATGGTCGGCACTGGGTTTTGGACCCCATTGATGGGACAAAAG 625
Pine       AATCTGAAGGAGGGCCCCATGGTCGGCATTGGGTTTTAGACCCCATTGATGGGACAAAGG 441
Medicago   AGTCCGAAGGTGGTTCCATTGGGCGGCACTGGGTTTTGGATCCGATAGATGGTACTAAAG 630
Lotus      AGTCTGAAGGTGGCTCTGTTGGACGGCACTGGGTTTTGGATCCAATAGATGGCACTAAAG 520
Soybean    AATCTGAAGGTGGTTCAGTTGGACGGCACTGGGTTTTGGATCCGATAGATGGTACTAAAG 593
SAL1       CATCTGAAGGTGGTCCAAATGGTCGACACTGGGTCTTGGATCCAATTGATGGCACTAAAG 611
Oilseed    CATCTGAAGGTGGTCCTAATGGTCGACACTGGGTCTTGGATCCTATCGATGGCACCAAAG 556
Poplar     AATCTGAAGGTGTTCTCGAGGGCAGACACTGGGTTCTGGACCCAATAGATGGCACTAAAG 528
Cotton     GATCTGAAGGTGGTTCCCAAGGTCGACACTGGGTTTTGGATCCTATAGATGGTACTAAAG 566
tomato     GATCTGAAGGGGTCCTTCTGGTCAGCACTGGGTGTTGGATCCTATTGATGGTACTAAAG 498
Potato     GATCTGAAGGGGTCCTTCTGGTCAGCACTGGGTGTTGGATCCTATTGATGGTACTAAAG 562
onion      AATCTGAAGGAGGCCCTCATGGGCGACACTGGGTACTGGATCCTATAGATGGCACCAAAG 604
Wheat      AGTCTGAAGGAGGTCCATCTGGCCGACATTGGGTTCTGGATCCAATTGATGGGACTAAAG 645
barley     AGTCCGAGGGTGGTCCATCTGGCCGACATTGGGTCTAGATCCAATTGATGGGACTAAAG 539
rice       AGTCTGAGGGAGGTCCATCTGGGCAACACTGGGTGCTGGATCCAATTGATGGGACTAAAG 598
maize      AGTCTGAGGGAGGTCCATCTGGACGACATTGGGTGCTTGATCCGATTGACGGTACTAAAG 612
           ** ** **  *       **     **  *****   * ** ** ** ** ** ** *

Spruce     GATTTCTTAGAGGAGACCAATATGCTGTAGCCTTGGGCTTATTGGATGAAGGAGAAGTTA 685
Pine       GATTTCTTAGGGGAGACCAATATGCTGTAGCCTTAGGCTTATTGGATGAAGGAGAAGTTA 501
Medicago   GTTTTGTAAGAGGAGACCAATATGCCATAGCCATTAGCTCTGCTAGATGAAGGGAAAGTTG 690
Lotus      GGTTTGTAAGAGGAGACCAATACGCTATTGCATTAGCTTTGCTAAATGAAGGAAAAGTTG 580
Soybean    GGTTTGTAAGAGGAGACCAATATGCTATAGCCGTTAGCTTTACTAGATGAAGGCAAAGTTG 653
SAL1       GATTTCTGAGGGGAGATCAATACGCAGTAGCACTAGGATTGCTCGAGGAAGGGAAAGTAG 671
Oilseed    GATTTTTGAGGGGAGATCAGTACGCGGTAGCACTAGGATTACTCGAGGAAGGGAAAGTAG 616
Poplar     GGTTTTAAGAGGAGATCAATATGCAATAGCTTTAGCATTGCTAGATGAAGGGACAGTAG 588
Cotton     GTTTTCTGAGAGGAGATCAATATGCAATAGCCATTGGCTTTGCTAGATGGAGGAAAAGTTG 626
tomato     GGTTTCTAAGGGGAGACCAATATGCAATTGCATTGGGATTGCTAGATGAAGGGAAGGTGG 558
Potato     GGTTTCTGAGGGGAGACCAATATGCAATTGCATTGGGATTGCTAGATGAAGGGAAGGTGG 622
onion      GGTTTGTACGAGGAGATCAGTATGCCATTGCGCTTGCATTGATAGATGAAGGAAAAGTAG 664
Wheat      GTTTCTTGAGAGGAGGCCAATATGCAATCGCACTGGCACTGCTTGATGAGGGCAAAGTTG 705
barley     GATTCGTGAGAGGAGGCCAATATGCCATTGCACTGGCACTGCTTGATGAGGGCAAAGTTG 599
rice       GTTTCTTAAGGGGAGACCAATATGCTATTGCCCTGGCTCTGCTTGATGAAGGTAAAGTTG 658
maize      GTTTCTTGAGGGGCGACCAATATGCCATTGGCTCTGCTTGATGAAGGTAAAGTTG 672
           * **  *   *   ** * **  **    *   *    *  *  ** **        **
```

Fig. 6B (cont<sup>d</sup>)

```
Spruce    TTTTGGGTGTGCTGGCCTGCCCAAATTTGCCCTGGACATCAGTTAGCATCAGTGC----- 740
Pine      TTTTGGGTGTGCTGGCCTGCCCAAATTTGCCCTGGACATCAGTTAGCATCAGTGC----- 556
Medicago  TATTGGGTGTCTTGGCTTGTCCAAATCTTCCGCTGGGAACCATTGGCCCGAATCA---AC 747
Lotus     TATTGGGTGTCTTGGCTTGCCCGAATCTTCCACTGGCATCCATTGCCTGTAATCA---GC 637
Soybean   TATTGGGTGTCTTGGCTTGTCCAAACCTTCCACTGGCATCCATTGGCTCCAATCA---GC 710
SAL1      TTTTAGGTGTGCTTGCTTGTCCAAACTTGCCGTTAGCATCCATAGCAGGAAACAACAAGA 731
Oilseed   TGTTAGGTGTGCTTGCTTGTCCAAACTTGCCATTAACATCCATAGCAGGAAACAA---GA 673
Poplar    TGTTGGGCGTCTTGGCTTGTCCCAATCTTCCGTTACCTTCCATTGCTGGTGGCTC---TC 645
Cotton    TCCTGGGTGTGCTGGCTTGTCCAAATCTTCCACTAACTTCCCTCAGTGATGCTGG---TC 683
tomato    TTTTGGGCGTCTTAGCCTGTCCAAATCTTCCATTATCTTCTCTTGCCTCCCACAA---TC 615
Potato    TTTTGGGCGTCTTATCCTGTCCAAATCTTCCATTATCTTCTCTTGCCTCCCACAA---TC 679
onion     TTCTCGGAGTTCTTTCATGTCCGAATCTTCCTCTTACCCCAATTGGTAGTTCTAA---TA 721
Wheat     TTTTGGGCGTGTTGGGATGTCCAAATCTTCCTTTGACATCAATAAGCAACCTCAA---TG 762
barley    TCTTAGGTGTGTTGGGATGTCCAAATCTTCCTTTGACATCAATAAGTAACCTCAG---TG 656
rice      TTTTGGGTGTATTGGCTTGTCCCAACCTTTCTTTGGGATCAATAGGCAACCTTAA---TG 715
maize     TTTTGGGTGTATTGGCTTGTCCAAATCTTCCATTGTCATCAATAAACAACATCAA---TG 729
                * * ** **  *    **  ** **  *  *          *  *

Spruce    -CCGCCCTTCAAATGATCCAATTGGTTGCCTTTTTTCTGCAAGAAAAG------------ 787
Pine      -TCGCCCTTCAAATGATCCAATTGGTTGTCTTTTTTCTGCAATAAAAGGAGCTGGAACTA 615
Medicago  CGCATTCTTCTTCTAATGAAGTTGGGTGTCTTTTCTTTGCCAAAGTTGGCAATGGAACAT 807
Lotus     AGCATTCTACTTCTAATGAAGTTGGTTGTCTTTTCTTTGCTAAAGTTGGCGATGGAACAT 697
Soybean   AGCATTCTTCTTCAAATGAAGTTGGTTGTCTCTTCTTTGCTAAAGTTGGTGATGGAACAT 770
SAL1      ACAAATCTTCGTCAGACGAAATTGGATGCCTCTTCTTTGCTACAATTGGTTCAGGGACAT 791
Oilseed   ACTCTTCTTCTTCAGACGAAATCGGATGCA-CTTCTTTGCTACGATTGT-CAGGGACAT 731
Poplar    AGCATTCTTTGCCTGGCGAAGTTGGTTGCCTTTTCTTTTCTGTAGTTGGGGGTGGAACTT 705
Cotton    AGCATTCTCCAAATAATAAAGTTGGCTGCCTTTTCTTTGCTGTAGTAGGTGGTGGAACTT 743
tomato    TACAGGATGATCAAGACAAAGTTGGTTGCCTTTTTTATGCCCAAGTTGGTTCTGAACTT 675
Potato    TACAGGATGATCAAGACAAAGTTGGTTGCCTTTTTTATGCCCAAGTTGGTTCTGAACTT 739
onion     CAAATCCTACTGAAAACCAAGTTGGCTGTCTTTTCTCTGCTAAAATTGGTTGTGGTGCTG 781
Wheat     GTAGCTCATCAGGAGATCAAACGGGGCCCTCTTTTTGCAGCTGCAATCGGTTGTGGTGCTG 822
barley    ATAGCTCATCAAGAGATCAAACCGGGGCCCTCTTTTTCAGCTGCAATCGGTTGTGGTGCTG 716
rice      GTGGCTCCTCGGGAGATCAAGTTGGTGCTCTCTTTTCTGCTACTATTGGTGTGGAGCTG 775
maize     GTAACTCTTCGGGAGATAAAGTTGGTGCCCTGTTTTCTGCTACAATTGGTTGTGGGGCTC 789
                   *  **       ** *    *        *

Spruce    ------------------------------------------------TGCCGTTG-- 795
Pine      CTG-TGCAATCATTGGATGGTTCTATACAACCTAAAAGGGTTTATGTAAGTGCCATAG-- 672
Medicago  ATA-TGCAAGCATTGGAT---GGTACTACACAAACTAAGGTGAATGTTAGTACTGTTG-- 861
Lotus     TTA-TGCAGGCAATGGAT---GGTTCTACACAGATCAGGGTGCATGTCAGTGCTATTG-- 751
Soybean   ATA-TGCAAGCACTGGGC---GGTTCTACACAAACTAGGGTGCATGTCTGTGATATTG-- 824
SAL1      ATA-TGCAGCTCCTAGATTCAAAATCTTCTCCTGTAAAAGTGCAAGTCTCTAGTGTTG-- 848
Oilseed   ACA-TGCAGCCCTTAGACTCGAAATCGAACAGTC-------------------------- 764
Poplar    ACA-TGCAGCCACTGGAT---AGCTCTTCAGCAGTGAAGGTGCAAGTCAACGCTACTG-- 759
Cotton    ATA-TGCAGCCACTTGAT---GGTTCTTCGGCAGTAAAGGTGCAAGTAAGTGCTGTTG-- 797
tomato    ATA-TGCAGTCTCTTGAT---GGCTCTACACCAATAAAGGTGCATGTAACTGATTTAG-- 729
Potato    ATA-TGCAGTCTCTTGAT---GGCTCTACACCAATAAAGGTGCATGTAACTGATTTAG-- 793
onion     AGAATGCAATCACTAGAAT--GGTTCGGTGTCGTCAAAGGTACATGTTAGCAATATCG-- 837
Wheat     AAG-TAGAGTCATTAGAG---GGCTCTCCACCACAAAAGATTAGTGTTTGTACCATCG-- 876
barley    AAG-AGCAGTCTTTGGAT---GGCTCTCCACCACAAAAGATTAGTGTTTGTACCATCATT 772
rice      AAG-TAGAGTCTTTACAG---GGCTCTCCAGCACAAAAGATTAGTGTCTGTTCCATCG-- 829
maize     AAG-TAGAGTCCTTAGAT---GGCTCTCCACCACAAAAGATTAGTGTTTGCTCCATCG-- 843
```

Fig. 6B (cont$^d$)

```
Spruce      ---AAAAGTC---TGAAGATGCA-TCTTTCTTTGAA-TCATATGAG-GCAG-CACATTCC 845
Pine        ---AAAAGTC---TGAAGAAGCA-TCTTTTTTTGAA-TCATACGAG-GCAG-CACATTCC 722
Medicago    ---ACAATCC---AGAAGAAGCA-TCATTTTTTGAA-TCTTATGAA-GCAG-CACACTCC 911
Lotus       ---ATAATCC---AGAAGAGGCA-TCATTTTTTGAG-TCTTTTGAA-GCAG-CGCACTCC 801
Soybean     ---ATAACCC---AGAGGAAGCA-TCATTTTTCGAA-TCTTTTGAA-GCAG-CACACTCC 874
SAL1        ---AGAATCC---TGAAGAGGCA-TCGTTCTTCGAG-TCATTCGAA-GGAG-CTCACTCT 898
Oilseed     ------------------------------------------------------------
Poplar      ---ACAATCC---TGAAGAAGCA-TCGCTCTTTGAA-TCATATGAA-GCAG-CACACTCC 809
Cotton      ---AAAATCC---TGAAGAAGCA-TCATTCTTTGAG-TCTTATGAA-GCAG-CACACTCC 847
tomato      ---ACAACCC---TGAAGAGGCA-TCTTTTTTTGAA-TCTTTTGAA-GCAG-CACATTCT 779
Potato      ---ACAACCCC-TTGAAGAGGCA-TCTTTTTTTGAAATCTTTTGAAAGCAGACACATTTC 848
onion       ---AAAATCC---AGCCGACGCA-TCATTCTTTGAA-TCATATGAA-GCTG-CTCATTCT 887
Wheat       ---ACAATC----CAGTGAATGCC-TCGTTCTTTGAA-TCCTATGAA-GGAG-CACACACA 926
barley      GCTACAAATAAACAGTCAATGCCATCAGTCCTTGAA-GCCTATCAA-GGAG-CACACACC 829
rice        ---ACAATC----CAGTCGAAGCT-TCATTCTTTGAG-TCCTACGAA-GGGG-CACACTCC 879
maize       ---ACAATC----CTGTCAATGCA-TCATTTTTTGAA-TCCTATGAA-AGTG-CACACTCC 893

Spruce      AT--GCATGACTTG--ACAGCTACAATAGCAAA-GATCCTG--GGTGTAAAAGCACCACC 898
Pine        AT--GCATGACTTG--ACGGCTACAATAGCGAA-GATCCTG--GGTGTAAAAGCACCCCC 775
Medicago    TC--ACATGACTTG-TCTAGCACT-ATTGCAGT-AAAACTC--GGCGTCAAAGCACCGCC 964
Lotus       TT--ACATGACTTG-TCTAGCTCC-ATTGCAGA-AAAACTT--GGTGTTAAGGCACCGCC 854
Soybean     TT--GCATGACTTA-TCTAGCTCA-ATCGCAGA-AAAACTT--GGTGTCAAAGCACCACC 927
SAL1        CT--ACATGACTTA-TCCAGCTCC-ATTGCCAA-TAAACTC--GGTGTCAAAGCTCCACC 951
Oilseed     ------------------------------------------------------------
Poplar      AT--GCATGATCTA-TCTAGTTCA-ATTGTCAA-AAAACTT--GGTGTCAAAGCACCACC 862
Cotton      AT--GCATGATTTA-TCTAGTTTG-ATTGCCCA-AAAACTC--GGCGTCAAAGCACCACC 900
tomato      TT--GCATGACCTA-TCTAGTTTG-ATAGCAAA-GAAACTT--GGTGTAAAAGCCCCCCC 832
Potato      TTTGGCATGACCTAATCTAGTTTGGATAGCAAA-GAAACCTTGGGTGGTAAAAGCCCCGC 907
onion       CT--ACATGACTTA-TCTAGCTCC-ATAGCTAA-GAAGCTT--GGCGTGCAAGCACCGCC 940
Wheat       AT--GCATGATTTA-ACTGGCTCT-ATAGCGGA-GAAACTT--GGTGTCCAAGCTCCTCC 979
barley      AA--GCGAGAAAAA-ACAGGCCCC-GTAGCCAATGAAAAAG--GGTGTCCAACCTCCTCC 883
rice        TT--GCGTGATTTA-ACAGGCTCC-ATTGCGGA-GAAACTT--GGTGTCCAAGCTCCTCC 932
maize       AT--GCATGATTTG-ACTGGCTCT-ATTGCAGA-GAAACTT--GGTGTCCAAGCTCCTCC 946

Spruce      AGTTA--GAA--TAGATA-GTCAGGCAAAATA-----TGGAGCAATGGCAAG-GGGTGAT 947
Pine        AGTTA--GAA--TAGATA-GTCAGGCAAAATA-----TGGTGCAATGGCAAG-GGGTGAT 824
Medicago    AGTCA--GAA--TTGACA-GCCAAGCAAAATA-----CGGAGCTCTATCCAG-AGGAGAT 1013
Lotus       AGTCA--GAA--TTGACA-GCCAAGCAAAATA-----TGGAGCTCTGT------------ 892
Soybean     AGTCA--GAA--TTGATA-GCCAAGCAAAATA-----TGGAGCTTTGTCAAG-AGGAGAT 976
SAL1        AGTCC--GTA--TTGATA-GCCAAGCAAAGTA-----TGGAGCTTTATCAAG-AGGAGAT 1000
Oilseed     ------------------------------------------------------------
Poplar      AGTTA--GAA--TTGATA-GCCAAGCAAAGTA-----TGGCGCTCTGTCTAG-AGGAGAT 911
Cotton      GGTTA--GAA--TTGATA-GCCAGGCGAAGTA-----TGGTGCTCTATCCAG-AGGAGAT 949
tomato      AGTTC--GAA--TAGACA-GCCAGGCAAAGTA-----TGGTGCTTTGTCCCG-TGGAGAT 881
Potato      AGGTC--GA---TATACACGCCGGGCAAAGA-------GGGCTTCGCCCCGGCGAAAAT 955
onion       TGTAA--GAA--TTGATA-GCCAAGCAAAATA-----TGGTGCTCTTTCACG-AGGAGAT 989
Wheat       AGTCA--GAA--TAGATA-GCCAAGCAAAATA-----TGGTGCTCTGGCCCG-TGGCGAT 1028
barley      AGTCACTGAAGTTAGATA-GCCAACCAAAATAATGATCGCTATGCTACTCCG-TGGACAT 941
rice        AGTTA--GAA--TTGATA-GCCAAGCAAAATA-----CGGTGCCCTAGCCCG-AGGTGAC 981
maize       AGTTA--GAA--TCGACA-GCCAAGCAAAATA-----TGGTGCTCTGGCCCG-AGGTGAT 995
```

Fig. 6B (cont$^d$)

```
Spruce     GGAGCAAT----ATATCTTCGCTTTCCTCGTCCAGGCTATCGTGAAAAGATTTGGGATCA 1003
Pine       GGAGCAAT----ATATTTTCGCTTTCCTTGTCCAGGCTATCGTGAAAAGATTTGGGATCA 880
Medicago   GGGGCTAT----ATATTTGCGTTTCCCCAACAAAGGATACCGTGAAAAAATATGGGATCA 1069
Lotus      ------------------------------------------------------------
Soybean    GGGGCTAT----ATATTTGCGTTTCCCTCACAGAGGATACCGTGAAAAAATATGGGATCA 1032
SAL1       GGAGCTAT----ATACTTACGGTTTCCTCATAAAGGATACCGCGAAAAGATTTGGGACCA 1056
Oilseed    ------------------------------------------------------------
Poplar     GGGGTCAT----ATACTTGCGATTTCCACATAAAGGTTACCGTGAGAAAATATGGGATCA 967
Cotton     GGAGCCAT----ATATCTGCGTCTTCCACACAAAGGGTATCGAGAAAAAATATGGGATCA 1005
tomato     GGAGCAAT----ATATCTGCGGTTTCCTCATAAAGGCTACCGCGAGAAGATATGGGATCA 937
Potato     GGCACAAA----TAATCTNGGGGTCCCCAAAAAGGG--ACCAGGAAAAATATCGGACCA 1009
onion      GGTGCTAT----ATATTTACGGTTTCCACATAAAGGGTACCGTGAGAAAATTTGGGATCA 1045
Wheat      GGTGCCAT----TTACTTGCGTTTTCCACACAAGGGTTATAAGGAAAAGATATGGGATCA 1084
barley     GGATGCACACTGTTAATGGCGTAACCCACACGAGGGTTACAGGGAAACAATATGGGATCA 1001
rice       GGTGCCAT----TTACTTGCGTTTTCCACACAAAGGTTACAGAGAGAAGATCTGGGATCA 1037
maize      GGCGCCAT----TTACTTGCGCTTTCCACACAAAGGTTATAGAGAGAAAATATGGGACCA 1051

Spruce     TGCAGCTGGTTGCATCGTAATCCAAGA-------------------GGCTGGTGGTGTT 1043
Pine       TGCAGCTGGTTGTATTGTAATCCAAGAAAATTCATCCGAATTGCAGAGGCTGGTGGTGTT 940
Medicago   TGCTGCTGGTTGTATTGTTGTGAGTGA-------------------AGCTGGAGGTATT 1109
Lotus      ------------------------------------------------------------
Soybean    TGCTGCTGGCAGCATTGTTGTGACTGA-------------------AGCTGGAGGTATT 1072
SAL1       TGTCGCTGGTGCTATAGTTGTTACAGA-------------------GGCGGGTGGAATA 1096
Oilseed    ------------------------------------------------------------
Poplar     TGCTGCTGGATGCATAGTTGTATCAGA-------------------AGCTGGGGGACTG 1007
Cotton     TGCTGCTGGGTGTATTGTTGTGAGTGA-------------------AGCTGGGGGTGTG 1045
tomato     TGCTGCTGGATATCTCGTTGTTGCAGA-------------------AGCTGGAGGTGTT 977
Potato     CG-----GGGGAGACTCCTGGGGCACA-------------------CAGCGGGGG-GTC 1043
onion      TGCAGCTGGCTGCATTGTCGTCACAGA-------------------AGCTGGAGGGGTA 1085
Wheat      TGCAGCTGGCGCAATTGTCGTCACAGA-------------------AGCTGGAGGTGTA 1124
barley     TGCAGCTGGCTCAATTGTCGTCACGGA-------------------AGCTGGAGGTGTA 1041
rice       TGCAGCTGGGTCAATCGTCGTGACAGA-------------------AGCTGGAGGTCTG 1077
maize      TGCAGCAGGATCAATTGTCGTGACAGA-------------------AGCTGGAGGCATA 1091

Spruce     GTGGTTGATGCTGCTGGGAAACCTCTTGATTTCTCACAGGGGAGGTATCTGGATGTGGAA 1103
Pine       GTAGTTGATGCTGCTGGAAAACCTCTTGATTTCTCACGGGGGAGGTATCTGGATGTGGAA 1000
Medicago   GTCTCAGATGCTGCCGGAAACCCTTTGGACTTCTCAAAAGGAAAGTTCCTTGATGTTGAT 1169
Lotus      ------------------------------------------------------------
Soybean    GCCATGGATGCTGCGGGGAACCCTTTGGACTTTTCAAAAGGAAAGTTTCTTGATGTTGTA 1132
SAL1       GTGACAGATGCAGCAGGAAAGCCACTGGATTTCTCGAAAGGGAAGTATCTTGATTTGGAC 1156
Oilseed    ------------------------------------------------------------
Poplar     GTCACAGATGTTGCGGGGAACCCCCTTAGATTTTTCAAGAGGAAGATACCTGGATCTTGAC 1067
Cotton     GTCACAGATGCTGCAGGGCAGCCATTGGATTTTTCAAAGGGAAAGTATCTTGATCTGGAC 1105
tomato     GTCTCAGATGCTGCAGGAAACCCTTTGGACTTCTCCAAGGGAAGATACCTTGATTTACAC 1037
Potato     CACACAAG-GCGACAG-------------------------------------------- 1058
onion      GCAACCGATGCTGCTGGGAATGCCTTAGA-TTCTCGAAAGGAAGTATCTTTGAT--TAAT 1142
Wheat      GTAACAGATGCCTCAGGAAACGATCTCGATTTCTCGAAAGGGAGATTTCTTGATGTTGAC 1184
barley     GTTAAAGATGCCTCAGGAAACGATCTCGATTTCTCGAAAGGAAGATTTCTTGATCGTGAC 1101
rice       GTGACAGATGCATCAGGAAACGATTTGGATTTCTCCAAAGGGAGATTTCTTGATCTCGAC 1137
maize      GTAACAGATGCTGCGGGAAACGACTTGGATTTCTCCAAAGGGAGATTTCTGGATCTCGAC 1151
```

Fig. 6B (cont$^d$)

```
Spruce     AGGGGTATAATTGCAACCAATGCCAAACTGATGCCATTGCTTC-TTAATGC-AGTGCAAG 1161
Pine       AAGGGTATAATTGCAACCAATGCCAAACTGATGCCATTGCTTT-TTAATGC-AGTGCAAG 1058
Medicago   ACTGGTATTATTGTTACAAACCAGAACTTGATGCCTTCGCTTT-TGAGAGC-AGTTAAAG 1227
Lotus      ------------------------------------------------------------
Soybean    TCTGGTATTATTGTTACAAACCAGAAATTGATGCCATCACTTC-TGACAGC-AGTTAAAG 1190
SAL1       ACAGGCATTATCGTTGCTAACGAGAAGCTAATGCCTCTGCTTT-TGAAAGC-AGTTCGTG 1214
Oilseed    ------------------------------------------------------------
Poplar     ACAGGCATCATTGTTACGAATCAGAAACTGATGCCATTACTTT-TGAAGGC-AGTTAGAG 1125
Cotton     ACAGGCATCATTGTCACCAACCAGAAGTTGATGCCATTACTGT-TTAATGC-AGTTAGAA 1163
tomato     GAAGGCATAATCGTTACCAATCAAAAGCTGATGCCTGCTCTCC-TCAAGGC-TGTTAAAG 1095
Potato     ------------------------------------------------------------
onion      ACAGGCAT-ATTGTCACCAAC--AGAGCTGATGCCAAAACTTT-TGGAGCC-GTACAAT- 1196
Wheat      ACAGGCATCATTGCCACAAATAAGCAGTTGATGCCATCACTGC-TGAAGTC-TGTCCAGG 1242
barley     ACAGGCATCATTGCTACAAATAAACAGTTGATGCCATCAGTNCCTGAAGTNCTGTCCAGG 1161
rice       ACAGGGATCATCGCGACGAACAAGCAGCTGATGCCTTCACTCC-TGAAGGC-TGTGCAAG 1195
maize      ACAGGCATCATCGCAACCAACAAGGAGTTGATGCCGTCGCTCC-TGAAAGC-TGTCCAAG 1209

Spruce     CTGCTCTGAAGGAAGAAGGAAATGTTCGAAAGGCTGGTTCCTTGTAGCACCATTCATTTA 1221
Pine       CTGCTCTCAAGG------------------------------------------------ 1070
Medicago   AATCACTCAATGAGAAAGCATCATCCTTGTAATATCTGTC-AAGTGTATGATTCTACTAC 1286
Lotus      ------------------------------------------------------------
Soybean    AAGCACTCAATGAGAAAGCATCATCCTTGTGATTTCCATTTAAGCGAATGATTCTACAAA 1250
SAL1       ACTCCATAGCTGAGCAAGAGAAAGCTTCAGCTCTCTGA---------------------- 1252
Oilseed    ------------------------------------------------------------
Poplar     AATCCATAGAGGAGAAAGCTTCATCATTGTGATTC--TTT---ACTGATGAATGAAGTCAT 1181
Cotton     AATCTATCCAGGAGAAAGCTTCATCTTTGTGATTCATTTT--AGAGGCAGGCTTCATCCT 1221
tomato     AATCTTTGAATGAGAAAGCTTCATCCTTGTGATGATCAAA--CCAATAACAATACGCTGC 1153
Potato     ------------------------------------------------------------
onion      ------------------------------------------------------------
Wheat      AGGCCATCAAGGAGAAAAGCCAGGCCCCTTCCCCATTGTAGAAGCTTTTTTGGTTTGAAC 1302
barley     AGGCAATCAAGGAGAAAAAACAGGCCTCTTCTCCATTGTAAAAGGTTTTTTTAACCTTNC 1221
rice       ATGCCATCAAGGAGCAAAACCAGGCTGCTTCCCCGTTGTAGTAGCTGTCTCAATCCACAA 1255
maize      AGGCTATTAAAGAGACGAACCAGGCTGCCTCCCTCTTATAGCTGTTGTAGTGGTCGACAA 1269

Spruce     TTGAACCTAATTAGGGATGGAAGTTGGAACTTATGCTGATGAAATAAAACAATTCTATTT 1281
Pine       ------------------------------------------------------------
Medicago   TGAGCTTCCTCATTTTGTTGTCAGCCAGTTATAT---GAACCTTCCTCTCAATTGTGCTA 1343
Lotus      ------------------------------------------------------------
Soybean    TGAGCTTGCTAACGTTGTTGTCGGCTCGTGTTATATGGGGCCTTCCCCTCAATTGTGCTA 1310
SAL1       ------------------------------------------------------------
Oilseed    ------------------------------------------------------------
Poplar     TTCCT------TTGCTAAGTT----TGTTAGCAACTCAAATCAGTTTTACGTG----ACT 1227
Cotton     TTCCTCATAACTTGCTCTGTTAAGCTGGTTGAAACTTGA-TTATTTTTGCCTTCAATGCT 1280
tomato     AGCTATCTTATTGTAGTTCCCAGAATGGTACTTGCAGCTGCTCATTTTCACCTGTTCTTC 1213
Potato     ------------------------------------------------------------
onion      ------------------------------------------------------------
Wheat      CTTCCCTGTTGTAGTTGGATTGATCCAAAACAATGAT-CGCAATGCCACACC-------- 1353
barley     CCTGT-TACTGAAGTTGGATTGGTCCAAAATAATGAT-CGCTATGCTACTNCCTTGTTCA 1279
rice       TCCAC-AAATATCATAATGTTTCCATATAATAATAAT-TGCAGTGCTGCTTCCCCATCAA 1313
maize      AAAAGTAGTTGCAAAATTTTCGTACTGGCAAACAGGTGTGCATCATTTCTCCGTGGTATT 1329
```

Fig. 6B (cont$^d$)

```
Spruce      GCACAAGGTCCTTCCTTTAAGAGATATAACTGAGTGTCGTGGTAGGTGTGTCAACTCTCT 1341
Pine        ------------------------------------------------------------
Medicago    CATTTCATACGCGATCTGATGAAGCTAAGCATATGACTGGACTTCCTCCAACACTTTATT 1403
Lotus       ------------------------------------------------------------
Soybean     TATTTCAT------TCTGATGAAGTTAAACAAATGATGGGACTTCCTCTGATACTTCCTT 1364
SAL1        ------------------------------------------------------------
Oilseed     ------------------------------------------------------------
Poplar      TGAATTTTCCACTCTATGTTTGCTCAATGTATGTTGAGCATGAAACTCTTGCAACTTGTG 1287
Cotton      TGAACTTTT-ATCATTCTTCTCCCCAATGCTTAT--AGGAAGATTTTCATTTAGCATGC- 1336
tomato      TCCTTCTACACATTTCTGATATCACTTTTTAGCTCTTTGATTGTCATCTCAACTCAGCTT 1273
Potato      ------------------------------------------------------------
onion       ------------------------------------------------------------
Wheat       --TTATTCACACTGT-TCTAT-GTGTAAAT--GACCTTTTTGTTGGGACAAAGGCAAT-C 1406
barley      T-TTATTCACACTGT-T-TAT-GTGTAAGT--GACCTTTT-GTTGGAAAAAATACAAC-C 1331
rice        CATTACTTTAAATGTGTGTACAGCACCACTTTGTTGTTGTTGCTGCTGCAAATTCAGTAT 1373
maize       ACAGAGTCTAGCAAA-TTTATAGCATCAACCTGATTGGTGATCAGACGTCCATTCGTTTT 1388

Spruce      GGCTCTAGTCCTGGCCACATTTGCAGTGATAGACAATAAGTTGAAAACGGAAGTACATTA 1401
Pine        ------------------------------------------------------------
Medicago    TAAATCATATGCCTGTTCTGCTTTTTGCGTGTACTGTCTTCAAGATTCTTGTAATTTAAG 1463
Lotus       ------------------------------------------------------------
Soybean     TGTAGCAGCAGATTTGTGCTCTGGTTTTTTGCAGCTGCTATTTTCTTCTCCTTCTATATA 1424
SAL1        ------------------------------------------------------------
Oilseed     ------------------------------------------------------------
Poplar      AAGTTCAAATGTATTATCCGATGCATAATAGTAGTGTCATTCTGCTAAGCTAC------- 1340
Cotton      ATGAACAAGAATGGGA-CCAATAAATCTCATCTCTACAATTAAGACAATGTAATTGTAGA 1395
tomato      TGATAAACATTTTGTTGTTCTCTGGTTATGTCAACTCAACTTTGATTAAACATTATATAT 1333
Potato      ------------------------------------------------------------
onion       ------------------------------------------------------------
Wheat       CTTGTTGTATCACATTTGTACATC-TAAGGAGTGGTGACAGCCATGTCT---TAAATAAA 1462
barley      CTTGTTAT---------------------------------------------------- 1339
rice        CTTATTGTTGCACATTTCTGCATC-TA---ATTGGTGGGTGAGCTGGCA---CCACATGA 1426
maize       ACTGAATCACCTTCTTGGTGCAGCATTGCTAGAAGTGGACAACATGAATAATTTGAGTGA 1448

Spruce      ATTTCCTTTAATTTTC-------------------------------------------- 1417
Pine        ------------------------------------------------------------
Medicago    CTTGAGTTGTAGGTCCTTTTTCTTCTTGCAAGTACTTTTTTCCTCCCAACTTT----CTT 1519
Lotus       ------------------------------------------------------------
Soybean     CCTGTCCTTTTCTCTCCTTTTCTATTAATAAACAGAGATGAGAGATCTTATTTTAAACTT 1484
SAL1        ------------------------------------------------------------
Oilseed     ------------------------------------------------------------
Poplar      ------------------------------------------------------------
Cotton      CTAGAACTTGAAAGCATGGTCCTAGGGCCTTGAGCCTTTCTCTTTGTCCTACCTGGCAGTT 1455
tomato      TTCTCTTGGTATGTTTTTTTTT-------------------------------------- 1355
Potato      ------------------------------------------------------------
onion       ------------------------------------------------------------
Wheat       AGAGGCATCTGCCTGCAGTTATAAATATC--TTAGCATAGCTTTGTTCAACATAAATGTC 1520
barley      ------------------------------------------------------------
rice        ATGTTCTTTCATCTGGATTCAGAAGAAATAATTAAATTGGCCTGATTCTCCCTAACTCGG 1486
maize       GTCCATAGTTGCCTGAACTCAGCTTTGGCATTTGAACTGGTTATAGAAATTGTGAA-ATA 1507

Medicago    TTCTATTAATAGATATTTTTATTTC----------------------------------- 1544
Soybean     GTTTGATAATTAATTCTTCTAGATTACTTG------------------------------ 1514
Cotton      GGGTTTAGGTGTAATTAATTAGATAAAGGAACTGTGTTGTTGAATACAAACATATTACAT 1515
Wheat       AGCAACAACTATTCTTTGTGTGAGCAACAGCCAATCTCTTGTATTATTTCTTTCAGAGAT 1580
rice        GGCAATATTGCT------------------------------------------------ 1498
maize       ATTAATGGATATTTGGAAGACAAACTTGAACTTCAAG----------------------- 1544

Cotton      TATTACTAAACTTATTTCATGGTAAAACAAGTGTGAAGTCCTCTCCTTCCCGACCGTTTA 1575
Wheat       TTTTGATGTGCAGTTTATCCCCCCTTGTTAAATTACATACAATTCAAGCTATAATCAATA 1640
```

Fig. 6B (cont<sup>d</sup>)

```
Cotton    CCTTACATGGTTT--------------------------------------------------- 1588
Wheat     TTAACTCTTATGGTACCAACTAAATCATCATTCATGGGTACTTGCAGACTCAACATTGCA 1700

Wheat     GAGCTAAGGCTAATAGGACTAANCAGGCACATCAGCTGGATACTCTGCAGAATGCTTTTT 1760
Wheat     GATGGTATCCAGCAGCTACCGCTCTTGCTCACNAAGGNTGGGAAGCATTTGNTCATACAC 1820
Wheat     ATCANTGAAGAGCTCCGCAAGGCCGTGTTTTGGAACCTCCGGCNACTGAATGGCTTGCAG 1880
Wheat     GAACNTTGCCNANATGTCCTGAGTAAACCCTGAGTGCGCACACATCATCCCTGAACAATT 1940
Wheat     CGTCCNGAGACGGATCCCGTGTCCAAGCCAACNANAACGGCNGANTGGTTAACTCGAGCC 2000
```

Fig. 6B (cont$^d$)

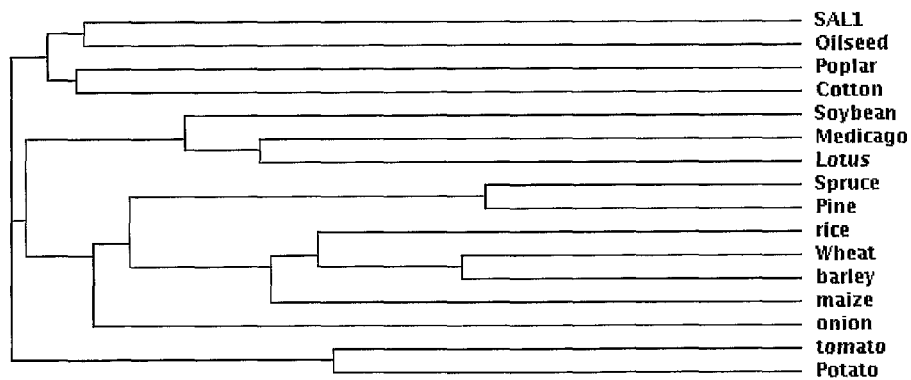

Fig. 6C

SALK_020882 Genomic Sequence (SEQ ID NO: 3) – according to TAIR

```
   1   GACATATATT TATCTTCTTG AAAAGCGAAT GATGTCTATA AATTGTTTTC
  51   GAACAGCGAA GGCTCCGCTT CAATCATTTG TAGCAGTAAG AACGAATTCG
 101   AGACCTAGAA ATTCATCGAA CCGTCTCGTT TCTGTATTCG GACGCAAGTC
 151   TTCTTCTCCT TCATTTGTTA CTCTCAGAGT TGTTTCATCG ATGGCTTACG
 201   AGAAAGAGCT TGATGCTGCT AAGAAAGCTG CTTCACTCGC TGCTCGTCTC
 251   TGTCAGGTTA GGGTTTTTTC GATTCAATCA TGACCCATAG ATTCTAAAGT
 301   TTGATTCTTT AAGAAACCCA TTTTGTAAAT CTTCCAAATT TCGTTTAACA
 351   TTTTGTGTTT ATTGTGCATT GCATCTGTAA TTGGAATAG ATTCTAGTGA
 401   TATAGTGTAA TGGTCCTCTA CATACGAAGC TCGTGTAAAT CTTTGATCAA
 451   AATCTTATCT TTGTGTTTTG GGTTTGTTTC AGAAAGTTCA AAAGGCTTTG
 501   TTGCAATCAG ATGTGCAATC AAAATCTGAT AAAAGTCCAG TGACCGTTGC
 551   TGATTATGGT TAGTTTGTTA TACCTGTCCC TGATTAGAAA AAGCTCTTCT
 601   CTTTGAATGT TACTGAGATT GTTAGGAAAT CACTTAATTT GATCTGTCTT
 651   GTGTTGAATT TCAGGTTCAC AAGCAGTTGT TAGTTTAGTC TTAGAAAAAG
 701   AGCTCAGTTC TGAACCCTTT TCATTGGTGG CTGA[SALK_020882]AGAGGT
       GAAACTGCTT
 751   AATAAATCCT TGTTAGATGT CTCACACTTT ACTTATCTTT GAGTTTGTGT
 801   TTATGGACTC ACATTGTCTA AAATGATCTA TATAGGACTC AGGCGATCTA
 851   CGCAAGGATG GTTCTCAGGA TACTCTGGAG CGCATCACAA AACTCGTGAA
 901   CGACACTTTG GCTACCGAGG AATCGTTTAA TGGCTCTACT TTGTCTACTG
 951   ATGATCTACT TAGAGCCATT GACTGTGGAA CATCTGAAGG TGGTCCAAAT
1001   GGTCGACACT GGGTCTTGGA TCCAATTGAT GGCACTAAAG GGTACGTTTT
1051   AAAACTAACT AGCCTAAAGT CAAATCTTCT TATTTCAGAG AAAATGTAAA
1101   TTTGATAGAA TGTTGAGTCA GATGTTATGT TCCTGACACT GAGCATTTTC
1151   ATGATTTTAG ATTTCTGAGG GGAGATCAAT ACGCAGTAGC ACTAGGATTG
1201   CTCGAGGAAG GGAAAGTAGT TTTAGGTGTG CTTGCTTGTC CAAACTTGCC
1251   GTTAGCATCC ATAGCAGGAA ACAACAAGAA CAAATCTTCG TCAGACGAAA
1301   TTGGATGCCT CTTCTTTGCT ACAATTGGTT CAGGGACATA TATGCAGCTC
1351   CTAGATTCAA AATCTTCTCC TGTAAAAGTG CAAGTCTCTA GTGTTGAGAA
1401   TCCTGAAGAG GCATCGTTCT TCGAGTCATT CGAAGGAGCT CACTCTCTAC
1451   ATGACTTATC CAGCTCCATT GCCAATGTAA ATTGCTTCTT TCCTTCCATG
1501   TGATTCCAGC TAATAGCTAA CTAATTTTCC TCATCCATTT GATCATGTTC
1551   TATGTTGTAA TATACAGAAA CTCGGTGTCA AAGCTCCACC AGTCCGTATT
1601   GATAGCCAAG CAAAGTATGG AGCTTTATCA AGAGGAGATG GAGCTATATA
1651   CTTACGGTTT CCTCATAAAG GATACCGCGA AAAGATTTGG GACCATGTCG
1701   CTGGTGCTAT AGTTGTTACA GGTAACATTA AGCTTACTC TCTATGAAGC
1751   TAATTTTATA GTGTCGACAT GCGGATGTAA ATAGATAAGG AATGCAAGGT
1801   TGATTCTTCT TTTTGGTGCA GAGGCGGGTG GAATAGTGAC AGATGCAGCA
1851   GGAAAGCCAC TGGATTTCTC GAAAGGGAAG TATCTTGATT TGGACACAGG
1901   CATTATCGTT GCTAACGAGA AGCTAATGCC TCTGCTTTTG AAAGCAGTTC
1951   GTGACTCCAT AGCTGAGCAA GAGAAAGCTT CAGCTCTCTG ATTTGTTTTT
2001   TTCTCTCGTA CGTTCTTTGT TTCTCTGTAA CTGTTGTTTC ATTTTCTTTC
2051   ACCGAATTTC ACCAGTGAGA ATTTCTTCCA TTTTCGAAAA AGAAATAAAA
2101   ATGAAATTCT GTTTTGGGCT AA
```

Fig. 9A

SALK_020882 Genomic Sequence (SEQ ID NO: 4) – according to Tail PCR studies

```
1     GACATATATT TATCTTCTTG AAAAGCGAAT CATGTCTATA AATTGTTTTC
51    GAACAGCGAA GGCTCCGCTT CAATCATTTG TAGCAGTAAG AACGAATTCG
101   AGACCTAGAA ATTCATCGAA CCGTCTCGTT TCTGTATTCG GACGCAAGTC
151   TTCTTCTCCT TCATTTGTTA CTCTCAGAGT TGTTTCATCG ATGGCTTACG
201   AGAAAGAGCT TGATGCTGCT AAGAAAGCTG CTTCACTCGC TGCTCGTCTC
251   TGTCAGGTTA GGGTTTTTTC GATTCAATCA TGACCCATAG ATTCTAAAGT
301   TTGATTCTTT AAGAAACCCA TTTTGTAAAT CTTCCAAATT TCGTTTAACA
351   TTTTGTGTTT ATTGTGCATT GCATCTGTAA TTGGGAATAG ATTCTAGTGA
401   TATAGTGTAA TGGTCCTCTA CATACGAAGC TCGTGTAAAT CTTTGATCAA
451   AATCTTATCT TTGTGTTTTG GGTTTGTTTC AGAAAGTTCA AAAGGCTTTG
501   TTGCAATCAG ATGTGCAATC AAAATCTGAT AAAAGTCCAG TGACCGTTGC
551   TGATTATGGT TAGTTTGTTA TACCTGTCCC TGATTAGAAA AAGCTCTTCT
601   CTTTGAATGT TACTGAGATT GTTAGGAAAT CACTTAATTT GATCTGTCTT
651   GTGTTGAATT TCAGGTTCAC AAGCAGTTGT TAGTTTAGTC TTAGAAAAAG
701   AGCTCAGTTC TGAACCCTTT TCATTGGTGG CTGA[SALK_020882]TGCTT
751   AATAAATCCT TGTTAGATGT CTCACACTTT ACTTATCTTT GAGTTTGTGT
801   TTATGGACTC ACATTGTCTA AAATGATCTA TATAGGACTC AGGCGATCTA
851   CGCAAGGATG GTTCTCAGGA TACTCTGGAG CGCATCACAA AACTCGTGAA
901   CGACACTTTG GCTACCGAGG AATCGTTTAA TGGCTCTACT TTGTCTACTG
951   ATGATCTACT TAGAGCCATT GACTGTGGAA CATCTGAAGG TGGTCCAAAT
1001  GGTCGACACT GGGTCTTGGA TCCAATTGAT GGCACTAAAG GGTACGTTTT
1051  AAAACTAACT AGCCTAAAGT CAAATCTTCT TATTTCAGAG AAAATGTAAA
1101  TTTGATAGAA TGTTGAGTCA GATGTTATGT TCCTGACACT GAGCATTTTC
1151  ATGATTTTAG ATTTCTGAGG GGAGATCAAT ACGCAGTAGC ACTAGGATTG
1201  CTCGAGGAAG GGAAAGTAGT TTTAGGTGTG CTTGCTTGTC CAAACTTGCC
1251  GTTAGCATCC ATAGCAGGAA ACAACAAGAA CAAATCTTCG TCAGACGAAA
1301  TTGGATGCCT CTTCTTTGCT ACAATTGGTT CAGGGACATA TATGCAGCTC
1351  CTAGATTCAA AATCTTCTCC TGTAAAGTG CAAGTCTCTA GTGTTGAGAA
1401  TCCTGAAGAG GCATCGTTCT TCGAGTCATT CGAAGGAGCT CACTCTCTAC
1451  ATGACTTATC CAGCTCCATT GCCAATGTAA ATTGCTTCTT TCCTTCCATG
1501  TGATTCCAGC TAATAGCTAA CTAATTTTCC TCATCCATTT GATCATGTTC
1551  TATGTTGTAA TATACAGAAA CTCGGTGTCA AAGCTCCACC AGTCCGTATT
1601  GATAGCCAAG CAAAGTATGG AGCTTTATCA AGAGGAGATG GAGCTATATA
1651  CTTACGGTTT CCTCATAAAG GATACCGCGA AAAGATTTGG GACCATGTCG
1701  CTGGTGCTAT AGTTGTTACA GGTAACATTA AGCTTACTC TCTATGAAGC
1751  TAATTTTATA GTGTCGACAT GCGGATGTAA ATAGATAAGG AATGCAAGGT
1801  TGATTCTTCT TTTTGGTGCA GAGGCGGGTG GAATAGTGAC AGATGCAGCA
1851  GGAAAGCCAC TGGATTTCTC GAAAGGGAAG TATCTTGATT TGGACACAGG
1901  CATTATCGTT GCTAACGAGA AGCTAATGCC TCTGCTTTTG AAAGCAGTTC
1951  GTGACTCCAT AGCTGAGCAA GAGAAAGCTT CAGCTCTCTG ATTTGTTTTT
2001  TTCTCTCGTA CGTTCTTTGT TTCTCTGTAA CTGTTGTTTC ATTTTCTTTC
2051  ACCGAATTTC ACCAGTGAGA ATTTCTTCCA TTTTCGAAAA AGAAATAAAA
2101  ATGAAATTCT GTTTTGGGCT AA
```

Fig. 9B

SEQUENCE LISTING

<160> NUMBER OF SEQ ID NOS: 63

<210> SEQ ID NO 1
<211> LENGTH: 2122
<212> TYPE: DNA
<213> ORGANISM: Arabidopsis sp.
<220> FEATURE:
<221> NAME/KEY: misc_feature
<222> LOCATION: (29)..(31)
<223> OTHER INFORMATION: Start codon
<220> FEATURE:
<221> NAME/KEY: misc_feature
<222> LOCATION: (1226)..(1226)
<223> OTHER INFORMATION: point mutation in alx8 (g1226a)
<220> FEATURE:
<221> NAME/KEY: misc_feature
<222> LOCATION: (1989)..(1991)
<223> OTHER INFORMATION: Stop codon

<400> SEQUENCE: 1

```
gacatatatt tatcttcttg aaaagcgaat gatgtctata aattgttttc gaacagcgaa      60
ggctccgctt caatcatttg tagcagtaag aacgaattcg agacctagaa attcatcgaa     120
ccgtctcgtt tctgtattcg gacgcaagtc ttcttctcct tcatttgtta ctctcagagt     180
tgtttcatcg atggcttacg agaaagagct tgatgctgct aagaaagctg cttcactcgc     240
tgctcgtctc tgtcaggtta gggttttttc gattcaatca tgacccatag attctaaagt     300
ttgattcttt aagaaaccca ttttgtaaat cttccaaatt tcgtttaaca ttttgtgttt     360
attgtgcatt gcatctgtaa ttgggaatag attctagtga tatagtgtaa tggtcctcta     420
catacgaagc tcgtgtaaat cttgatcaa atcttatct ttgtgttttg gtttgtttc       480
agaaagttca aaggctttg ttgcaatcag atgtgcaatc aaaatctgat aaaagtccag     540
tgaccgttgc tgattatggt tagttttgtta tacctgtccc tgattagaaa aagctcttct     600
ctttgaatgt tactgagatt gttaggaaat cacttaattt gatctgtctt gtgttgaatt    660
tcaggttcac aagcagttgt tagttttagtc ttagaaaaag agctcagttc tgaacccttt    720
tcattggtgg ctgaagaggt gaaactgctt aataaatcct tgttagatgt ctcacacttt    780
acttatcttt gagtttgtgt ttatggactc acattgtcta aaatgatcta tataggactc    840
aggcgatcta cgcaaggatg gttctcagga tactctggag cgcatcacaa aactcgtgaa    900
cgacactttg gctaccgagg aatcgtttaa tggctctact tgtctactg atgatctact     960
tagagccatt gactgtggaa catctgaagg tggtccaaat ggtcgacact gggtcttgga   1020
tccaattgat ggcactaaag ggtacgtttt aaaactaact agcctaaagt caaatcttct   1080
tatttcagag aaaatgtaaa tttgatagaa tgttgagtca gatgttatgt tcctgacact   1140
gagcattttc atgatttag atttctgagg ggagatcaat acgcagtagc actaggattg    1200
ctcgaggaag ggaaagtagt tttaggtgtg cttgcttgtc caaacttgcc gttagcatcc    1260
atagcaggaa acaacaagaa caaatcttcg tcagacgaaa ttggatgcct cttctttgct   1320
acaattggtt cagggacata tatgcagctc ctagattcaa atcttctcc tgtaaaagtg    1380
caagtctcta gtgttgagaa tcctgaagag gcatcgttct tcgagtcatt cgaaggagct   1440
cactctctac atgacttatc cagctccatt gccaatgtaa attgcttctt tccttccatg   1500
tgattccagc taatagctaa ctaattttcc tcatccattt gatcatgttc tatgttgtaa   1560
tatacagaaa ctcggtgtca aagctccacc agtccgtatt gatagccaag caaagtatgg   1620
agctttatca agaggagatg gagctatata cttacggttt cctcataaag gataccgcga   1680
```

-continued

```
aaagatttgg gaccatgtcg ctggtgctat agttgttaca ggtaacatta aagcttactc    1740
tctatgaagc taattttata gtgtcgacat gcggatgtaa atagataagg aatgcaaggt    1800
tgattcttct ttttggtgca gaggcgggtg gaatagtgac agatgcagca ggaaagccac    1860
tggatttctc gaaagggaag tatcttgatt tggacacagg cattatcgtt gctaacgaga    1920
agctaatgcc tctgcttttg aaagcagttc gtgactccat agctgagcaa gagaaagctt    1980
cagctctctg atttgttttt ttctctcgta cgttctttgt ttctctgtaa ctgttgtttc    2040
attttctttc accgaatttc accagtgaga atttcttcca ttttcgaaaa agaaataaaa    2100
atgaaattct gttttgggct aa                                             2122
```

<210> SEQ ID NO 2
<211> LENGTH: 407
<212> TYPE: PRT
<213> ORGANISM: Arabidopsis sp.
<220> FEATURE:
<221> NAME/KEY: misc_feature
<222> LOCATION: (217)..(217)
<223> OTHER INFORMATION: point mutation in alx8 (G217D)

<400> SEQUENCE: 2

```
Met Met Ser Ile Asn Cys Phe Arg Thr Ala Lys Ala Pro Leu Gln Ser
1               5                   10                  15

Phe Val Ala Val Arg Thr Asn Ser Arg Pro Arg Asn Ser Ser Asn Arg
            20                  25                  30

Leu Val Ser Val Phe Gly Arg Lys Ser Ser Pro Ser Phe Val Thr
        35                  40                  45

Leu Arg Val Val Ser Ser Met Ala Tyr Glu Lys Glu Leu Asp Ala Ala
    50                  55                  60

Lys Lys Ala Ala Ser Leu Ala Ala Arg Leu Cys Gln Lys Val Gln Lys
65                  70                  75                  80

Ala Leu Leu Gln Ser Asp Val Gln Ser Lys Ser Asp Lys Ser Pro Val
                85                  90                  95

Thr Val Ala Asp Tyr Gly Ser Gln Ala Val Val Ser Leu Val Leu Glu
            100                 105                 110

Lys Glu Leu Ser Ser Glu Pro Phe Ser Leu Val Ala Glu Glu Asp Ser
        115                 120                 125

Gly Asp Leu Arg Lys Asp Gly Ser Gln Asp Thr Leu Glu Arg Ile Thr
    130                 135                 140

Lys Leu Val Asn Asp Thr Leu Ala Thr Glu Glu Ser Phe Asn Gly Ser
145                 150                 155                 160

Thr Leu Ser Thr Asp Asp Leu Leu Arg Ala Ile Asp Cys Gly Thr Ser
                165                 170                 175

Glu Gly Gly Pro Asn Gly Arg His Trp Val Leu Asp Pro Ile Asp Gly
            180                 185                 190

Thr Lys Gly Phe Leu Arg Gly Asp Gln Tyr Ala Val Ala Leu Gly Leu
        195                 200                 205

Leu Glu Glu Gly Lys Val Val Leu Gly Val Leu Ala Cys Pro Asn Leu
    210                 215                 220

Pro Leu Ala Ser Ile Ala Gly Asn Asn Lys Asn Lys Ser Ser Ser Asp
225                 230                 235                 240

Glu Ile Gly Cys Leu Phe Phe Ala Thr Ile Gly Ser Gly Thr Tyr Met
                245                 250                 255

Gln Leu Leu Asp Ser Lys Ser Ser Pro Val Lys Val Gln Val Ser Ser
            260                 265                 270

Val Glu Asn Pro Glu Glu Ala Ser Phe Phe Glu Ser Phe Glu Gly Ala
```

```
                    275                 280                 285
His Ser Leu His Asp Leu Ser Ser Ile Ala Asn Lys Leu Gly Val
        290                 295                 300

Lys Ala Pro Pro Val Arg Ile Asp Ser Gln Ala Lys Tyr Gly Ala Leu
305                 310                 315                 320

Ser Arg Gly Asp Gly Ala Ile Tyr Leu Arg Phe Pro His Lys Gly Tyr
                325                 330                 335

Arg Glu Lys Ile Trp Asp His Val Ala Gly Ala Ile Val Val Thr Glu
            340                 345                 350

Ala Gly Gly Ile Val Thr Asp Ala Ala Gly Lys Pro Leu Asp Phe Ser
        355                 360                 365

Lys Gly Lys Tyr Leu Asp Leu Asp Thr Gly Ile Ile Val Ala Asn Glu
    370                 375                 380

Lys Leu Met Pro Leu Leu Leu Lys Ala Val Arg Asp Ser Ile Ala Glu
385                 390                 395                 400

Gln Glu Lys Ala Ser Ala Leu
                405

<210> SEQ ID NO 3
<211> LENGTH: 2122
<212> TYPE: DNA
<213> ORGANISM: Arabidopsis sp.
<220> FEATURE:
<221> NAME/KEY: misc_feature
<222> LOCATION: (734)..(735)
<223> OTHER INFORMATION: insertion site for SALK_020882 T-DNA

<400> SEQUENCE: 3
gacatatatt tatcttcttg aaaagcgaat gatgtctata aattgttttc gaacagcgaa      60
ggctccgctt caatcatttg tagcagtaag aacgaattcg agacctagaa attcatcgaa     120
ccgtctcgtt tctgtattcg gacgcaagtc ttcttctcct tcatttgtta ctctcagagt     180
tgtttcatcg atggcttacg agaaagagct tgatgctgct aagaaagctg cttcactcgc     240
tgctcgtctc tgtcaggtta gggttttttc gattcaatca tgacccatag attctaaagt     300
ttgattcttt aagaaaccca ttttgtaaat cttccaaatt tcgtttaaca ttttgtgttt     360
attgtgcatt gcatctgtaa ttgggaatag attctagtga tatagtgtaa tggtcctcta     420
catacgaagc tcgtgtaaat ctttgatcaa aatcttatct ttgtgttttg ggtttgtttc     480
agaaagttca aaaggctttg ttgcaatcag atgtgcaatc aaaatctgat aaaagtccag     540
tgaccgttgc tgattatggt tagtttgtta tacctgtccc tgattagaaa aagctcttct     600
ctttgaatgt tactgagatt gttaggaaat cacttaattt gatctgtctt gtgttgaatt     660
tcaggttcac aagcagttgt tagtttagtc ttagaaaaag agctcagttc tgaacccttt     720
tcattggtgg ctgaagaggt gaaactgctt aataaatcct tgttagatgt ctcacacttt     780
acttatcttt gagtttgtgt ttatggactc acattgtcta aaatgatcta tataggactc     840
aggcgatcta cgcaaggatg gttctcagga tactctggag cgcatcacaa aactcgtgaa     900
cgacactttg ctaccgagg aatcgtttaa tggctctact tgtctactg atgatctact      960 tagagccatt gactgtggaa catctgaagg tggtccaaat ggtcgacact gggtcttgga    1020
tccaattgat ggcactaaag ggtacgtttt aaaactaact agcctaaagt caaatcttct    1080
tatttcagag aaaatgtaaa tttgatagaa tgttgagtca gatgttatgt tcctgacact    1140
gagcattttc atgatttag atttctgagg ggagatcaat acgcagtagc actaggattg     1200
ctcgaggaag ggaaagtagt tttaggtgtg cttgcttgtc caaacttgcc gttagcatcc    1260
```

| | |
|---|---|
| atagcaggaa acaacaagaa caaatcttcg tcagacgaaa ttggatgcct cttctttgct | 1320 |
| acaattggtt cagggacata tatgcagctc ctagattcaa atcttctcc tgtaaaagtg | 1380 |
| caagtctcta gtgttgagaa tcctgaagag gcatcgttct tcgagtcatt cgaaggagct | 1440 |
| cactctctac atgacttatc cagctccatt gccaatgtaa attgcttctt ccttccatg | 1500 |
| tgattccagc taatagctaa ctaattttcc tcatccattt gatcatgttc tatgttgtaa | 1560 |
| tatacagaaa ctcggtgtca aagctccacc agtccgtatt gatagccaag caaagtatgg | 1620 |
| agctttatca agaggagatg gagctatata cttacggttt cctcataaag gataccgcga | 1680 |
| aaagatttgg gaccatgtcg ctggtgctat agttgttaca ggtaacatta agcttactc | 1740 |
| tctatgaagc taattttata gtgtcgacat gcggatgtaa atagataagg aatgcaaggt | 1800 |
| tgattcttct ttttggtgca gaggcgggtg gaatagtgac agatgcagca ggaaagccac | 1860 |
| tggattctc gaaagggaag tatcttgatt tggacacagg cattatcgtt gctaacgaga | 1920 |
| agctaatgcc tctgcttttg aaagcagttc gtgactccat agctgagcaa gagaaagctt | 1980 |
| cagctctctg atttgttttt ttctctcgta cgttctttgt ttctctgtaa ctgttgtttc | 2040 |
| attttctttc accgaatttc accagtgaga atttcttcca ttttcgaaaa agaaataaaa | 2100 |
| atgaaattct gttttgggct aa | 2122 |

```
<210> SEQ ID NO 4
<211> LENGTH: 2111
<212> TYPE: DNA
<213> ORGANISM: Arabidopsis sp.
<220> FEATURE:
<221> NAME/KEY: misc_feature
<222> LOCATION: (734)..(735)
<223> OTHER INFORMATION: insertion site of SALK_020882 T-DNA

<400> SEQUENCE: 4
```

| | |
|---|---|
| gacatatatt tatcttcttg aaaagcgaat gatgtctata aattgttttc gaacagcgaa | 60 |
| ggctccgctt caatcatttg tagcagtaag aacgaattcg agacctagaa attcatcgaa | 120 |
| ccgtctcgtt tctgtattcg gacgcaagtc ttcttctcct tcatttgtta ctctcagagt | 180 |
| tgtttcatcg atggcttacg agaaagagct tgatgctgct aagaaagctg cttcactcgc | 240 |
| tgctcgtctc tgtcaggtta gggttttttc gattcaatca tgacccatag attctaaagt | 300 |
| ttgattcttt aagaaaccca ttttgtaaat cttccaaatt tcgtttaaca ttttgtgttt | 360 |
| attgtgcatt gcatctgtaa ttgggaatag attctagtga tatagtgtaa tggtcctcta | 420 |
| catacgaagc tcgtgtaaat ctttgatcaa aatcttatct ttgtgttttg ggtttgtttc | 480 |
| agaaagttca aaaggctttg ttgcaatcag atgtgcaatc aaaatctgat aaaagtccag | 540 |
| tgaccgttgc tgattatggt tagtttgtta tacctgtccc tgattagaaa aagctcttct | 600 |
| ctttgaatgt tactgagatt gttaggaaat cacttaattt gatctgtctt gtgttgaatt | 660 |
| tcaggttcac aagcagttgt tagtttagtc ttagaaaaag agctcagttc tgaacccttt | 720 |
| tcattggtgg ctgatgctta ataaatcctt gttagatgtc tcacacttta cttatctttg | 780 |
| agtttgtgtt tatggactca cattgtctaa aatgatctat ataggactca ggcgatctac | 840 |
| gcaaggatgg ttctcaggat actctggagc gcatcacaaa actcgtgaac gacactttgg | 900 |
| ctaccgagga atcgttttaat ggctctactt tgtctactga tgatctactt agagccattg | 960 |
| actgtggaac atctgaaggt ggtccaaatg gtcgacactg ggtcttggat ccaattgatg | 1020 |
| gcactaaagg gtacgtttta aaactaacta gcctaaagtc aaatcttctt atttcagaga | 1080 |
| aaatgtaaat ttgatagaat gttgagtcag atgttatgtt cctgacactg agcattttca | 1140 |

```
tgattttaga tttctgaggg gagatcaata cgcagtagca ctaggattgc tcgaggaagg    1200
gaaagtagtt ttaggtgtgc ttgcttgtcc aaacttgccg ttagcatcca tagcaggaaa    1260
caacaagaac aaatcttcgt cagacgaaat tggatgcctc ttctttgcta caattggttc    1320
agggacatat atgcagctcc tagattcaaa atcttctcct gtaaaagtgc aagtctctag    1380
tgttgagaat cctgaagagg catcgttctt cgagtcattc gaaggagctc actctctaca    1440
tgacttatcc agctccattg ccaatgtaaa ttgcttcttt ccttccatgt gattccagct    1500
aatagctaac taattttcct catccatttg atcatgttct atgttgtaat atacagaaac    1560
tcggtgtcaa agctccacca gtccgtattg atagccaagc aaagtatgga gctttatcaa    1620
gaggagatgg agctatatac ttacggtttc ctcataaagg ataccgcgaa aagatttggg    1680
accatgtcgc tggtgctata gttgttacag gtaacattaa agcttactct ctatgaagct    1740
aattttatag tgtcgacatg cggatgtaaa tagataagga atgcaaggtt gattcttctt    1800
tttggtgcag aggcgggtgg aatagtgaca gatgcagcag gaaagccact ggatttctcg    1860
aaagggaagt atcttgattt ggacacaggc attatcgttg ctaacgagaa gctaatgcct    1920
ctgcttttga aagcagttcg tgactccata gctgagcaag agaaagcttc agctctctga    1980 tttgttttt tctctcgtac gttctttgtt tctctgtaac tgttgtttca ttttcttca     2040 ccgaatttca ccagtgagaa tttcttccat tttcgaaaaa gaaataaaaa tgaaattctg    2100
ttttgggcta a                                                         2111
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1

<400> SEQUENCE: 5
cggacgcaag tcttcttctc                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplication of SAL1 gene

<400> SEQUENCE: 6
ccaccaatga aagggttca                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 7
ccagtgaccg ttgctgatta                                                20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic -continued primer for amplification of SAL1 gene

<400> SEQUENCE: 8
tgaaaatgct cagtgtcagg a                                        21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 9
acactttggc taccgaggaa                                          20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 10
gtggagcttt gacaccgagt                                          20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 11
ttctcctgta aaagtgcaag tctc                                     24

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 12
tggtgaaatt cggtgaaaga                                          20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 13
tggcttacga gaaagagctt g                                        21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

```
<400> SEQUENCE: 14
agcaaagaag aggcatccaa                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 15 ctgagggag atcaatacgc                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 16
tgctcagcta tggagtcacg                                               20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 17
acacgccatc atcaatcta                                                19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 18
ccctttatac ttagcccaaa                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 19
actcgctgct cgtctctgtc                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for amplification of SAL1 gene

<400> SEQUENCE: 20
```
agaacgatgc ctcttcagga                                          20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      dCAPS primer for alx8 mutant

<400> SEQUENCE: 21
gaggaaggga aagtagttct ag                                       22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      dCAPS primer specific for alx8 mutant

<400> SEQUENCE: 22
tgcactttta caggagaaga                                          20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer specific to T-DNA insert

<400> SEQUENCE: 23
tggttcacgt agtgggccat cg                                       22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer specific to T-DNA insert

<400> SEQUENCE: 24
gcgtggaccg cttgctgcaa ct                                       22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer specific for T-DNA insert

<400> SEQUENCE: 25
ggactcttgt tccaaactgg                                          20

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      primer SacII-SAL1 F1

<400> SEQUENCE: 26
ctccgcggtg gtatggctta cgagaaagag c                             31

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      primer EcoRI-SAL1

<400> SEQUENCE: 27
gctcgaattc tcagagagct gaagctttct c                           31

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer APX2 (At3g09640)

<400> SEQUENCE: 28
ggctgggaca tttgatgtg                                         19

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer APX2 (At3g09640)

<400> SEQUENCE: 29
agggaacagc tccttgatag g                                      21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer APX1 (At1g07890)

<400> SEQUENCE: 30
ccactcgcat ttctccagat                                        20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer APX1 (At1g07890)

<400> SEQUENCE: 31
tcgaaagttc cagcagagtg                                        20

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer sHSP (At2g29500)

<400> SEQUENCE: 32
cctggattga agaaggagga ag                                     22

<210> SEQ ID NO 33

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer sHSP (At2g29500)

<400> SEQUENCE: 33
taggcaccgt aacagtcaac ac                                              22

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer ZAT10 (At1g27730)

<400> SEQUENCE: 34
aggctcttac atcaccaaga ttag                                            24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer ZAT10 (At1g27730)

<400> SEQUENCE: 35
tacacttgta gctcaacttc tcca                                            24

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer cyclophilin (At2g29960)

<400> SEQUENCE: 36
tcttcctctt cggagccata                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer cyclophilin (At2g29960)

<400> SEQUENCE: 37
aagctgggaa tgattcgatg                                                 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer DREB2A (At5g05410)

<400> SEQUENCE: 38
agactatggt tggcccaatg                                                 20

<210> SEQ ID NO 39
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer DREB2A (At5g05410)

<400> SEQUENCE: 39
tcgagctgaa acggaggtat                                                    20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer HSP70 (At3g09440)

<400> SEQUENCE: 40
gctgctattg cttacggtct tg                                                 22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer HSP70 (At3g09440)

<400> SEQUENCE: 41
ctctcgggtt tccactaatg tc                                                 22

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer Fry1-1F

<400> SEQUENCE: 42
aacccatttt gtaaatcttc c                                                  21

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer Fry1-rt2R

<400> SEQUENCE: 43
cagagaaaca aagaacgtac gaga                                               24

<210> SEQ ID NO 44
<211> LENGTH: 358
<212> TYPE: PRT
<213> ORGANISM: Oryza sp.

<400> SEQUENCE: 44

Met Ser Gln Ala Ala Gly Asn Pro Tyr Ala Ala Glu Leu Ala Ala Ala
1               5                   10                  15

Lys Lys Ala Val Thr Leu Ala Ala Arg Leu Cys Gln Ala Val Gln Lys
            20                  25                  30

Asp Ile Leu Gln Ser Gly Val Gln Ser Lys Ala Asp Gln Ser Pro Val
        35                  40                  45

Thr Val Ala Asp Tyr Gly Ser Gln Ile Leu Val Ser Leu Val Leu Lys
    50                  55                  60
```

```
Met Glu Ala Pro Ala Ser Ser Phe Ser Met Val Ala Glu Asp
 65                  70                  75                  80

Ser Glu Glu Leu Arg Lys Glu Gly Ala Glu Ile Leu Glu Asn Ile
                 85                  90                  95

Thr Glu Leu Val Asn Glu Thr Ile Val Asp Asp Gly Thr Tyr Ser Ile
            100                 105                 110

Tyr Phe Ser Lys Glu Gly Ile Leu Ser Ala Ile Asp Asp Gly Lys Ser
             115                 120                 125

Glu Gly Gly Pro Ser Gly Arg His Trp Val Leu Asp Pro Ile Asp Gly
             130                 135                 140

Thr Lys Gly Phe Leu Arg Gly Asp Gln Tyr Ala Ile Ala Leu Ala Leu
145                 150                 155                 160

Leu Asp Glu Gly Lys Val Val Leu Gly Val Leu Ala Cys Pro Asn Leu
                165                 170                 175

Ser Leu Gly Ser Ile Gly Asn Leu Asn Gly Ser Ser Gly Asp Gln
            180                 185                 190

Val Gly Ala Leu Phe Ser Ala Thr Ile Gly Cys Gly Ala Glu Val Glu
            195                 200                 205

Ser Leu Gln Gly Ser Pro Ala Gln Lys Ile Ser Val Cys Ser Ile Asp
210                 215                 220

Asn Pro Val Glu Ala Ser Phe Phe Glu Ser Tyr Glu Gly Ala His Ser
225                 230                 235                 240

Leu Arg Asp Leu Thr Gly Ser Ile Ala Glu Lys Leu Gly Val Gln Ala
            245                 250                 255

Pro Pro Val Arg Ile Asp Ser Gln Ala Lys Tyr Gly Ala Leu Ala Arg
            260                 265                 270

Gly Asp Gly Ala Ile Tyr Leu Arg Phe Pro His Lys Gly Tyr Arg Glu
            275                 280                 285

Lys Ile Trp Asp His Ala Ala Gly Ser Ile Val Val Thr Glu Ala Gly
            290                 295                 300

Gly Leu Val Thr Asp Ala Ser Gly Asn Asp Leu Asp Phe Ser Lys Gly
305                 310                 315                 320

Arg Phe Leu Asp Leu Asp Thr Gly Ile Ile Ala Thr Asn Lys Gln Leu
                325                 330                 335

Met Pro Ser Leu Leu Lys Ala Val Gln Asp Ala Ile Lys Glu Gln Asn
            340                 345                 350

Gln Ala Ala Ser Pro Leu
            355

<210> SEQ ID NO 45
<211> LENGTH: 355
<212> TYPE: PRT
<213> ORGANISM: Zea mays

<400> SEQUENCE: 45

Met Ala Ser Gly Asn Pro Tyr Ala Ala Glu Leu Ala Ala Lys Lys
 1               5                  10                  15

Ala Val Thr Leu Ala Ala Lys Leu Cys Gln Thr Val Gln Gln Asp Ile
             20                  25                  30

Met His Ser Gly Val Gln Ala Lys Ala Asp Lys Ser Pro Val Thr Val
             35                  40                  45

Ala Asp Tyr Gly Ser Gln Ile Leu Val Gly Phe Ser Leu Lys Met Asp
         50                  55                  60

Val Ser Ser Gly Pro Phe Ser Leu Val Ala Glu Glu Ala Leu Asp Glu
 65                  70                  75                  80
```

```
Leu Arg Lys Asp Gly Ala Glu Ile Leu Glu Asp Ile Thr Asp Leu
                85                  90                  95

Val Asn Glu Thr Ile Phe Asp Gly Ser Tyr Asn Ile Ser Phe Thr
            100                 105                 110

Lys Glu Gly Ile Leu Ser Ala Ile Asp Asp Gly Lys Ser Glu Gly Gly
        115                 120                 125

Pro Ser Gly Arg His Trp Val Leu Asp Pro Ile Asp Gly Thr Lys Gly
130                 135                 140

Phe Leu Arg Gly Asp Gln Tyr Ala Ile Ala Leu Ala Leu Leu Asp Glu
145                 150                 155                 160

Gly Lys Val Val Leu Gly Val Leu Ala Cys Pro Asn Leu Pro Leu Ser
                165                 170                 175

Ser Ile Asn Asn Ile Asn Gly Asn Ser Ser Gly Asp Lys Val Gly Ala
            180                 185                 190

Leu Phe Ser Ala Thr Ile Gly Cys Gly Ala Gln Val Glu Ser Leu Asp
        195                 200                 205

Gly Ser Pro Pro Gln Lys Ile Ser Val Cys Ser Ile Asp Asn Pro Val
    210                 215                 220

Asn Ala Ser Phe Phe Glu Ser Tyr Glu Ser Ala His Ser Met His Asp
225                 230                 235                 240

Leu Thr Arg Ser Ile Ala Glu Lys Leu Gly Val Gln Ala Pro Pro Val
                245                 250                 255

Arg Ile Asp Ser Gln Ala Lys Tyr Gly Ala Leu Ala Arg Gly Asp Gly
            260                 265                 270

Ala Ile Tyr Leu Arg Phe Pro His Lys Gly Tyr Arg Glu Lys Ile Trp
        275                 280                 285

Asp His Ala Gly Gly Ser Ile Val Val Thr Glu Ala Gly Gly Ile Val
    290                 295                 300

Thr Asp Ala Ala Gly Lys Asp Leu Asp Phe Ser Lys Gly Arg Phe Leu
305                 310                 315                 320

Asp Leu Asp Thr Gly Ile Ile Ala Thr Asn Lys Glu Leu Met Pro Ser
                325                 330                 335

Leu Leu Lys Ala Val Gln Glu Ala Ile Lys Glu Thr Asn Gln Ala Ala
            340                 345                 350

Ser Leu Leu
        355

<210> SEQ ID NO 46
<211> LENGTH: 353
<212> TYPE: PRT
<213> ORGANISM: Arabidopsis thaliana

<400> SEQUENCE: 46

Met Ala Tyr Glu Lys Glu Leu Asp Ala Ala Lys Lys Ala Ala Ser Leu
1               5                   10                  15

Ala Ala Arg Leu Cys Gln Lys Val Gln Lys Ala Leu Leu Gln Ser Asp
            20                  25                  30

Val Gln Ser Lys Ser Asp Lys Ser Pro Val Thr Val Ala Asp Tyr Gly
        35                  40                  45

Ser Gln Ala Val Val Ser Leu Val Leu Glu Lys Glu Leu Ser Ser Glu
    50                  55                  60

Pro Phe Ser Leu Val Ala Glu Glu Asp Ser Gly Asp Leu Arg Lys Asp
65                  70                  75                  80

Gly Ser Gln Asp Thr Leu Glu Arg Ile Thr Lys Leu Val Asn Asp Thr
                85                  90                  95
```

```
Leu Ala Thr Glu Glu Ser Phe Asn Gly Ser Thr Leu Ser Thr Asp Asp
            100                 105                 110
Leu Leu Arg Ala Ile Asp Cys Gly Thr Ser Glu Gly Gly Pro Asn Gly
        115                 120                 125
Arg His Trp Val Leu Asp Pro Ile Asp Gly Thr Lys Gly Phe Leu Arg
    130                 135                 140
Gly Asp Gln Tyr Ala Val Ala Leu Gly Leu Leu Glu Glu Gly Lys Val
145                 150                 155                 160
Val Leu Gly Val Leu Ala Cys Pro Asn Leu Pro Leu Ala Ser Ile Ala
                165                 170                 175
Gly Asn Asn Lys Asn Lys Ser Ser Asp Glu Ile Gly Cys Leu Phe
            180                 185                 190
Phe Ala Thr Ile Gly Ser Gly Thr Tyr Met Gln Leu Leu Asp Ser Lys
        195                 200                 205
Ser Ser Pro Val Lys Val Gln Val Ser Ser Val Glu Asn Pro Glu Glu
    210                 215                 220
Ala Ser Phe Phe Glu Ser Phe Glu Gly Ala His Ser Leu His Asp Leu
225                 230                 235                 240
Ser Ser Ser Ile Ala Asn Lys Leu Gly Val Lys Ala Pro Pro Val Arg
                245                 250                 255
Ile Asp Ser Gln Ala Lys Tyr Gly Ala Leu Ser Arg Gly Asp Gly Ala
            260                 265                 270
Ile Tyr Leu Arg Phe Pro His Lys Gly Tyr Arg Glu Lys Ile Trp Asp
        275                 280                 285
His Val Ala Gly Ala Ile Val Val Thr Glu Ala Gly Gly Ile Val Thr
    290                 295                 300
Asp Ala Ala Gly Lys Pro Leu Asp Phe Ser Lys Gly Lys Tyr Leu Asp
305                 310                 315                 320
Leu Asp Thr Gly Ile Ile Val Ala Asn Glu Lys Leu Met Pro Leu Leu
                325                 330                 335
Leu Lys Ala Val Arg Asp Ser Ile Ala Glu Gln Glu Lys Ala Ser Ala
            340                 345                 350
Leu

<210> SEQ ID NO 47
<211> LENGTH: 1417
<212> TYPE: DNA
<213> ORGANISM: Picea sp.

<400> SEQUENCE: 47
ggttctctgc gacttgtgtg tataagtcta taacatcaat caatggcgtg gtcgagccga      60
ttctcatttc aatttacgag gacttctagt gccacctcat ttgttttcct tccaactaca     120
accctacctc tacagataca tttccccagc gtgagtgcga ggaggagcat caccaccaag     180
acaacaagag cgaaaatgga catcggtgca tacgaacaag atcttgccat tgcaatcaag     240
gccgcctctc tcgcagctcg tctatgccag tcggtgcaaa agagcctttt acaaacagat     300
actcaagcca agatggacag ttctcctgtc actgttgcgg attatggttc tcaggcttta     360
gttagctttg tgcttgagag ggaactacaa tcgggagtgt tttccatggt tgcagaagag     420
gattcaggag atttacagaa gaatgatgca caagatatgt ggaacgcat acagcactt      480
gtaaatgaaa ccatttctaa tgatagtgcc tataatattt ctccattaac aacaggagat     540
gtacttgcag caatagatag aggcaaatct gaaggagggc acatggtcg gcactgggtt      600
ttggacccca tgatgggac aaaaggattt cttagaggag accaatatgc tgtagccttg     660
```

```
ggcttattgg atgaaggaga agttattttg ggtgtgctgg cctgcccaaa tttgccctgg      720
acatcagtta gcatcagtgc ccgcccttca aatgatccaa ttggttgcct ttttctgca       780 agaaaagtgc cgttgaaaag tctgaagatg catctttctt tgaatcatat gaggcagcac      840
attccatgca tgacttgaca gctacaatag caaagatcct gggtgtaaaa gcaccaccag      900
ttagaataga tagtcaggca aaatatgag caatggcaag gggtgatgga gcaatatatc       960
ttcgctttcc tcgtccaggc tatcgtgaaa agatttggga tcatgcagct ggttgcatcg     1020
taatccaaga ggctggtggt gttgtggttg atgctgctgg gaaacctctt gatttctcac     1080
aggggaggta tctggatgtg aaagggggta taattgcaac caatgccaaa ctgatgccat     1140
tgcttcttaa tgcagtgcaa gctgctctga aggaagaagg aaatgttcga aaggctggtt     1200
ccttgtagca ccattcattt attgaaccta attagggatg aagttggaa cttatgctga      1260 tgaaataaaa caattctatt tgcacaaggt ccttccttta agagatataa ctgagtgtcg     1320
tggtaggtgt gtcaactctc tggctctagt cctggccaca tttgcagtga tagacaataa    1380
gttgaaaacg gaagtacatt aatttccttt aattttc                             1417
```

<210> SEQ ID NO 48
<211> LENGTH: 1070
<212> TYPE: DNA
<213> ORGANISM: Pinus sp.

<400> SEQUENCE: 48

```
caagagtgaa gatggagaac agggcatacg aacaagatct tgccattgca atcagggctg       60
cctctctggc agctcgtcta tgccagtcag tgcagaagag ccttttacaa acagatactc      120
aagccaagac ggacagttct cctgtcactg ttgcagatta cggttctcag gctttagtta      180
gctttgtact tgaaagggaa ttaccctcgg gattgttttc cttggttgca gaagaggatt      240
caggagattt acagaagaat gatgcacaag atatggtgga acgcattaca gcacttgtaa      300
atgaaaccat ttctaatgat ggtacctatg atatttctcc attaacaaca ggagatgtac      360
ttgcagcgat agatagaggt aaatctgaag gagggcccca tggtcggcat tgggttttag      420
accccattga tgggacaaag ggatttctta ggggagacca atatgctgta gccttaggct      480
tattggatga aggagaagtt attttgggtg tgctggcctg cccaaatttg ccctggacat      540
cagttagcat cagtgctcgc ccttcaaatg atccaattgg ttgtcttttt tctgcaataa      600
aaggagctgg aactactgtg caatcattgg atggttctat acaacctaaa agggtttatg      660
taagtgccat agaaaagtct gaagaagcat cttttttga atcatcgag gcagcacatt        720 ccatgcatga cttgacggct acaatagcga agatcctggg tgtaaaagca ccccagtta      780 gaatagatag tcaggcaaaa tatggtgcaa tggcaagggg tgatggagca atatattc       840 gcttcccttg tccaggctat cgtgaaaaga tttgggatca tgcagctggt tgtattgtaa      900
tccaagaaaa ttcatccgaa ttgcagaggc tggtggtgtt gtagttgatg ctgctggaaa      960
acctcttgat ttctcacggg ggaggtatct ggatgtggaa aagggtataa ttgcaaccaa     1020
tgccaaactg atgccattgc tttttaatgc agtgcaagct gctctcaagg                1070
```

<210> SEQ ID NO 49
<211> LENGTH: 1544
<212> TYPE: DNA
<213> ORGANISM: Medicago sp.

<400> SEQUENCE: 49

```
tggggacgca gagtttgttg ggaggaacaa gaacggtagt agcaataagg gattgttgcg       60
```

```
aatccataaa tacaataata ataatcagga aaaaatccac caccgtctct ggtttctcat      120
tatcatcatc aacgacaaga agatcctctt cattgtattg tcgtcgttgg tcaccattaa      180
cgacaatact ttcttcttct tctttaatgt cttcttacga gaaggaactc gctgctgcta      240
agaaagctgc cactctcgct gctcgtcttt gccagaaagt acaaaaagct cttcttcaat      300
ctgatgttca ctctaaatct gacaaaactc ctgtcactgt tgctgattat ggttcgcaga      360
tcttggtcag cttgatgctt cagagagagc ttccttctga accattttca ttagtagctg      420
aggaggattc aggggatctt cgtaaggaaa gtggccaaga tacattgaag cgcattacag      480
atcttgtcaa tgatactctt gttaatgaag gatcacataa catttctgct ttaacaacag      540
atgacgtgct taatgccatt gataatggta agtccgaagg tggttccatt gggcggcact      600
gggttttgga tccgatagat ggtactaaag gttttgtaag aggagaccaa tatgccatag      660
cattagctct gctagatgaa gggaaagttg tattgggtgt cttggcttgt ccaaatcttc      720
cgctgggaac cattggcccg aatcaaccgc attcttcttc taatgaagtt gggtgtcttt      780 tcttttgccaa agttggcaat ggaacatata tgcaagcatt ggatggtact acacaaacta      840
aggtgaatgt tagtactgtt gacaatccag aagaagcatc atttttttgaa tcttatgaag      900 cagcacactc ctcacatgac ttgtctagca ctattgcagt aaaactcggc gtcaaagcac      960
cgccagtcag aattgacagc caggcaaaat acggagctct atccagagga gatgggggcta     1020 tatatttgcg tttccccaac aaaggatacc gtgaaaaaat atgggatcat gctgctggtt     1080
gtattgttgt gagtgaagct ggaggtattg tctcagatgc tgccggaaac cctttggact     1140
tctcaaaagg aaagttcctt gatgttgata ctggtattat tgttacaaac cagaacttga     1200
tgccttcgct tttgagagca gttaaagaat cactcaatga gaaagcatca tccttgtaat     1260
atctgtcaag tgtatgattc tactactgag cttcctcatt ttgttgtcag ccagttatat     1320
gaaccttcct ctcaattgtg ctacatttca tacgcgatct gatgaagcta agcatatgac     1380
tggacttcct ccaacacttt atttaaatca tatgcctgtt ctgcttttttg cgtgtactgt     1440 cttcaagatt cttgtaattt aagcttgagt tgtaggtcct tttttcttctt gcaagtactt     1500 ttttcctccc aactttcttt tctattaata gatattttta tttc                       1544

<210> SEQ ID NO 50
<211> LENGTH: 892
<212> TYPE: DNA
<213> ORGANISM: Lotus japonicus
<220> FEATURE:
<221> NAME/KEY: modified_base
<222> LOCATION: (25)..(25)
<223> OTHER INFORMATION: a, c, t or g

<400> SEQUENCE: 50
agaatctgga aaacaaccat caccngttgt gatctttcat caaggggaag aagaagaaga       60
ccagtttcct tgtcttgttg ttgttcatca cttttcttcaa tgccttacga gaaggagctc      120
gctgctgcca agaaagcagc cactctcgct gctcgtctct gtcagaaagt acaaaaggct      180
cttctgcaat ccgatgtcca ctcaaaatca gacaaaagtc ctgtcaccgt cgctgattat      240
ggttcacaaa ccttggtcag cttaatactc gagagagaac ttccttctga accattttca      300
ttagtagctg aggaggattc aggcgatctg cgtgaggaaa gtggccacga tactttgaag      360
cggattacag aacttgtcaa tgatactctt gctaatgaag gatcaaatag cttttctact      420
ttaacaacag acaatgtgct tagagccatt gacaatggta agtctgaagg tggctctgtt      480
ggacggcact gggttttgga tccaatagat ggcactaaag ggtttgtaag aggagaccaa      540
```

```
tacgctattg cattagcttt gctaaatgaa ggaaaagttg tattgggtgt cttggcttgc    600
ccgaatcttc cactggcatc cattgcctgt aatcagcagc attctacttc taatgaagtt    660
ggttgtcttt tctttgctaa agttggcgat ggaacattta tgcaggcaat ggatggttct    720
acacagacta gggtgcatgt cagtgctatt gataatccag aagaggcatc attttttgag    780
tcttttgaag cagcgcactc cttacatgac ttgtctagct ccattgcaga aaaacttggt    840
gttaaggcac cgccagtcag aattgacagc caagcaaaat atggagctct gt            892
```

```
<210> SEQ ID NO 51
<211> LENGTH: 1514
<212> TYPE: DNA
<213> ORGANISM: Glycine max
<400> SEQUENCE: 51
gaaaaagatg ggtactcaaa caacactttg gtgtagagca agaactacta taagtgtagg     60
aggtgattgg aagttgttcg aatccagaat ccgaaaaaag ggcaccaccg tgtcaacaag    120
tagaagcaga agctgttttt gttcttcgcc gctgacacta atcgtttctt caatgcctta    180
cgagaaggaa ttcgccgctg caaaaaaagc agccactctc gctgctcgtc tctgcaagaa    240
agtacagaag gctcttctgc aatccgatgt gcactcaaag tcagacaaaa gtcctgtcac    300
agtggctgat tatggttcac aagcattggt cagctttata cttgagagag aacttccttc    360
tgaaccattt tcattagtag ctgaggagga ttcaggtgat cttcgtaagg agagtggtca    420
ggatacgctg aagcgcatta cagaacttgt caatgatacc cttgctagtg aaggatcaaa    480
tagcttttct actttaacaa cagatgatgt gcttgcggcc attgacggtg gtaaatctga    540
aggtggttca gttggacggc actgggtttt ggatccgata gatggtacta aagggtttgt    600
aagaggagat caatatgcta tagcgttagc tttactagat gaaggcaaag ttgtattggg    660
tgtcttggct tgtccaaacc ttccactggc atccattggc tccaatcagc agcattcttc    720
ttcaaatgaa gttggttgtc tcttctttgc taaagttggt gatggaacat atatgcaagc    780
actgggcggt tctacacaaa ctagggtgca tgtctgtgat attgataacc cagaggaagc    840
atcattttc gaatcttttg aagcagcaca ctccttgcat gacttatcta gctcaatcgc    900
agaaaaactt ggtgtcaaag caccaccagt cagaattgat agccaagcaa atatggagc    960
tttgtcaaga ggagatgggg ctatatattt gcgtttccct cacagaggat accgtgaaaa   1020
aatatgggat catgctgctg gcagcattgt tgtgactgaa gctggaggta ttgccatgga   1080
tgctgcgggg aacccttgg acttttcaaa aggaaagttt cttgatgttg tatctggtat   1140
tattgttaca aaccagaaat tgatgccatc acttctgaca gcagttaaag aagcactcaa   1200
tgagaaagca tcatccttgt gatttccatt taagcgaatg attctacaaa tgagcttgct   1260
aacgttgttg tcggctcgtg ttatatgggg ccttcccctc aattgtgcta tatttcattc   1320
tgatgaagtt aaacaaatga tgggacttcc tctgatactt cctttgtagc agcagatttg   1380
tgctctggtt ttttgcagct gctatttct tctccttcta tatacctgtc cttttctctc   1440
cttttctatt aataaacaga gatgagagat cttattttaa acttgtttga taattaattc   1500
ttctagatta cttg                                                      1514
```

```
<210> SEQ ID NO 52
<211> LENGTH: 1252
<212> TYPE: DNA
<213> ORGANISM: Arabidopsis sp.

<400> SEQUENCE: 52
```

```
gacatatatt tatcttcttg aaaagcgaat gatgtctata aattgttttc gaacagcgaa      60
ggctccgctt caatcatttg tagcagtaag aacgaattcg agacctagaa attcatcgaa     120
ccgtctcgtt tctgtattcg gacgcaagtc ttcttctcct tcatttgtta ctctcagagt     180
tgtttcatcg atggcttacg agaaagagct tgatgctgct aagaaagctg cttcactcgc     240
tgctcgtctc tgtcagaaag ttcaaaaggc tttgttgcaa tcagatgtgc aatcaaaatc     300
tgataaaagt ccagtgaccg ttgctgatta tggttcacaa gcagttgtta gtttagtctt     360
agaaaaagag ctcagttctg aaccctttc attggtggct gaagaggact caggcgatct      420
acgcaaggat ggttctcagg atactctgga gcgcatcaca aaactcgtga acgacacttt     480
ggctaccgag gaatcgttta atggctctac tttgtctact gatgatctac ttagagccat     540
tgactgtgga acatctgaag gtggtccaaa tggtcgacac tgggtcttgg atccaattga     600
tggcactaaa ggatttctga ggggagatca atacgcagta gcactaggat tgctcgagga     660
agggaaagta gttttaggtg tgcttgcttg tccaaacttg ccgttagcat ccatagcagg     720
aaacaacaag aacaaatctt cgtcagacga aattggatgc ctcttctttg ctacaattgg     780
ttcagggaca tatatgcagc tcctagattc aaaatcttct cctgtaaaag tgcaagtctc     840
tagtgttgag aatcctgaag aggcatcgtt cttcgagtca ttcgaaggag ctcactctct     900
acatgactta tccagctcca ttgccaataa actcggtgtc aaagctccac cagtccgtat     960
tgatagccaa gcaaagtatg gagctttatc aagaggagat ggagctatat acttacggtt    1020
tcctcataaa ggataccgcg aaaagatttg gaccatgtc gctggtgcta tagttgttac      1080
agaggcgggt ggaatagtga cagatgcagc aggaaagcca ctggatttct cgaaagggaa    1140
gtatcttgat ttggacacag gcattatcgt tgctaacgag aagctaatgc ctctgctttt    1200
gaaagcagtt cgtgactcca tagctgagca agagaaagct tcagctctct ga            1252

<210> SEQ ID NO 53
<211> LENGTH: 764
<212> TYPE: DNA
<213> ORGANISM: Brassica napus

<400> SEQUENCE: 53
ggaacagccc aggcaccgct tcagacattc gcatcagttt cgaaattcag atattcaccg      60
aaccctatcg tttctgtatt gagaaggaag tcgtctcctt catttgttac tctaagagta     120
gtctcatcca tggcttacga gaaagagctt gacgctgcta agaaagctgc ttccctcaca     180
gctcgtctct gtcagaaagt tcaaaaggct tgttgcaat cagatgttca atcaaaatct      240
gataaaagtc cagtcaccgt tgctgattat ggttcacaag cagttgtcag catagtcttg     300
gaaagggaac tcacttctga acccttttca ttggtcgctg aagaggactc agcggatcta     360
cgcaaggatg gttctgagga tattcttcag cgcatcacga aactcgtcaa cgacactttg     420
gctactgagg atctaaccaa agccattgac tctactttaa ccacagatga tctactcaga     480
gccatcgact gtggcacatc tgaaggtggt cctaatggtc gacactgggt cttggatcct     540
atcgatggca ccaaaggatt tttgagggga gatcagtacg cggtagcact aggattactc     600
gaggaaggga agtagtgtt aggtgtgctt gcttgtccaa acttgccatt aacatccata      660
gcaggaaaca agaactcttc ttcttcagac gaaatcggat gcacttcttt gctacgattg     720
gtcagggaca tacatgcagc ccttagactc gaaatcgaac agtc                      764

<210> SEQ ID NO 54
<211> LENGTH: 1340
```

<212> TYPE: DNA
<213> ORGANISM: Populus sp.

<400> SEQUENCE: 54

```
gcgaaatcac aatcacgaaa aacccttttc ttgtttcctc tcccctttta tttttctcta      60
acaaaaccaa aagcaaaacc tcaattccaa gagtattatc ctcttcaatg tcttacaata     120
aagaacttgc tgctgccaag aaagctgtct ctcttgctgc ccgcctctgc cagaagatgc     180
aaaaagctat cttgcaatca gatgtccaat caaaatcaga taaaagtccc gtcactgttg     240
ctgattatgg ctctcaagca ctagttagtt atgctctgca gcgggagctt ccttctgaac     300
tattctcctt agtggcggag gaggattcag aagatctcct caaggatggt ggccaggaaa     360
cactagagcg aatcacaaaa cttgttaacg atattctagc taccgatgga tcatatagtg     420
attctacttt atccactgaa gatattgtca aggccattga ctgtggaaaa tctgaaggtg     480
ttctcgaggg cagacactgg gttctggacc aatagatgg cactaaaggg ttttttaagag    540
gagatcaata tgcaatagct ttagcattgc tagatgaagg acagtagtg ttgggcgtct      600
tggcttgtcc caatcttccg ttaccttcca ttgctggtgg ctctcagcat tctttgcctg     660
gcgaagttgg ttgcctttc ttttctgtag ttggggtgg aacttacatg cagccactgg       720
atagctcttc agcagtgaag gtgcaagtca acgctactga caatcctgaa gaagcatcgc     780
tctttgaatc atatgaagca gcacactcca tgcatgatct atctagttca attgtcaaaa     840
aacttggtgt caaagcacca ccagttagaa ttgatagcca agcaaagtat ggcgctctgt     900
ctagaggaga tggggtcata tacttgcgat tccacataa aggttaccgt gagaaaatat      960
gggatcatgc tgctggatgc atagttgtat cagaagctgg gggactggtc acagatgttg    1020
cggggaaccc cttagatttt tcaagaggaa gatacctgga tcttgacaca ggcatcattg    1080
ttacgaatca gaaactgatg ccattacttt tgaaggcagt tagagaatcc atagaggaga    1140
aagcttcatc attgtgattc tttactgatg aatgaagtca tttccttgc taagtttgtt     1200
agcaactcaa atcagttta cgtgacttga attttccact ctatgtttgc tcaatgtatg     1260
ttgagcatga aactcttgca acttgtgaag ttcaaatgta ttatccgatg cataatagta    1320
gtgtcattct gctaagctac                                                1340
```

<210> SEQ ID NO 55
<211> LENGTH: 1588
<212> TYPE: DNA
<213> ORGANISM: Gossypium sp.

<400> SEQUENCE: 55

```
ggaattttct tacgaaattt ttgaattgca aatttaataa atgtctataa attggttgag      60
atttgtttcc ccctctctta aaaagccccc tcttttcat ctctgtcact tgcctcctcc      120
tcctccttct tcttctgctg tgattgtggc aatgtcttat gataaagaac tggctgctgc     180
aaagaaagca gcctctctcg ctgctcgtct ctgtcagaaa gtacaaaatg ctttgctgca     240
atccgatgtt caatcaaaga atgataaaag tcctgtaact gttgctgatt atggctcaca     300
agcactggtt agttttgtgc tgcagcagga atttcctgat aacttctcat tagttgctga     360
ggaggattct aaagatcttc gcaaggatgg tggccaggaa atagtagagc gcattacaaa     420
acttgtgaac gattctctaa ctattgatgg atcatacaat gttactttat ccacagaaga     480
tattctcagg gccattgaca atggcagatc tgaaggtggt tcccaaggtc gacactgggt     540
tttggatcct atagatggta ctaaaggttt tctgagagga gatcaatatg caatagcatt     600
ggctttgcta gatggaggaa aagttgtcct gggtgtgctg gcttgtccaa atcttccact     660
```

```
aacttccctc agtgatgctg gtcagcattc tccaaataat aaagttggct gccttttctt    720
tgctgtagta ggtggtggaa cttatatgca gccacttgat ggttcttcgg cagtaaaggt    780
gcaagtaagt gctgttgaaa atcctgaaga agcatcattc tttgagtctt atgaagcagc    840
acactccatg catgatttat ctagcttgat tgcccaaaaa ctcggcgtca aagcaccacc    900
ggttagaatt gatagccagg cgaagtatgg tgctctatcc agaggagatg gagccatata    960
tctgcgtctt ccacacaaag ggtatcgaga aaaatatgg gatcatgctg ctgggtgtat    1020
tgttgtgagt gaagctgggg gtgtggtcac agatgctgca gggcagccat tggattttc    1080 aaagggaaag tatcttgatc tggacacagg catcattgtc accaaccaga agttgatgcc    1140
attactgttt aatgcagtta gaaaatctat ccaggagaaa gcttcatctt tgtgattcat    1200
tttagaggca ggcttcatcc tttcctcata acttgctctg ttaagctggt tgaaacttga    1260 ttattttgc cttcaatgct tgaactttta tcattcttct ccccaatgct tataggaaga    1320
ttttcattta gcatgcatga acaagaatgg gaccaataaa tctcatctct acaattaaga    1380
caatgtaatt gtagactaga acttgaaagc atggtcctag gccttgagcc tttctctttg    1440
tcctacctgg cagttgggtt taggtgtaat taattagata aaggaactgt gttgttgaat    1500
acaaacatat tacattatta ctaaacttat ttcatggtaa aacaagtgtg aagtcctctc    1560
cttcccgacc gtttaccttca catggttt                                      1588

<210> SEQ ID NO 56
<211> LENGTH: 1355
<212> TYPE: DNA
<213> ORGANISM: Lycopersicon sp.

<400> SEQUENCE: 56
aaaatacaaa accccacttc ccctttcac ttttgctcac tctaagagca tctaaatcaa     60
ccttaagagc tgttacaatg tcgtatgata aagaacttga tgctgccaag aatgctgctt    120
ctcttgctgc tcgccttgt caaaaagtcc aaaaagcact gttgcaagca gatgttcaat    180
caaagtctga caaatctcca gtgacggtgg ctgattatgg ctcacaggcc gtggttagcg    240
ttgttttgca gaaagagttg tgttctgctt catttcatt agtggctgag gaggactctg    300
gagaccttcg taatgaagag ggaaaatcaa cattacagcg tatcatgaag cttgtcaatg    360
aaacacttgc tagtgatgga acatatggta ctgccccatt atctgaagaa gatgtccttg    420
ctgccattga tagtggtaga tctgaagggg gtccttctgg tcagcactgg gtgttggatc    480
ctattgatgg tactaaaggg tttctaaggg gagaccaata tgcaattgca ttgggattgc    540
tagatgaagg gaaggtggtt ttgggcgtct tagcctgtcc aaatcttcca ttatcttctc    600
ttgcctccca caatctacag gatgatcaag acaaagttgg ttgccttttt tatgcccaag    660
ttggttctgg aacttatatg cagtctcttg atggctctac accaataaag gtgcatgtaa    720
ctgatttaga caaccctgaa gaggcatctt tttttgaatc ttttgaagca gcacattctt    780
tgcatgacct atctagtttg atagcaaaga aacttggtgt aaaagccccc ccagttcgaa    840
tagacagcca ggcaaagtat ggtgctttgt cccgtggaga tggagcaata tatctgcggt    900
ttcctcataa aggctaccgc gagaagatat gggatcatgc tgctggatat ctcgttgttg    960
cagaagctgg aggtgttgtc tcagatgctg caggaaaccc tttggacttc tccaagggaa    1020
gataccttga tttacacgaa ggcataatcg ttaccaatca aaagctgatg cctgctctcc    1080
tcaaggctgt taaagaatct ttgaatgaga agcttcatc cttgtgatga tcaaaccaat    1140
aacaatacgc tgcagctatc ttattgtagt tcccagaatg gtacttgcag ctgctcattt    1200
```

```
tcacctgttc ttctccttct acacatttct gatatcactt tttagctctt tgattgtcat      1260
ctcaactcag ctttgataaa cattttgttg ttctctggtt atgtcaactc aactttgatt      1320
aaacattata tatttctctt ggtatgtttt ttttt                                 1355

<210> SEQ ID NO 57
<211> LENGTH: 1058
<212> TYPE: DNA
<213> ORGANISM: Solanum sp.
<220> FEATURE:
<221> NAME/KEY: modified_base
<222> LOCATION: (970)..(970)
<223> OTHER INFORMATION: a, c, t or g

<400> SEQUENCE: 57
gctttcacat tatcatctag gactataaat tccttgacac aaaaaacccct gccattgtta      60 acaaaaaata caaaacccca tttcccctttt tcactttgtc tcactctaag agcatctaaa     120
tcaaccttaa gagctgtttc aatgtcgtat gataaagaac ttgatgctgc caagaatgct     180
gcttctcttg ctgctcgcct ctgtcaaaaa gtccaaaaag cactgttgca agcagatgtt     240
caatcaaagt ctgacaaatc tcctgtgacg gtggctgatt atggctcaca ggccgtggtt     300
agcgttgttt tgcagaaaga gttgggttct gcttcatttt cattagtggc tgaggaggac     360
tctggagatc ttcgtaatga aaagggaaaa gcaacattac agcgtatcat gaagcttgtc     420
aatgaaacac ttgctagtga tggaacatat ggtactgccc cattatctga agaagatgtc     480
cttgctgcca ttgatagtgg tagatctgaa ggggtccctt ctggtcagca ctgggtgttg     540
gatcctattg atggtactaa agggtttctg aggggagacc aatatgcaat tgcattggga     600
ttgctagatg aagggaaggt ggtttttgggc gtcttatcct gtccaaatct tccattatct     660
tctcttgcct cccacaatct acaggatgat caagacaaag ttggttgcct tttttatgcc     720
caagttggtt ctggaactta tatgcagtct cttgatggct ctacaccaat aaaggtgcat     780
gtaactgatt tagacaaccc cttgaagagg catctttttt tgaaatcttt tgaaagcaga     840
cacatttctt tggcatgacc taatctagtt tggatagcaa agaaacctttg ggtggtaaaa     900 gccccgcagg tcgatataca cgccgggcaa agaggggctt cgccccggcg aaaatggcac     960
aaataatctn ggggtcccca aaagggacc aggaaaaata tcgggaccac gggggagact    1020
cctggggcac acagcggggg gtccacacaa ggcgacag                          1058

<210> SEQ ID NO 58
<211> LENGTH: 1196
<212> TYPE: DNA
<213> ORGANISM: Allium sp.

<400> SEQUENCE: 58
caatttgcaa aagtccctcc tcgtctacac tgtgctaacc tatcccccctt aatctcgatt      60 aaatgttccc caattaatta tctccctgtc ttttctccca ccaaatctag ttcactttct     120
tgctcctccg tatctcaatt aaaagccaag actgaatcta gatctttatc catttctgcc     180
atggcttcgt acgagaaaga tcttaccgct gccaagaagg ctgcttcact ggctgctcgt     240
ctatgccaaa cggtgcagaa ggcgatattg cagtcggatg tgcactcaaa agcagataag     300
agtcctgtta ctgtggccga ttatggttcc caagtattgg tcagtcttgt tttgagaaaa     360
gaacttcctt ttgattcctt ttcaatggtt gctgaagagg attcaggaga cttgcgaaca     420
gatgctggtc aagaaacatt gaaacgtatt acgaagcttg taaatgacac tctttcttct     480
gatagtactt ataatgatat aatttttatct gaagaagata tacttgtcgc tattgatact     540
```

-continued

```
ggaaaatctg aaggaggccc tcatgggcga cactgggtac tggatcctat agatggcacc    600
aaagggtttg tacgaggaga tcagtatgcc attgcgcttg cattgataga tgaaggaaaa    660
gtagttctcg gagttctttc atgtccgaat cttcctctta ccccaattgg tagttctaat    720
acaaatccta ctgaaaacca agttggctgt cttttctctg ctaaaattgg ttgtggaaca    780
gagaatgcaa tcactagaat ggttcggtgt cgtcaaaggt acatgttagc aatatcgaaa    840
atccagccga cgcatcattc tttgaatcat atgaagctgc tcattctcta catgacttat    900
ctagctccat agctaagaag cttggcgtgc aagcaccgcc tgtaagaatt gatagccagg    960
caaaatatgg tgctctttca cgaggagatg gtgctatata tttacggttt ccacataaag   1020
ggtaccgtga gaaaatttgg gatcatgcag ctggctgcat tgtcgtcaca gaagctggag   1080
gggtagcaac cgatgctgct gggaatgcct tagattctcg aaaggaagta tctttgatta   1140
atacaggcat attgtcacca acagagctga tgccaaaact tttggagccg tacaat       1196
```

```

<210> SEQ ID NO 59
<211> LENGTH: 2000
<212> TYPE: DNA
<213> ORGANISM: Triticum sp.
<220> FEATURE:
<221> NAME/KEY: modified_base
<222> LOCATION: (1723)..(1723)
<223> OTHER INFORMATION: a, c, g or t
<220> FEATURE:
<221> NAME/KEY: modified_base
<222> LOCATION: (1793)..(1793)
<223> OTHER INFORMATION: a, c, g or t
<220> FEATURE:
<221> NAME/KEY: modified_base
<222> LOCATION: (1798)..(1798)
<223> OTHER INFORMATION: a, c, g or t
<220> FEATURE:
<221> NAME/KEY: modified_base
<222> LOCATION: (1812)..(1812)
<223> OTHER INFORMATION: a, c, g or t
<220> FEATURE:
<221> NAME/KEY: modified_base
<222> LOCATION: (1825)..(1825)
<223> OTHER INFORMATION: a, c, g or t
<220> FEATURE:
<221> NAME/KEY: modified_base
<222> LOCATION: (1864)..(1864)
<223> OTHER INFORMATION: a, c, g or t
<220> FEATURE:
<221> NAME/KEY: modified_base
<222> LOCATION: (1885)..(1885)
<223> OTHER INFORMATION: a, c, g or t
<220> FEATURE:
<221> NAME/KEY: modified_base
<222> LOCATION: (1891)..(1891)
<223> OTHER INFORMATION: a, c, g or t
<220> FEATURE:
<221> NAME/KEY: modified_base
<222> LOCATION: (1893)..(1893)
<223> OTHER INFORMATION: a, c, g or t
<220> FEATURE:
<221> NAME/KEY: modified_base
<222> LOCATION: (1946)..(1946)
<223> OTHER INFORMATION: a, c, g or t
<220> FEATURE:
<221> NAME/KEY: modified_base
<222> LOCATION: (1973)..(1973)
<223> OTHER INFORMATION: a, c, g or t
<220> FEATURE:
<221> NAME/KEY: modified_base
<222> LOCATION: (1975)..(1975)
<223> OTHER INFORMATION: a, c, g or t
<220> FEATURE:
<221> NAME/KEY: modified_base
<222> LOCATION: (1982)..(1982)
<223> OTHER INFORMATION: a, c, g or t
```

<220> FEATURE:
<221> NAME/KEY: modified_base
<222> LOCATION: (1985)..(1985)
<223> OTHER INFORMATION: a, c, g or t

<400> SEQUENCE: 59

```
ctcgtgccga attcggcacg aggcgcgtgg gcctcctcct cgctccctcc tccctcgccc      60
gaaacccacc tcgtgctcgc ctcccttatc ccctgccttc ccaccacctt ggccgcccca     120
cctaccgccg attcgcctcc tccgcgccgc tgcgctcccc cctctggtgg ccccgccaag     180
cgccacccct cttttccgcc cgcgccatgt cagggtccgc cggtagcccc cgtacgccg      240
ccgagcttgc agccgccaag aaggccgtcg cccttgccgc ccgcctatgc cagactgtac     300
aacaggaaat tctgcaatca gatattcagt ccaaggcaga taaaagtcct gtgacagtag     360
ctgactatgg atctcaagta ttggtaagcc ttgcgttaaa tatggaagta acttctggtt     420
cattttctat ggtggccgaa gaggactcag aagacttgag aaaggatagc gctgaagaaa     480
ttctggaaca tattactgat cttgtaaatg aaactctcgc tgaggatggt tcatacaaca     540
ttactttatc taaggaaggt atcctctctg caattgatac tgggaagtct gaaggaggtc     600
catctggccg acattgggtt ctggatccaa ttgatggac taaaggtttc ttgagaggag     660
gccaatatgc aatcgcactg gcactgcttg atgagggcaa agttgttttg ggcgtgttgg     720
gatgtccaaa tcttcctttg acatcaataa gcaacctcaa tggtagctca tcaggagatc     780
aaacgggggc cctcttttca gctacaattg gttgtggtgc tgaagtagag tcattagagg     840
gctctccacc acaaaagatt agtgtttgta ccatcgacaa tccagtgaat gcctcgttct     900
ttgaatccta tgaaggagca cacacaatgc atgatttaac tggctctata gcggagaaac     960
ttggtgtcca agtcctcca gtcagaatag atagccaagc aaaatatggt gctctggccc    1020
gtggcgatgg tgccatttac ttgcgttttc cacacaaggg ttataaggaa aagatatggg    1080
atcatgcagc tggcgcaatt gtcgtcacag aagctggagg tgtagtaaca gatgcctcag    1140
gaaacgatct cgatttctcg aaagggagat tcttgatgt tgacacaggc atcattgcca    1200
caaataagca gttgatgcca tcactgctga agtctgtcca ggaggccatc aaggagaaaa    1260
gccaggcccc ttccccattg tagaagcttt tttggtttga accttccctg ttgtagttgg    1320
attgatccaa acaatgatc gcaatgccac accttattca cactgttcta tgtgtaaatg    1380
accttttgt tgggacaaag gcaatccttg ttgtatcaca tttgtacatc taaggagtgg    1440
tgacagccat gtcttaaata aaagaggcat ctgcctgcag ttataaatat cttagcatag    1500
ctttgttcaa cataaatgtc agcaacaact attctttgtg tgagcaacag ccaatctctt    1560
gtattatttc tttcagagat ttttgatgtg cagtttatcc ccccttgtta aattacatac    1620
aattcaagct ataatcaata ttaactctta tggtaccaac taaatcatca ttcatgggta    1680
cttgcagact caacattgca gagctaaggc taataggact aancaggcac atcagctgga    1740
tactctgcag aatgcttttt gatggtatcc agcagctacc gctcttgctc acnaaggntg    1800
ggaagcattt gntcatacac atcantgaag agctccgcaa ggccgtgttt tggaacctcc    1860
ggcnactgaa tggcttgcag gaacnttgcc nanatgtcct gagtaaaccc tgagtgcgca    1920
cacatcatcc ctgaacaatt cgtccngaga cggatcccgt gtccaagcca acnanaacgg    1980
cngantggtt aactcgagcc                                                2000
```

<210> SEQ ID NO 60
<211> LENGTH: 1339
<212> TYPE: DNA
<213> ORGANISM: Hordeum vulgare

```
<220> FEATURE:
<221> NAME/KEY: modified_base
<222> LOCATION: (5)..(5)
<223> OTHER INFORMATION: a, c, g or t
<220> FEATURE:
<221> NAME/KEY: modified_base
<222> LOCATION: (1143)..(1143)
<223> OTHER INFORMATION: a, c, g or t
<220> FEATURE:
<221> NAME/KEY: modified_base
<222> LOCATION: (1152)..(1152)
<223> OTHER INFORMATION: a, c, g or t
<220> FEATURE:
<221> NAME/KEY: modified_base
<222> LOCATION: (1220)..(1220)
<223> OTHER INFORMATION: a, c, g or t
<220> FEATURE:
<221> NAME/KEY: modified_base
<222> LOCATION: (1270)..(1270)
<223> OTHER INFORMATION: a, c, g or t

<400> SEQUENCE: 60
caaanaatcc tcactagaag ggaaagacaa agttgcagcg tcagcgcgac ctgcccgtgc        60
ccgccccacc taccgccgcc ggccgcccaa tcgattggca atgtcgcggc ccgccggcaa       120
tcccccgtac gccgtcgagc tcggcgccgc gaagaaggcc gtctccctcg ccgcccgcct       180
atgccagacg gtgcagcagg aaatcgtgca gtcagacatt caatctaagg cggataagac       240
tcctgtcacc gtagctgatt atggatctca ggtattggtg agtcttgtgt aaatatgga        300 agtaacctct ggttcctttt ctatggtggc cgaggaggat tcagaagact gagaaagga        360 tggcgctgac gaaattctgg agcgcattac tgatctcgta aacaaaactc tcgctgagga       420
tggttcatac aacatttat tatctaagga agctatcctc tctgcacttg ataccgggaa        480
gtccgagggt ggtccatctg gccgacattg ggttctagat ccaattgatg ggactaaagg       540
attcgtgaga ggaggccaat atgccattgc actggcactg cttgatgagg caaagttgt        600 cttaggtgtg ttgggatgtc caaatcttcc tttgacatca ataagtaacc tcagtgatag       660
ctcatcaaga gatcaaaccg gggccctctt ttcagctgca atcggttgtg gtgctgaaga       720
gcagtctttg gatggctctc caccacaaaa gattagtgtt tgtaccatca ttgctacaaa       780
taaacagtca atgccatcag tccttgaagc ctatcaagga gcacacacca agcgagaaaa       840
aacaggcccc gtagccaatg aaaaagggtg tccaacctcc tccagtcact gaagttagat       900
agccaaccaa aataatgatc gctatgctac tccgtggaca tggatgcaca ctgttaatgg       960
cgtaacccac acgagggtta cagggaaaca atatgggatc atgcagctgg ctcaattgtc      1020
gtcacggaag ctggaggtgt agttaaagat gcctcaggaa acgatctcga tttctcgaaa      1080
ggaagatttc ttgatcgtga cacaggcatc attgctacaa ataaacagtt gatgccatca      1140
gtncctgaag tnctgtccag gaggcaatca aggagaaaaa acaggcctct tctccattgt      1200
aaaaggtttt tttaaccttn ccctgttact gaagttggat tggtccaaaa taatgatcgc      1260
tatgctactn ccttgttcat ttattcacac tgtttatgtg taagtgacct tttgttggaa      1320
aaaatacaac ccttgttat                                                   1339

<210> SEQ ID NO 61
<211> LENGTH: 1498
<212> TYPE: DNA
<213> ORGANISM: Oryza sp.

<400> SEQUENCE: 61
gtggaattcc ggtcgcgccg tgcatctcgt acgtgacggg gaggggcggc ctcacccagg        60
gatgctgcaa cggcgtcaag gggctgaaca acgccgcccg caccaccgcc gaccgccagg       120
```

-continued

| | |
|---|---|
| ccgcctgccg ctgccgcgag actccgcgcc agcgccacca tgtcgcaggc cgccgggaac | 180 |
| ccctacgccg ctgagctcgc cgccgccaag aaggccgtca ccctcgccgc ccgcctctgc | 240 |
| caggcggtgc aaaaggacat tctgcagtct ggtgttcagt ctaaggcgga tcaaagtccg | 300 |
| gtgacagttg ccgattatgg gtctcaaata ttggtaagcc ttgtcttgaa aatggaagca | 360 |
| ccagcttctt cttccttctc tatggtggct gaggaggact cggaagaatt gaggaaagaa | 420 |
| ggcgcagaag aaattttaga aaatatcacc gagctcgtaa acgaaactat cgtagatgat | 480 |
| ggtacataca gcatttactt ctctaaggaa ggtatcctct ctgcaattga cgacggcaag | 540 |
| tctgagggag gtccatctgg gcaacactgg gtgctagatc caattgatgg gactaaaggt | 600 |
| ttcttaaggg gagaccaata tgctattgcc ctggctctgc ttgatgaggg taaagttgtt | 660 |
| ttgggtgtat tggcttgtcc caacctttct ttgggatcaa taggcaacct taatggtggc | 720 |
| tcctcgggag atcaagttgg tgctctcttt tctgctacta ttggttgtgg agctgaagta | 780 |
| gagtctttac agggctctcc agcacaaaag attagtgtct gttccatcga caatccagtc | 840 |
| gaagcttcat tctttgagtc ctacgaaggg gcacactcct tgcgtgattt aacaggctcc | 900 |
| attgcggaga aacttggtgt ccaagctcct ccagttagaa ttgatagcca agcaaaatac | 960 |
| ggtgccctag cccgaggtga cggtgccatt tacttgcgtt ttccacacaa aggttacaga | 1020 |
| gagaagatct gggatcatgc agctgggtca atcgtcgtga cagaagctgg aggtctggtg | 1080 |
| acagatgcat caggaaacga tttggatttc tccaaaggga gatttcttga tctcgacaca | 1140 |
| gggatcatcg cgacgaacaa gcagctgatg ccttcactcc tgaaggctgt gcaagatgcc | 1200 |
| atcaaggagc aaaaccaggc tgcttccccg ttgtagtagc tgtctcaatc cacaatccac | 1260 |
| aaatatcata atgtttccat ataataataa ttgcagtgct gcttccccat caacattact | 1320 |
| ttaaatgtgt gtacagcacc actttgttgt tgttgctgct gcaaattcag tatcttattg | 1380 |
| ttgcacattt ctgcatctaa ttggtgggtg agctggcacc acatgaatgt tctttcatct | 1440 |
| ggattcagaa gaaataatta aattggcctg attctcccta actcggggca atattgct | 1498 |

<210> SEQ ID NO 62
<211> LENGTH: 1544
<212> TYPE: DNA
<213> ORGANISM: Zea mays

<400> SEQUENCE: 62

| | |
|---|---|
| cgcacatggc tgcgcgcgtg ggcctgctcc cgcacgcgat cctcgtctcc tcccgagctc | 60 |
| tacccacgcc ccgagctcgc gtcccttatc ctcttccacc cgtcccttcc tacctccgcc | 120 |
| acgcctcctc ctccgcctcc cgctcctgcc gcgcgtcgcc gcgttttgtc gcagtccgcg | 180 |
| ccatggcttc ggggaacccc tacgccgccg agctcgccgc cgccaagaag gccgtcaccc | 240 |
| tcgccgccaa actctgccag acagttcaac aggatattat gcattctggc gttcaggcta | 300 |
| aggcagacaa aagtcctgtc acagtggctg attatggatc tcaaatattg gtcggttttt | 360 |
| ccttaaagat ggatgtatca tctgaccat tttcattggt ggctgaagag gactcagatg | 420 |
| aattgagaaa agatggcgct gaagaaattt tggaagatat tactgacctt gtcaatgaaa | 480 |
| ccatctttga tgatggttca tataacattt cgtttacaaa ggaaggtata ctctctgcaa | 540 |
| ttgatgatgg gaagtctgag ggaggtccat ctggacgaca ttgggtgctt gatccgattg | 600 |
| acggtactaa aggtttcttg agggcgacc aatatgccat tgcattggct ctgcttgatg | 660 |
| aaggtaaagt tgtttgggt gtattggctt gtccaaatct tccattgtca tcaataaaca | 720 |
| acatcaatgg taactcttcg ggagataaag ttggtgccct gttttctgct acaattggtt | 780 |

```
gtggggctca agtagagtcc ttagatggct ctccaccaca aaagattagt gtttgctcca         840
tcgacaatcc tgtcaatgca tcattttttg aatcctatga aagtgcacac tccatgcatg         900
atttgactgg ctctattgca gagaaacttg gtgtccaagc tcctccagtt agaatcgaca         960
gccaagcaaa atatggtgct ctggcccgag gtgatggcgc catttacttg cgctttccac        1020
acaaaggtta tagagagaaa atatgggacc atgcagcagg atcaattgtc gtgacagaag        1080
ctggaggcat agtaacagat gctgcgggaa acgacttgga tttctccaaa gggagatttc        1140
tggatctcga cacaggcatc atcgcaacca acaaggagtt gatgccgtcg ctcctgaaag        1200
ctgtccaaga ggctattaaa gagacgaacc aggctgcctc cctcttatag ctgttgtagt        1260
ggtcgacaaa aaagtagttg caaaattttc gtactggcaa acaggtgtgc atcatttctc        1320
cgtggtatta cagagtctag caaatttata gcatcaacct gattggtgat cagacgtcca        1380
ttcgttttac tgaatcacct tcttggtgca gcattgctag aagtggacaa catgaataat        1440
ttgagtgagt ccatagttgc ctgaactcag ctttggcatt tgaactggtt atagaaattg        1500
tgaaataatt aatggatatt tggaagacaa acttgaactt caag                         1544

<210> SEQ ID NO 63
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, g or t
<220> FEATURE:
<221> NAME/KEY: modified_base
<222> LOCATION: (11)..(11)
<223> OTHER INFORMATION: a, c, g or t

<400> SEQUENCE: 63
ngtcgaswga nawgaa                                                          16
```

METHOD FOR IMPROVING STRESS RESISTANCE IN PLANTS AND MATERIALS THEREFOR

RELATED APPLICATIONS

This application is the U.S. national phase, pursuant to 35 U.S.C. §371, of PCT international application Ser. No. PCT/AU2008/000895, filed Jun. 19, 2008, designating the United States and published in English on Dec. 24, 2008 as publication WO 2008/154695 A1, which claims priority to Australian provisional patent application No. 2007903309, filed Jun. 20, 2007, and Australian provisional patent application No. 2008901466, filed Mar. 26, 2008. The entire contents of the aforementioned patent applications are incorporated herein by this reference.

SEQUENCE LISTING

The instant application contains a Sequence Listing which has been submitted in ASCII format via EFS-Web and is hereby incorporated by reference in its entirety. Said ASCII copy, created on Aug. 16, 2013, is named 85355-54316_SL.txt and is 63,304 bytes in size.

FIELD OF THE INVENTION

The present invention relates to stress resistance in plants, such as drought resistance, salt resistance, heat or cold resistance, light resistance and pH resistance, and methods and materials for increasing stress resistance in plants, and for screening plants for mutations which are associated with increased stress resistance. The invention also relates to methods and materials for delaying the onset of flowering in plants and for altering the leaf shape of plants.

BACKGROUND TO THE INVENTION

The biggest limiting factor in crop yields across the world is abiotic stress, causing an average loss of more than 50% of potential yield (Boyer, J. S. (1982), "Plant Productivity and Environment" *Science* 218(4571): 443-448). Abiotic stresses include temperature extremes, salinity, acidic soils, high light intensities, drought and combinations thereof.

As plants are sessile and cannot escape these stress conditions, they respond by changing their protein and metabolite composure, morphology and physiology. These changes allow the plant to limit damage by adapting to the stress conditions and also to repair damage caused by the stress.

These changes are mediated by processes that sense the stress and/or its effects on the plant and activate multiple, complex signalling pathways. Different pathways are activated depending on the type of stress conditions experienced by the plant but often there is overlap and interaction between pathways. This overlap can lead to cross-tolerance, that is tolerance to multiple types of stress despite exposure to only one stress. This is important as stresses rarely occur in isolation. For example cold stress will also cause high light stress as the cold causes the metabolism of the plant to slow yet it is still able to harvest as much light energy as before. Likewise drought can cause heat stress as the stomata close to conserve water but as a result lose the cooling effect of transpiration, resulting in heat stress. Furthermore in nature the stress conditions rarely exist in isolation. In Australia it would be conceivable that a crop would experience drought and high light stress at the same time.

Although some components of stress signalling pathways have been studied, due to the complexity of stress response pathways the position of these components in the pathways and their interactions with other components is poorly understood and existing methods for improving the stress resistance of plants are accordingly limited.

Thus, there is a need for new methods for producing plants with increased stress tolerance.

SUMMARY OF THE INVENTION

The present investigations have surprisingly shown that mutations in the SAL1 gene which result in reduced or no activity associated with the SAL1 protein, result in increased stress resistance of the mutant plants.

Thus, according to an aspect of the invention, there is provided a method for obtaining a plant with increased stress resistance relative to a wild-type plant, comprising:
  (a) introducing at least one mutation or exogenous nucleic acid into the genome of one or more plant cells which results in reduced activity associated with SAL1 or a homologue thereof in said one or more plant cells;
  (b) regenerating one or more plants from said one or more plant cells; and
  (c) selecting one or more plants that have increased stress resistance relative to a wild-type plant.

At least one mutation or exogenous nucleic acid may be introduced by any appropriate means known in the art. For example, mutations may be introduced by chemical or physical mutagenic techniques, or using insertional mutation means such as transposons or T-DNA, and exogenous nucleic acid may be introduced by recombinant means employing, for example, chemical assisted cell permeation (using, for example, calcium, lithium, PEG), electroporation, microinjection, liposome-mediated transfection, microparticle bombardment (biolistics), *Agrobacterium*-mediated transformation, virus infection, protoplast fusion or any other appropriate means as are known in the art.

According to an embodiment of the invention, the method comprises introducing at least one mutation into the SAL1 gene or a homologue thereof, or inhibiting or suppressing the expression of the SAL1 gene or a homologue thereof.

At least one mutation may be introduced into a nucleotide sequence encoding SAL1 or a homologue thereof in said one or more plant cells, and may comprise an insertion, deletion or substitution of one or more nucleotides.

According to another embodiment, the mutation may comprise an insertion, deletion or substitution of one or more nucleotides in the region of nucleotides 731 to 745, 1226, 1518, 1519, and 1690 of SEQ ID NO:1, or an equivalent position in a homologue of at least nucleotides 191-1991 of SEQ ID NO:1.

According to another embodiment, the mutation may comprise a guanine to adenine mutation at position 1226 of SEQ ID NO:1, or an equivalent position in a homologue of at least nucleotides 191-1991 of SEQ ID NO:1. The resulting mutation may result in an amino acid change of glycine to aspartic acid at position 217 of SEQ ID NO:2.

According to another embodiment, the mutation may comprise a cytosine to thymine mutation at position 731 of SEQ ID NO:1, or an equivalent position in a homologue of at least nucleotides 191-1991 of SEQ ID NO: 1. The resulting mutation may result in an amino acid change of alanine to valine at position 124 of SEQ ID NO:2.

According to another embodiment, the mutation may comprise a guanine to adenine mutation at position 736 of SEQ ID NO:1, or an equivalent position in a homologue of at is least nucleotides 191-1991 of SEQ ID NO:1. The resulting mutation may result in an amino acid change of glutamic acid to lysine at position 126 of SEQ ID NO:2.

According to another embodiment, the mutation may comprise a guanine to adenine mutation at position 1690 of SEQ ID NO:1, or an equivalent position in a homologue of at least nucleotides 191-1991 of SEQ ID NO:1.

According to another embodiment, the mutation may comprise insertion of one or more nucleotides between positions 734 and 735 of SEQ ID NO:1, or an equivalent position in a homologue of at least nucleotides 191-1991 of SEQ ID NO:1, or the mutation may comprise substitution of nucleotides 735-745 of SEQ ID NO:1, or equivalent nucleotides in a homologue of at least nucleotides 191-1991 of SEQ ID NO:1 with one or more nucleotides.

According to another embodiment, the mutation may comprise insertion of one or more nucleotides between or including positions 1518 and 1519 of SEQ ID NO:1, or an equivalent position in a homologue of at least nucleotides 191-1991 of SEQ ID NO:1.

According to one embodiment, the mutation may be a SAL1 null mutation.

According to yet another embodiment, a method of the invention may comprise introducing into said one or more plant cells exogenous nucleic acid which inhibits expression of endogenous SAL1 or homologue thereof, or which replaces expression of endogenous SAL1 or homologue thereof with expression of an exogenous protein. The exogenous protein may be an exogenous mutant SAL1 or homologue thereof, or any other suitable protein, such as a protein providing a screenable phenotype.

Plants resulting from methods according to the invention may have increased resistance to a number of abiotic stresses including, but not limited to, drought, salinity, temperature stress, light stress, soil pH and mineral toxicity, relative to a wild-type plant, or any combination thereof. The plants may have increased resistance to biotic stresses, relative to a wild-type plant, induced by, but not limited to, animals (including grazing animals and pest or parasite organisms), bacteria, fungi, and viruses or any combination thereof.

According to an embodiment, the resulting plant has at least increased drought resistance relative to a wild-type plant.

According to another embodiment of a method of the invention, the resulting plant may have a delayed flowering time.

According to another embodiment of a method of the invention, the resulting plant may have an altered leaf phenotype.

According to yet another embodiment of the invention, there is provided a method for obtaining a plant with altered flowering time relative to a wild-type plant, comprising:
(a) introducing at least one mutation or exogenous nucleic acid into the genome of one or more plant cells which results in reduced activity associated with SAL1 or a homologue thereof in said one or more plant cells;
(b) regenerating one or more plants from said one or more plant cells; and
(c) selecting one or more plants that have altered flowering time relative to a wild-type plant.

According to yet another embodiment of the invention, there is provided a method for obtaining a plant with altered leaf phenotype relative to a wild-type plant, comprising:
(a) introducing at least one mutation or exogenous nucleic acid into the genome of one or more plant cells which results in reduced activity associated with SAL1 or a homologue thereof in said one or more plant cells;
(b) regenerating one or more plants from said one or more plant cells; and
(c) selecting one or more plants that have altered leaf phenotype relative to a wild-type plant.

Plants obtained by the methods of the invention, and plant parts (including leaves, stems, roots, tubers, flowers, fruit and parts thereof) and mutant/transgenic seed from the plants are also provided.

According to another embodiment of the invention, there is provided a method for screening a plant for the presence of at least one mutant allele of a nucleotide sequence encoding SAL1 or a homologue thereof, said method comprising analysing DNA of the plant using at least one nucleic acid molecule suitable as a probe or primer which is capable of hybridising to a SAL1 gene or homologue thereof under stringent conditions.

According to a more specific embodiment the screening method ma comprise the use of at least one oligonucleotide primer pair suitable for amplification of a region of the SAL1 gene or homologue thereof, comprising a forward primer and a reverse primer to detect the presence or absence of a mutation in said region. The region may comprise the whole SAL1 gene or homologue thereof, or may comprise only a portion thereof, such as, for example (and referring to FIG. 10), the nucleotide region comprising exon 3, the intron between exons 3 and 4, exon 5, the intron between exons 5 and 6, exon 6, and the intron between exons 6 and 7, or any combination thereof.

The nucleic acid molecule, or member of an oligonucleotide primer pair, may be any size is suitable for specific hybridisation to a target nucleotide sequence under stringent conditions, and may comprise from about 15 nucleotides to about 100 nucleotides, but may more typically be from about 15 to about 30 nucleotides in length.

The SAL1 gene and approximately 1.07 kb of promoter were digested from the T8H11 BAC from The Arabidopsis Information Resource (TAIR) and ligated into the pCAM2300 binary vector (CAMBIA, Canberra, Australia). Both Col-0 wild type and alx8 plants were transformed by *Agrobacterium*-mediated transformation. Two lines of alx8 complemented with the wild type copy of the gene were isolated. Seven lines of Col-0 wild type containing the construct were also isolated and showed no visible phenotype.

FIG. 3—alx8 SAL1 genomic sequence (TAIR Accession Sequence: 4010730406; to Name: AT5G63980.1; Sequence Length (bp): 2122; Date last modified: Apr. 17, 2007). This genomic sequence is an updated version of previous TAIR Accession No. 2160829, and which locates the start codon 162 nucleotides upstream of the presumed start codon in TAIR accession No. 2160829. The point mutation in alx8 (g1226a), the start codon (atg) and the stop codon (tga) are highlighted.

FIG. 4—alx8 Amino Acid Sequence (TAIR Accession: AASequence: 4010745380; Name: AT5G63980.1; Length: 407aa; Date last modified: Aug. 16, 2007). This sequence is identified in the sequence listing as SEQ ID NO:2.

The amino acid change in alx8 (G217D) is highlighted.

FIG. 5—Alignment of Proteins with Homology to SAL1 Proteins with homology to SAL1 were identified using the blastp tool at the National Centre for Biotechnology Information Website. (NCBI). These were then aligned using ClustalW at the European Bioinformatics Institute (EMBL-EBI). Accession numbers are as follows: SAL1, AY034894/Q42546 (SEQ ID NO:46); *Oryza sativa*, NP_001066326/NM_001072858 (SEQ ID NO:44); *Zea mays*, AAK57915/AF288075 (SEQ ID NO:45). "*" means that the residues in that column are identical in all sequences, ":" means that conserved substitutions have been observed, and "." means that semi-conserved substitutions are observed.

FIG. 6—Homology of EST with SAL1 mRNA
A. ESTs found to have homology to the SAL1 mRNA using blastn at The Gene Index Program website (TGI). Percentage identity calculated by the same program.
B. Sequence alignment of ESTs listed in A, Sequences were aligned using ClustalW at the EMBL-EBI website. "*" means that the nucleotides in that column are identical in all sequences in the alignment. The following sequences are identified in the sequence listing: Spruce (SEQ ID NO: 47); Pine (SEQ ID NO: 48); Medicago (SEQ ID NO: 49); Lotus (SEQ ID NO: 50); Soybean (SEQ ID NO: 51); SAL1 (SEQ ID NO: 52); Oilseed (rapeseed) (SEQ ID NO: 53); Poplar (SEQ ID NO: 54); Cotton (SEQ ID NO: 55); Tomato (SEQ ID NO: 56); Potato (SEQ ID NO: 57); Onion (SEQ ID NO: 58); Wheat (SEQ ID NO:59); Barley (SEQ ID NO:60); Rice (SEQ ID NO:61); and Maize (SEQ ID NO:62).
C. Cladogram showing an estimation of common ancestry based on the alignment in B. Calculated by the EMBL-EBI website.

Figure 7:

FIG. 7—Effect of Drought Conditions on Col-0 Wild Type, Fry1-1 and Alx8.

Water was withheld for 13 days at 21° C., 150 μmol photons.m$^{-2}$.s$^{-1}$, 16 hr day/8 hr night. Plants are representative of 5 biological replicates of each ecotype. All plants were of the same approximate developmental age and were not yet flowering at the start of the drought time course: wild-type plants were 4 weeks old while alx8 and fry1-1 plants were 8 weeks old.

FIG. 8—Fry1-1 and Alx8 are Drought Tolerant.
4-Week old plants were exposed to drought conditions for 25 days, at 21° C. and 150 μmol photons.m$^{-2}$.s$^{-1}$, 12 hr day/12 hr night.

A) Photographs of fry1-1, C24 wild-type, alx8 and Col-0 wild-type plants after 0, 10, 17, 21 and 25 days exposure to drought conditions. The plants are representative of five plants from each genotype in two separate experiments.
B) Water loss from the soil was approximated by pot weight over the time course. Both the pot weight for the plants in A) and the average pot weights are given. Error bars are standard deviations between the five biological replicates.

FIG. 9—SAL1 genomic sequence from the drought tolerant *A. thaliana* mutant SALK_020882 (the start codon (atg) and the stop codon (tga) are highlighted). A T-DNA insertion line in the Col-0 ecotype obtained from the *Arabidopsis* Biological Resource Centre (ABRC). The mutation is allelic to alx8.

A) The insertion site given by TAIR. This was established by single pass sequencing from the LB of the T-DNA insert. This gave complementary sequence, ie. towards the 5' end of the gene.
B) To confirm the location of the insertion Tail PCR from the left border of the insert on DNA from one plant was performed. Sequence was obtained from both sides indicating the possibility of a double insert. The sequence obtained also indicated the deletion of 11 bp around the insertion site.

Figure 10:
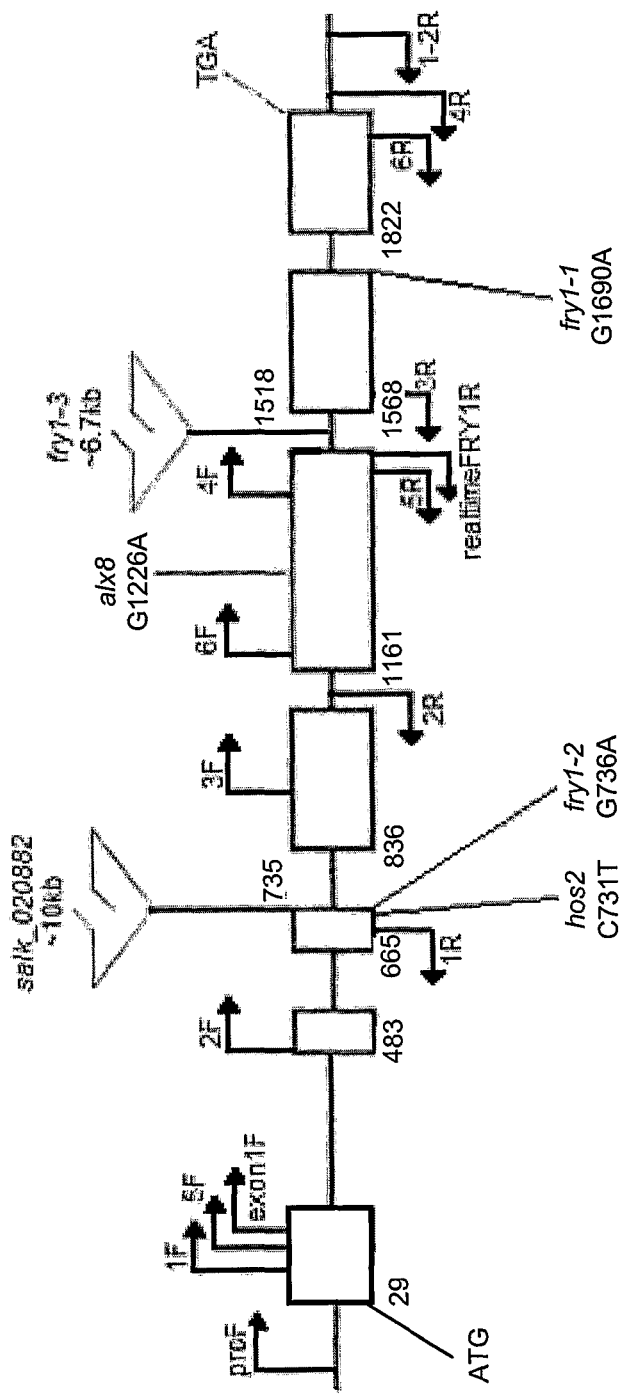

FIG. 10—Scale depiction of the SAL1 gene. Exons are represented by boxes, introns by lines, arrows represent primers designed for amplification (see Table 1), the location of the salk and fry1-3 insertions, and of the fry1-1, fry1-2, host and the identified alx8 point mutations are also shown.

Figure 11:
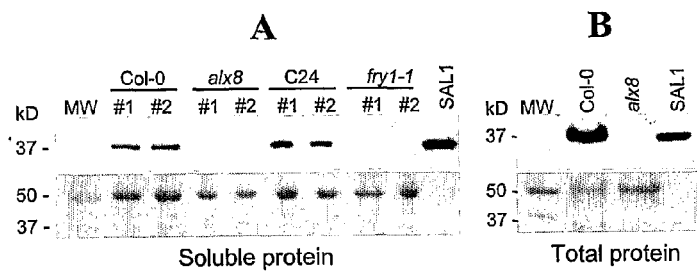

FIG. 11—Western blot of SAL1. The abundance of SAL1 protein in in vivo total soluble leaf protein extracts from Col-0, C24, alx8 and fry1-1 was compared with 5 ng of recombinant SAL1 protein using anti-SAL1 antibodies (FIG. 11A) and total leaf protein from Col-0 and alx8 (FIG. 11B). The large subunit of rubisco detected by Ponceau staining was used as a loading control. Two plants for each genotype were analyzed and molecular masses of the protein markers are indicated.

Figure 12:
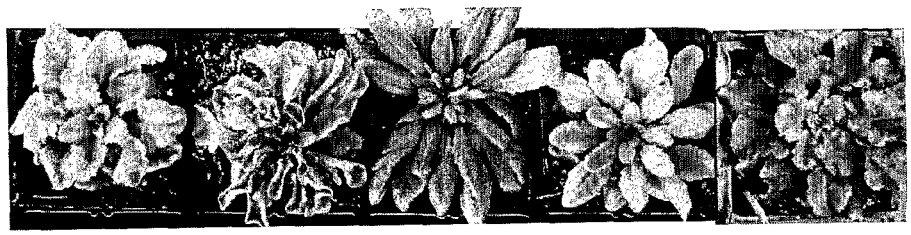

FIG. 12—Photographs of, from left to right: alx8 mutant, fry1-1 mutant, Col-0 wild-type, C24 wild-type and salk_020882 mutant *Arabidopsis thaliana* plants, showing the similar altered leaf morphology of the salk_020882 mutant and alx8 mutants and the altered leaf morphology of the fry1-1 mutant compared to the corresponding C24 wild-type.

Figure 13:
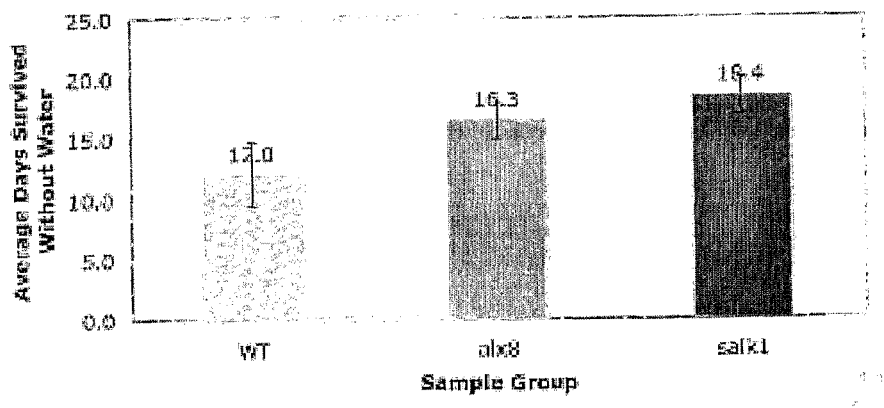

FIG. 13—Bar chart showing the average number of days survived by plants without water. The mutant salk_020882 shows the greatest drought tolerance, surviving for 18.4 days on average, compared to 16.3 days for the alx8 mutant and 12.0 days for the wild-type (sample size: three WT and alx8 plants and six salk_020882 plants)

Figure 14:

FIG. 14—Photographs showing: bottom row—drought test; top row—controls; from left to right: WT plants (11 days, shortly before plant death for the drought stressed plant), salk_020882 mutants and alx8 mutants (both mutants still looking viable after 14 days drought treatment).

Figure 15A:
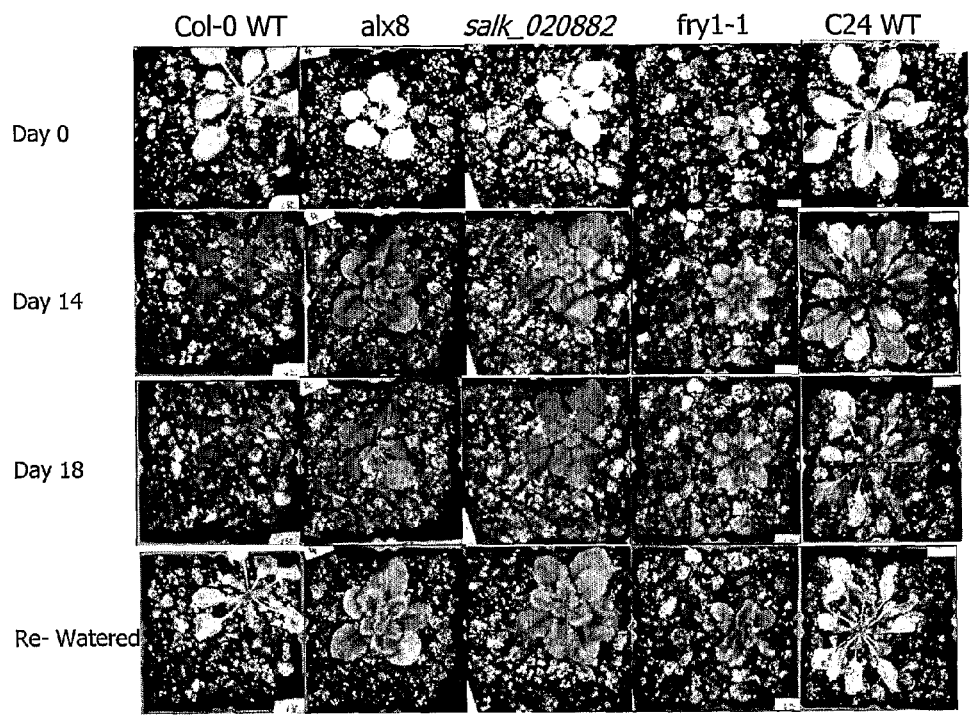
Figure 15B:
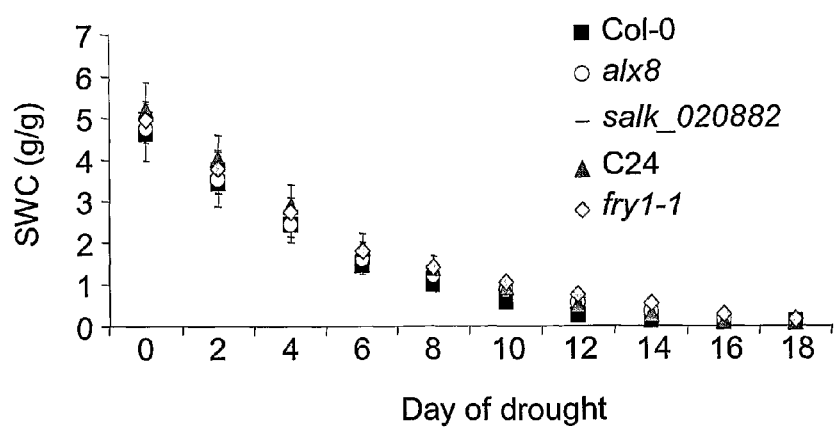

FIGS. 15A and 15B—FIG. 15A shows photographs of, from left to right, Col-0 wild-type, alx8, salk_020882, fry1-1 and C24 wild-type plants after, from top to bottom, 0, 14, 16, and 18 days exposure to drought conditions, and then three days after re-watering. Three days after re-watering, the alx8 and fry1-1 mutant plants show strong recovery, including green, turgid leaves, whereas the wild-type plants show little, if any sign of recovery, most of the leaves being chlorotic and withered. The plants shown are representative of triplicate experiments involving five plants of each genotype. FIG. 15B shows soil water content (SWC) during the drought treatments.

Figure 16A:
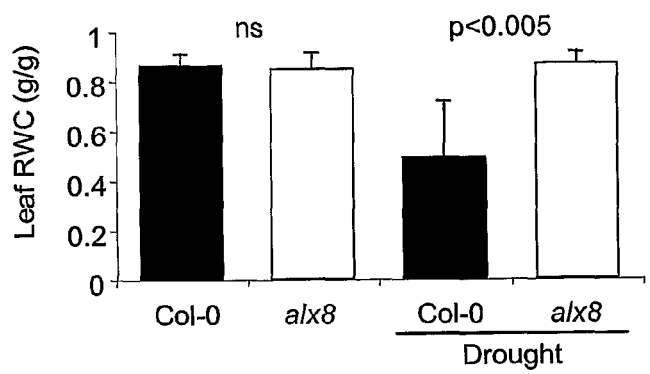
Figure 16B:
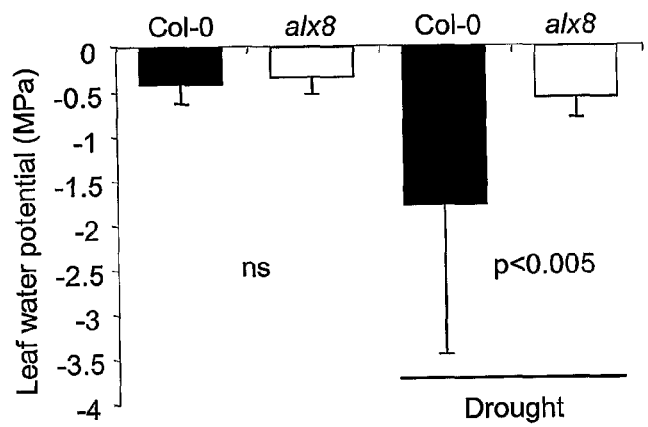

FIGS. 16A and 16B—FIG. 16A shows leaf relative water content (RWC) and FIG. 16B leaf water potential of leaves of Col-0 and alx8 in non-stressed conditions and after 12 days of drought. Columns are mean±stand deviation (SD) of at least four plants.

Figure 17:
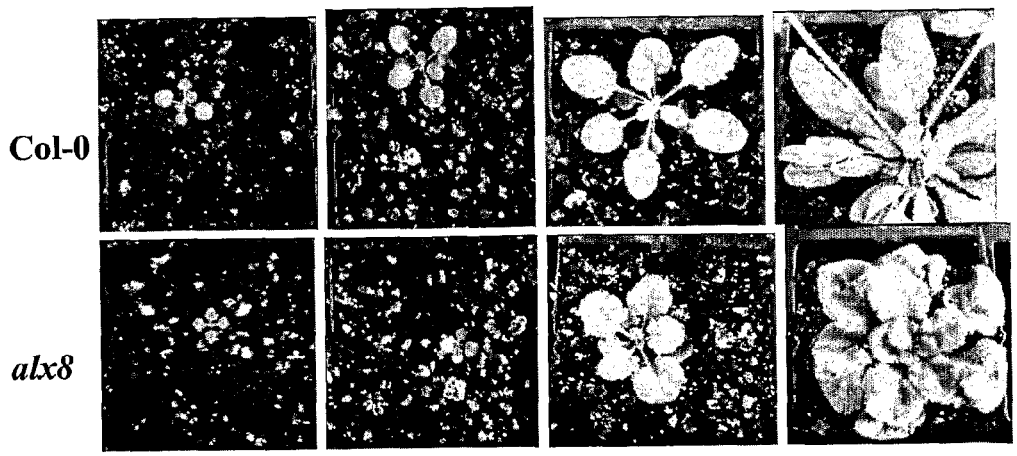

FIG. 17—shows photographs for, top, Col-0 wild-type plants and, bottom, alx8 plants at 2, 3, 5 and 8 weeks of age, showing developmental delay in alx8 plants. Also evident is that the 8-week old Col-0 wild-type plant is flowering (the bolts being evident), whereas the alx8 plant has not.

Figure 18:
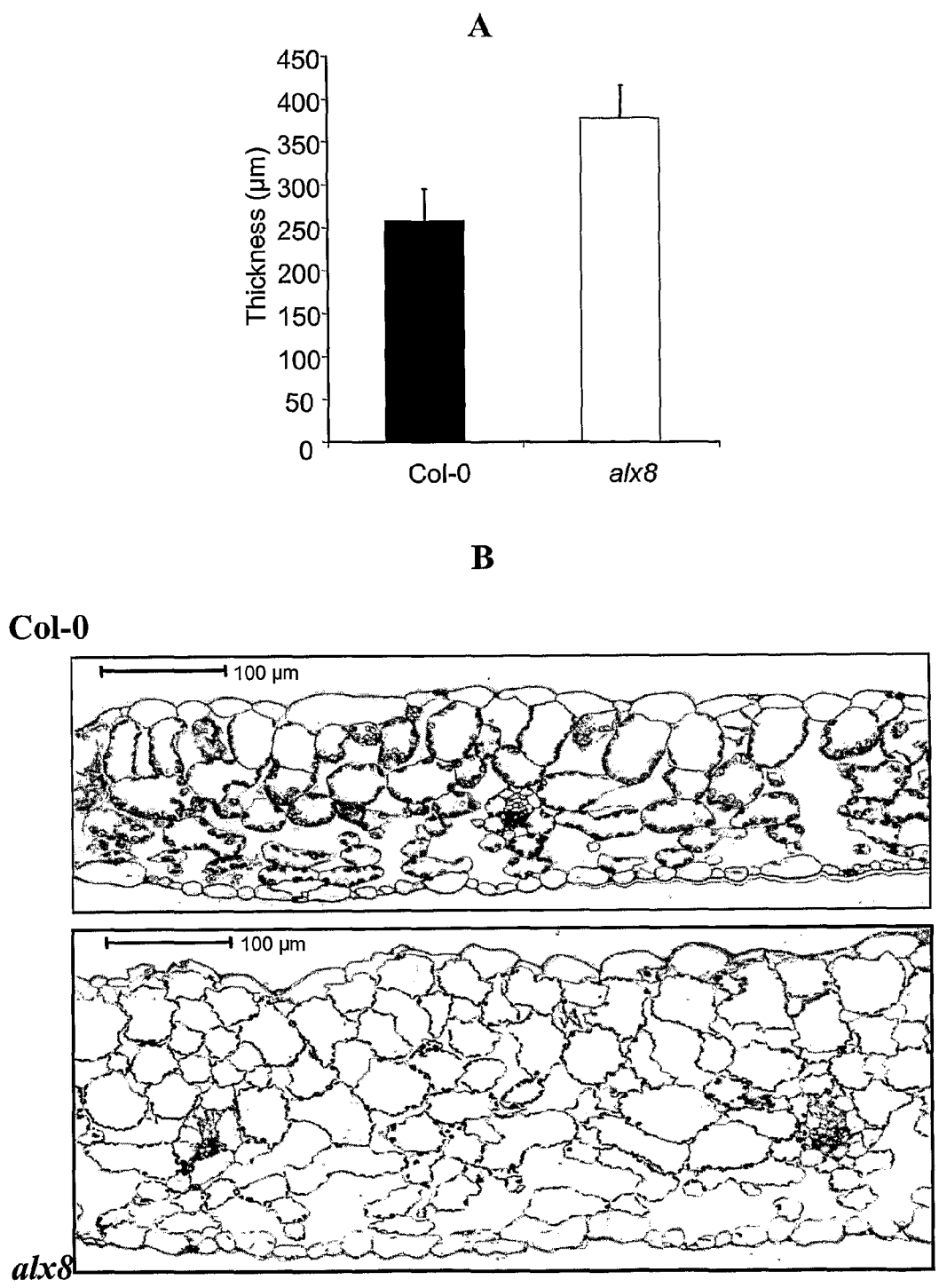

FIG. 18—A shows a bar chart of leaf thickness of Col-0 wild-type leaves and alx8 leaves;
B shows transverse sections of typical Col-0 wild-type leaves and alx8 leaves.

Figure 19:
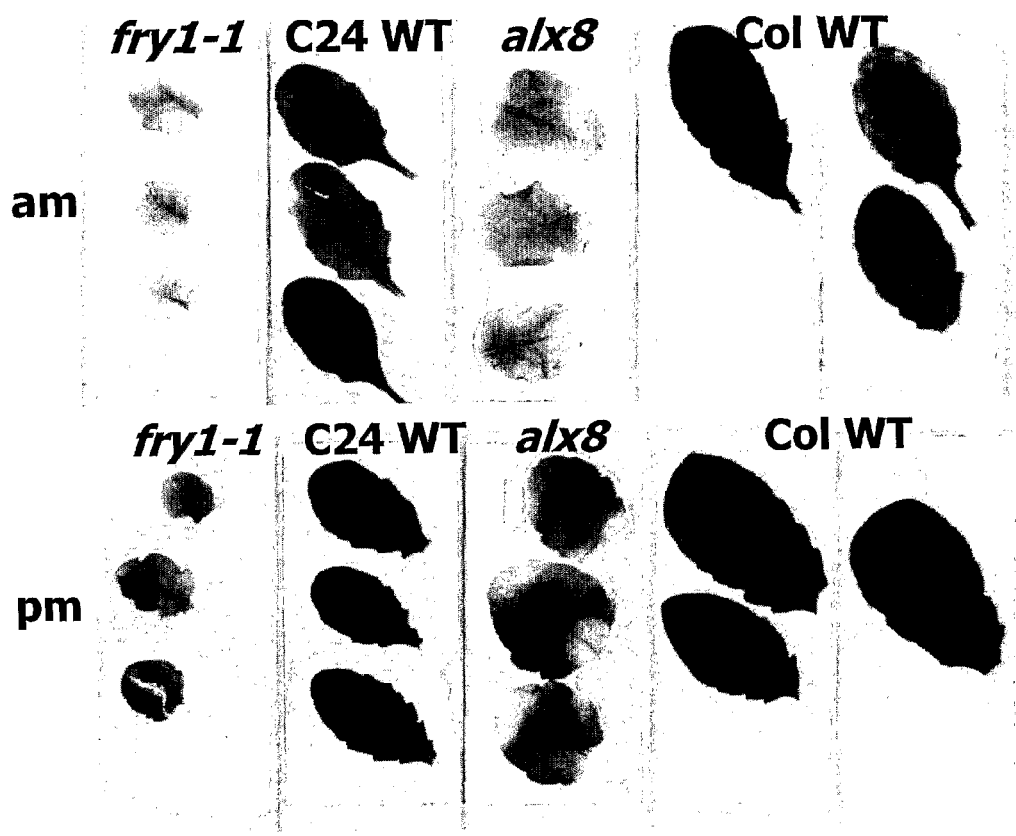

FIG. 19—photographs showing the results of iodine staining of leaves of fry1-1, C24 wild-type, alx8 and Col-0 wild-type plants in the morning (top) and at night (bottom), showing that these SAL1 mutants have significantly reduced starch levels in their chloroplast.

Figure 20:
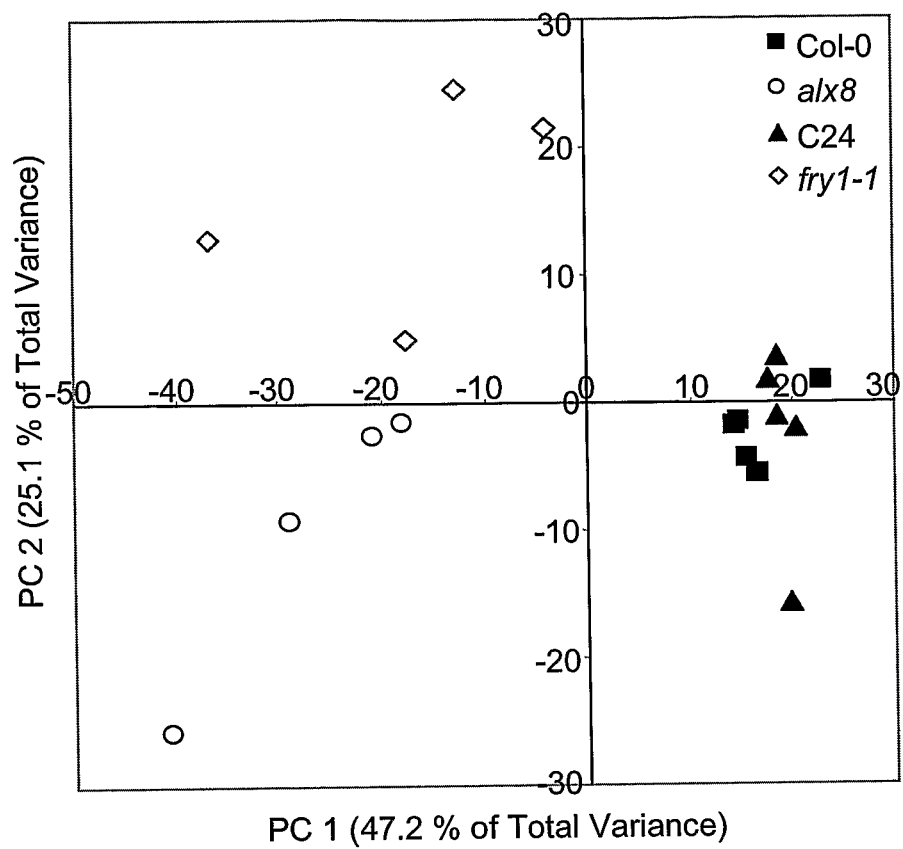

FIG. 20—Principal components analysis (PCA) of metabolite profiles of SAL1 mutants and their respective wild-types. The abundance of over 150 metabolites in at least four biological replicates of each ecotype was used to calculate the PCA. The percentage of total variance accounted for by principal components 1 and 2 (PC1 and PC2) is plotted.

Figure 21:
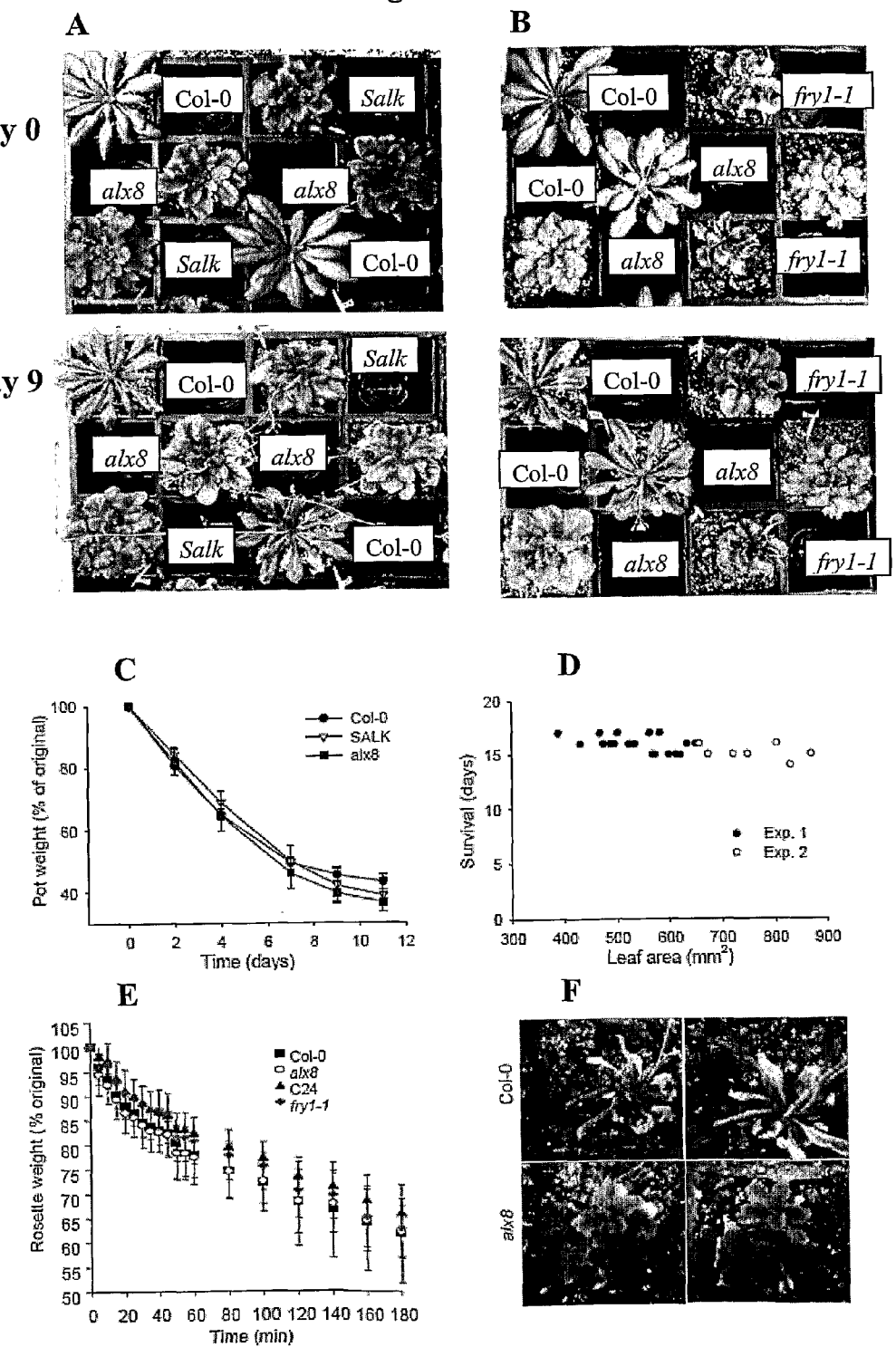

FIG. 21—Shows the impact of size, development and morphology on drought tolerance. (A) Drought tolerance of Col-0, alx8 and salk_020882 at the same developmental stage (commencement of flowering); representative images of 27 alx8 and 5 fry1-1 plants at Day 0 and Day 9 of drought are shown. Plants were grown under 12 hour days. (B) Drought tolerance of plants at the same vegetative stage of development (mature green), alx8 and fry1-1 were four weeks old, Col-0 was eight weeks old. Plants are representative of five biological replicates of each ecotype, growth conditions were 16 hour days. (C) Pot weights for (A) were measured and plotted as a percentage of the original weight; average+S.D. of five of each line is plotted. (D) Rosette area of a range of 30 day old Col-0 plants grown in two separate experiments were plotted against drought viability. Growth conditions were 8 h days. (E) Dehydration of detached rosettes. Data are the mean+SD for four biological replicates. The experiment was repeated three times. (F) Col-0 (one plant per pot) and alx8 (two plants per pot) at the same age were subjected to 9 days withholding of water. Growth conditions were 16 h days.

Abbreviations

ABA—abscisic acid
$IP_3$— inositol 1,4,5 triphosphate
$I(1,4)P_2$— inositol 1,4 bisphosphate
$I(4,5)P_2$— inositol 4,5 bisphosphate
PAP—3' polyadenosine 5' phosphate
ROS—reactive oxygen species
WT—wild-type Definitions As used herein, the term "comprising" means "including principally, but not necessarily solely". Variations of the word "comprising", such as "comprise" and "comprises", have correspondingly similar meanings.

As used herein the term "gene", refers to a defined region that is located within a genome and that may comprise regulatory, nucleic acid sequences responsible for the control of expression, i.e., transcription and translation of the coding portion. A gene may also comprise other 5' and 3' untranslated sequences and termination sequences. Further elements that may be present are, for example, introns.

As used herein, the term "homologue" in the context of proteins means proteins having substantially the same functions and similar properties in different species, and which, within at least regions, share at least 50% amino acid identity. Such homologous proteins may share, over their entire amino acid sequences, at least about 30% amino acid identity, at least about 40% amino acid identity, at least about 50% amino acid identity, at least about 60% amino acid identity, at least about 70% amino acid identity, at least about 80% amino acid identity, at least about 90% amino acid identity or at least about 95% identity. Similarly, homologues of nucleic acid molecules are nucleic acid molecules that encode proteins having substantially the same functions and similar properties in different species, wherein the encoded proteins share, within at least regions, at least 50% amino acid identity (such nucleic acid homologues may share significantly less than 50% identity due to degeneracy in the genetic code, and differences in preferred codon usage amongst different plant genuses and species), and may share at least about 30% amino acid identity, at least about 40% amino acid identity, at least about 50% amino acid identity, at least about 60% amino acid identity, at least about 70% amino acid identity, at least about 80% amino acid identity, at least about 90% amino acid identity or at least about 95% identity over the whole encoded amino acid sequences.

As used herein, the term "mutation" means any change in a polypeptide or nucleic acid molecule relative to a wild-type polypeptide or nucleic acid molecule from which the 'mutant' is derived and may, for example, comprise single or multiple amino acid or nucleotide changes, or both nucleotide and amino acid changes, including point mutations, null mutations, frame-shift mutations, and may comprise deletions, or insertions, or substitutions of one or more nucleic acids or amino acids, which may comprise naturally or non-naturally occurring nucleotides or amino acids or analogues thereof.

A "nucleic acid", as referred to herein, refers to deoxyribonucleotides or ribonucleotides and polymers thereof in either single-, double-stranded or triplexed form. The term may encompass nucleic acids containing known analogues of natural nucleotides having similar binding properties as the reference nucleic acid. A particular nucleic acid sequence may also implicitly encompass conservatively modified variants thereof (e.g. degenerate codon substitutions) and complementary sequences. The terms "nucleic acid", "nucleic acid sequence" or "polynucleotide" may also be used interchangeably with gene, cDNA, and mRNA encoded by a gene.

The terms "polypeptide", "peptide" and "protein" may be used interchangeably herein to refer to a polymer of amino acid residues. Included within the scope of these terms are polymers in which one or more amino acid residues may comprise artificial chemical analogue(s) of corresponding naturally occurring amino acid(s), as well as, or instead of naturally occurring amino acid polymers. The terms "polypeptide", "peptide" and "protein" may also include polymers including modifications such as, but not limited to, glycosylation, lipid attachment, sulfation, gamma-carboxylation of glutamic acid residues, hydroxylation and ADP-ribosylation.

The term SAL1 and FRY1 as used herein are interchangeable, as are the terms SAL1 and FRY1, as these terms refer to the same protein and encoding nucleotide sequence.

DETAILED DESCRIPTION OF THE INVENTION

The present invention is based on the discovery that plants with mutations in the SAL1 encoding gene have increased stress tolerance, including increased drought resistant.

The SAL1 protein is bifunctional, with inositol polyphosphate 1-phosphatase activity and 3'(2'),5'—bisphosphate nucleotidase activity, and is involved in the catabolism of $IP_3$ a small molecule implicated in stress signalling. There is a variety of inositol phosphatases, or PTases, which all cleave phosphates from various positions on $IP_3$ molecules. These different activities, despite all resulting in a decrease of $IP_3$, often result in different phenotypes, possibly due to due to different functions of the products of hydrolysis (such as $I(1,4)P_2$ and $I(4,5)P_2$. The phenotypic differences may also be due to the secondary activities of these enzymes that have received less attention, such as the nucleotidase activity of SAL1. In addition, localization and differences in expression levels of the enzymes may affect the phenotypes. Surprisingly, SAL1 has relatively low in vitro activity against $IP_3$ (particularly compared to its nucleotidase activity).

A number of mutants in SAL1 have been isolated and are termed fry1 mutants (fiery1; Ishitani, M., L. M. Xiong, et al. (1997), "Genetic analysis of osmotic and cold stress signal transduction in *Arabidopsis*: Interactions and convergence of abscisic acid-dependent and abscisic acid-independent pathways", *Plant Cell* 9(11): 1935-1949; Xiong, L. M., B. H. Lee, et al. (2001), "FIERY1 encoding an inositol polyphosphate 1-phosphatase is a negative regulator of abscisic acid and stress signaling in *Arabidopsis*", *Genes & Development* 15(15): 1971-1984) or hos2 mutants (high expression of osmotic stress regulated gene expresssion2; Lee, H., L. Xiong, et al. (1999), "Cold-regulated gene expression and freezing tolerance in an *Arabidopsis thaliana* mutant", *The Plant Journal* 17(3): 301-308; Xiong, L., H. Lee, et al. (2004), "A single amino acid substitution in the *Arabidopsis* FIERY1/HOS2 protein confers cold signaling specificity and lithium tolerance", *The Plant Journal* 40: 536-545). As previously reported, these mutants were isolated in a screen for changed expression of the stress response gene RD29A. The fry1-1 mutant has increased expression of RD29A under normal conditions and also after cold, salt and osmotic stress and ABA treatment. This was reported to be due to a point mutation resulting in a stop codon in the sixth exon of the SAL1 protein (At5g63980) resulting in a truncated protein that doesn't contain a conserved α-helix containing a $WD-X_{11}$-GG motif, required for coordination of metal ions and phosphate and also nucleophilic water activation. As a result the protein has no activity against $IP_3$ or PAP. The fry1-1 mutant was reported to have increased stress sensitivity to salt, cold and osmotic stress (Xiong et al, 2001). Stress response gene expression, such as HSP70 (At1g16030), COR15A (At2g42540), KIN1 (At5g15960) and ADH (At1g77120), was also increased in the mutant compared to wild-type in response to stress (Xiong et al, 2001) leading to the belief that SAL1 acts as a negative regulator of stress response pathways. Other fry1 mutants, fry1-2 and fry1-3, were also reported to be null mutants with similar characteristics (Xiong et al, 2001). The hos2-1 mutant is a temperature sensitive mutant whose stress response gene expression is altered under low temperature and is cold stress sensitive (Xiong et al, 2004). This mutant's gene expression is not altered under normal conditions or by osmotic or ABA stress, compared to wild type plants (Lee et al, 1999). Drought, salinity, light, cold or heat tolerance has not been reported in either the fry1 or hos2 mutants.

The present inventors have previously isolated the *Arabidopsis thaliana* mutant, alx8, in a mutant screen for altered induction of the antioxidant enzyme ascorbate peroxidase 2 (APX2) under normal conditions and after high light stress. The alx8 mutant had increased APX2 expression under both conditions as well as altered leaf morphology and increased drought tolerance (Rossel, J. B., P. B. Walter, et al. (2006), "A mutation affecting ASCORBATE PEROXIDASE 2 gene expression reveals a link between responses to high light and drought tolerance", *Plant, Cell and Environment* 29(2): 269-281). These characteristics were found to be co-segregating, indicating they were the result of a single point mutation. It was also found that alx8 had altered expression of a number of stress response genes indicating differential regulation of the multiple pathways involved in signalling the drought stress response in *Arabidopsis*. However, the nature of this mutant has not until now been determined. After positional cloning of the mutant it has been discovered that the mutation lies in the previously characterised SAL1 gene. Investigations into the null mutant of this gene, fry1-1, now indicate that it also has increased drought tolerance. Another *Arabidopsis thaliana* mutant, designated salk_020882, which comprises an approximately 10 kb T-DNA insert in the SAL1 gene has also now been studied and found to have increased drought tolerance relative to wild-type plants. Hence, there is potential to improve drought tolerance of agriculturally-important plant species by modifying expression of this gene.

Thus, the present invention provides a method for obtaining a plant with increased stress resistance relative to a wild-type plant, comprising: (a) introducing at least one mutation or exogenous nucleic acid into the genome of one or more plant cells which results in reduced activity associated with SAL1 or a homologue thereof in said one or more plant cells; (b) generating one or more plants from said one or more plant cells; and (c) selecting one or more plants that have increased stress resistance relative to a wild-type plant. According to an embodiment, the method comprises introducing at least one mutation into the SAL1 gene or a homologue thereof, or inhibiting or suppressing the expression of the SAL1 gene or a homologue thereof.

A mutation which results in reduced activity associated with SAL1 or a homologue thereof in said one or more plant cells may be introduced into the one or more plant cells by any appropriate methods as are known in the art. For example, suitable methods may comprise exposing the one or more plant cells (which may be plant seed cells, or cells of a part of a plant, as well as isolated plant cells) to chemical or physical mutagenic means, or insertional mutagenic means such as transposons, retrotransposons, retroviruses, or T-DNA. Suitable materials and methods for introducing mutations into a plant genome are also described in, for example, International patent publication WO 98/26082, "*Arabidopsis* Protocols" ($2^{nd}$ Edition, Salinas, J. and Sanchez-Serrano, J., eds, Methods in Molecular Biology 323 (2006), Humana Press), and "Current Protocols in Molecular Biology" (Ausubel et al. (eds), John Wiley & Sons (2000)), herein incorporated by reference.

The mutation may also be introduced into the one or more plant cells by crossing a wild-type plant with a plant comprising the mutation (as determined previously by genetic screening and/or analysis—plants comprising a desired mutation may already exist in available plant germplasm/culture/seed collections/varieties), and plants may be generated from the resulting seed and then screened for inheritance of the mutation.

According to an embodiment of the invention, a mutation is introduced into a nucleotide sequence encoding SAL1 or a homologue thereof in said one or more plant cells, and may comprise an insertion, deletion or substitution of one or more nucleotides in the nucleotide sequence encoding SAL1 or a homologue thereof. In one embodiment the mutation is a SAL1 null mutation. Alternatively, the mutation may result in an expressed product which, however, has at least reduced activity associated with SAL1 or a homologue thereof. SAL1 mutations identified in the course of the present studies which result in at least increased drought resistance of *Arabidopsis thaliana* plants, relative to wild-type plants include the fry1-1 alx8 and salk_020882 mutant. The fry1-1 mutation results in a change of the 341$^{st}$ amino acid from tryptophan to a stop codon, resulting in a truncated protein missing an α5 helix which is required for enzyme activity (At5g63980). The alx8 mutant has a point mutation comprising a guanine to adenine change at the 1226$^{th}$ base pair of the At5g63980.1 genomic sequence (TAIR Sequence:4010730406 (17 Apr. 2007), Accession#:NM_125794.4: position 1226 of SEQ ID NO:1). The alx8 mutant expresses a mutant SAL1 protein, comprising an amino acid change of glycine to aspartic acid at the 217$^{th}$ amino acid of the amino acid sequence (TAIR Sequence 4010745380 (Aug. 16, 2007); Accession #: NP_201203.2; SEQ ID NO:2), and the salk_020882 mutant comprises an approximately 10 kb T-DNA insertion either between positions 734 and 735 of SEQ ID NO:1 or replacing nucleotides 735 to 745 of SEQ ID NO:1. Additional mutants expected to have increased stress resistance, including increased drought resistance are the fry1-2, fry1-3 and hos2-1 mutants. The fry1-2 mutant comprises a guanine to adenine mutation at the 736$^{th}$ base pair of the At5g63980.1 genomic sequence (TAIR Sequence: 4010730406, Accession#:NM_ 125794.4: position 736 of SEQ ID NO:1) that results in replacement of the glutamic acid residue at position 126 (SEQ ID NO:2) to a lysine resulting in an inactive protein. The fry1-3 mutant comprises a 6.7 kb T-DNA insertion between the fifth and sixth exons at the 1518$^{th}$ base pair of the At5g63980.1 genomic sequence (TAIR Sequence: 4010730406, Accession#:NM 125794.4: position 1518 of SEQ ID NO:1) that results in no RNA transcript. The hos2-1 mutant comprises a cytosine to thymine mutation at the 731$^{st}$ base pair of the At5g63980.1 genomic sequence (TAIR Sequence: 4010730406, Accession#:NM 125794.4: position 731 of SEQ ID NO:1) that results in replacement of the alanine residue at position 124 (SEQ ID NO:2) to a valine resulting in an expressed protein with temperature-sensitive activity.

Other mutants of SAL1, or homologues thereof, may be obtained or generated by no more than routine experimentation based on the teachings provided herein and, for example, the high degree of conservation this nucleotide sequence (and encoded protein) shows—see, for example, FIGS. 5 and 6.

The methods of the present invention can employ any mutagenic agent known in the art (employing methods also known in the art) including, but not limited to ultraviolet light, X-ray radiation, gamma radiation or fast neutron mutagenesis, N-ethyl-N-nitrosourea (ENU), methylnitrosourea (MNU), procarbazine (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6-MP), mitomycin-C (MMC), N-methyl-N'-nitro-N-nitrosoguanidine (MNNG), $^3H_2O$, and urethane (UR).

The frequency of genetic modification upon exposure to one or more mutagenic agents can be modulated by varying dose and/or repetition of treatment, and can be tailored for a particular application. In one embodiment, the treatment dose and regimen does not induce substantial cytotoxicity to the one or more cells.

Mutations in SAL1 or homologues thereof can be detected and followed (through generations) by probing with known SAL1 DNA sequences using techniques well known in the art and suitable probes or primers based on the gene or nucleotide sequence encoding SAL1 or homologue thereof. If the mutation is in a gene other than SAL1, the mutation may need to be identified, located and/or characterised before it can be traced/followed through plant generations. Suitable methods for identifying, locating and characterising unknown mutations are know to those in the art and are described in a number of well-known standard texts, such as Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000). See also Rossel, J. B., Cuttriss, A. and Pogson, B. J. "Identifying Photoprotection Mutants in *Arabidopsis thaliana*" in Methods in Molecular Biology 274: 287-299 (Carpentier, R. ed, Humana Press). More recent methods for identifying mutant alleles include 'Tilling' and high resolution melts (HRMs).

TILLING (Targeting Induced Local Lesions in Genomes) is a method in molecular biology that allows directed identification of mutations in a specific gene. The method combines a standard technique (for example, mutagenesis with a chemical mutagen such as Ethyl methanesulfonate (EMS)) with a sensitive DNA screening-technique that identifies single base mutations (also called point mutations) in a target gene. The first paper describing TILLING in *Arabidopsis* (McCallum C M, Comai L, Greene E A, Henikoff S, "Targeted screening for induced mutations", *Nat Biotechnol*. (2000) April; 18(4):455-7, hereby incorporated by cross-reference) used dHPLC HPLC to identify mutations. The method was made more high throughput by using the restriction enzyme Cel-I combined with a gel based system to identify mutations (Colbert T, Till B J, Tompa R, Reynolds S, Steine M N, Yeung A T, McCallum C M, Comai L, Henikoff S, "High-throughput screening for induced point mutations", *Plant Physiol*. (2001) June; 126(2):480-4, also hereby incorporated by cross-reference). Other methods of mutation detection, such as resequencing DNA, have been combined for TILLING. TILLING has since been used as a reverse genetics method in other organisms such as zebrafish, corn, wheat, rice, soybean, tomato and lettuce. See also: McCallum C M, Comai L, Greene E A, Henikoff S. "Targeting induced local lesions in genomes (TILLING) for plant functional genomics" *Plant Physiol*. (2000) June; 123(2):439-42; Colbert T, Till B J, Tompa R, Reynolds S, Steine M N, Yeung A T, McCallum C M, Comai L, Henikoff S. High-throughput screening for induced point mutations", *Plant Physiol*. (2001) June; 126 (2):480-4; Draper B W, McCallum C M, Stout J L, Slade A J, Moens C B, "A high-throughput method for identifying N-ethyl-N-nitrosourea (ENU)-induced point mutations in zebrafish", *Methods Cell Biol*. (2004); 77:91-112; and Slade A J, Fuerstenberg S I, Loeffler D, Steine M N, Facciotti D, "A reverse genetic, nontransgenic approach to wheat crop improvement by TILLING", *Nat Biotechnol*. (2005) January; 23(1):75-81, also hereby incorporated by cross-reference.

HRM (High Resolution Melt) is a recent development that can greatly extend the utility of traditional DNA melting analysis by taking advantage of recent improvements in high resolution melt instrumentation and the development of double strand specific DNA (dsDNA) binding dyes that can be used at high enough concentrations to saturate all double stranded sites produced during PCR amplifications (see Dufresne S D, Belloni D R, Wells W A, Tsongalis G J, "BRCA1 and BRCA2 Mutation Screening using SmartCyclerII high-resolution melt curve analysis", *Arch Pathol Lab Med* (2006) 130: 185-187; Graham R, Liew M, Meadows C, Lyon E, Wittwer C T, "Distinguishing different DNA heterozygotes by high resolution melting", *Clinical Chemistry* (2005) 51: 1295-1298; Hermann M G, Durtschl J D, Bromley K, Wittwer C T, Voelkerding K V, "Amplicon DNA melting analysis for mutation scanning and genotyping: cross-platform comparison of instruments and dyes", *Clinical Chemistry* (2006) 52: 494-503; Liew M, Pryor R, Palais R, Meadows C, Eraii M, Lyon E, Wittwer C, "Genotyping of single nucleotide polymorphisms by high resolution melting of small amplicons", *Clinical Chemistry* (2004) 50: 1156-1164; Margraf R L, Mao R, Highsmith W E, Holtegaard L M, Wittwer C T, "Mutation Scanning of the RET protooncogene using high resolution melting analysis", *Clinical Chemistry* (2006) 52: 138-141; NGRL (Wessex) Reference Reagent Report, White H, Mattocks, C, Potts, G and Owen N, January 2006, "Plasmid based generic mutation detection reference reagents; production and performance indicator field trial"; NGRL (Wessex) Reference Reagent Report, White H, Potts, G and Durston V, January 2006. "Production and field trial evaluation of reference reagents for mutation screening of BRCA1, BRCA2, hMLH1 and MHS2"; NGRL (Wessex) Reference Reagent Report, White H and Potts, G, June 2006, "Mutation Scanning by High Resolution Melts: Evaluation of Rotor-Gene™ 6000 (Corbett Life Science), HR-1™ and 384 well Light-Scanner™ (Idaho Technology)"; Reed G H, Wittwer C T, "Sensitivity and specificity of single-nucleotide polymorphism scanning by high resolution melting analysis", *Clinical Chemistry* (2004) 50: 1748-1754; Willmore-Payne C, Holden J A, Tripp S, Layfield L J, "Human malignant melanoma: detection of BRAF- and c-kit-activating mutations by high-resolution amplicon melting analysis", *Human Pathology* (2005) 36:486-493; Wittwer C T, Reed G H, Gundry C N, Vandersteen J G, Pryor R J, "High-resolution genotyping by amplicon melting analysis using LCGreen" *Clinical Chemistry* (2003) 49: 853-860; Worm J, Aggerholm A, Guldberg P, "In-tube DNA methylation profiling by fluorescence melting curve analysis" *Clinical Chemistry* (2001) 47: 1183-1189; Zhou L, Myers A N, Vandersteen J G, Wang L, Wittwer C T, "Closed-tube genotyping with unlabeled oligonucleotide probes and a saturating DNA dye", *Clinical Chemistry* (2004) 50: 1328-1335; and Zhou L, Wang L, Palais R, Pryor R, Wittwer C T, "High-resolution DNA melting analysis for simultaneous is mutation scanning and genotyping in solution", *Clinical Chemistry* (2005) 51: 1770-1777.

Oligonucleotide primers can be designed or other techniques can be applied to screen lines for mutations/insertions in the SAL1 gene or homologue thereof. Through breeding, a plant line may then be developed that is homozygous for the mutated copy of the SAL1 gene or homologue thereof. PCR primers for this purpose may be designed so that a large portion of the coding sequence of the SAL1 gene (or homologue thereof) is specifically amplified using the sequence of the SAL1 gene or homologue from the species to be probed (see, for example, Baumann, E. et al. (1998), "Successful PCR-based reverse genetic screens using an En-1-mutagenised *Arabidopsis thaliana* population generated via single-seed descent", *Theor. Appl. Genet.* 97:729 734).

Other SAL1-like mutants may be isolated from mutant populations or existing germplasm using the distinctive phenotypes characterized in accordance with the present invention (such as drought tolerance, reduced SAL1-associated activity, or changes to gene expression compared to the wild-type plants). After a suitable growth period and application of a suitable abiotic stress, such as withholding water, plants may be screened for the phenotype of the SAL1 mutant. That the phenotype is caused by a mutation in SAL1 or a homologue thereof may then be established by molecular means well known in the art.

SAL1-like mutants, including mutants heterozygous for the allele, and which may not express the stress-resistant phenotype, may also be screened for, as described later, and the mutants used for breeding programs to introgress the mutation into homozygous line, or the mutant gene isolated and used in recombinant techniques for generating mutant plants.

While mutants of the present invention may be generated by random mutagenesis (or may already exist), any plant may be recombinantly engineered to display a similar phenotype, for example once the genetic basis of the mutation, such as a mutated SAL1 gene, has been determined. For a general description of plant transformation and regeneration see, for example, Walbot et al. (1983) in "Genetic Engineering of Plants", Kosuge et al. (eds.) Plenum Publishing Corporation, 1983 and "Plant Cell, Tissue and Organ Culture: Fundamental Methods", Gamborg and Phillips (Eds.), Springer-Verlag, Berlin (1995). See also Sambrook, J. et al., Molecular Cloning, Cold Spring Harbor Laboratory (1989), Sambrook, J. and Russell, D. W. (2001), *"Molecular Cloning: A Laboratory Manual"*, 3rd edition, Cold Spring Harbor Laboratory Press, and references cited therein and Ausubel et al. (eds) Current Protocols in Molecular Biology, John Wiley & Sons (2000).

For example, a method of the invention may comprise inserting into said one or more plant cells exogenous nucleic acid which inhibits expression of the activity of endogenous SAL1 or homologue thereof (for example, via regulatory regions controlling expression of SAL1 or a homologue thereof, the SAL1-encoding sequence or a homologue thereof, or mRNA translated from the SAL1-encoding sequence or a homologue thereof), or which replaces expression of endogenous SAL1 or homologue thereof with expression of an exogenous protein. The exogenous protein may be an exogenous mutant SAL1 or homologue thereof, or any other suitable protein, such as a protein providing a screenable phenotype.

In one embodiment the exogenous nucleic acid may comprise an oligonucleotide or polynucleotide which introduces a mutation comprising single or multiple nucleotide insertions, deletions or substitutions into the endogenous nucleotide sequence encoding SAL1 or a homologue thereof via homologous recombination.

Single or multiple nucleotide insertions, deletions or substitutions may be introduced via recombination of the target mutation site with an introduced targeting nucleotide sequence. Such an introduced nucleotide sequence may, for example, comprise a nucleotide sequence to be introduced into the genome flanked either side by nucleotide sequences homologous to target sequences contiguous in or located either side of a desired mutation insertion point. In accordance with the methods of the present invention, a nucleotide sequence to be introduced into the genome may also include a selectable marker operably linked to desired regulatory regions (which may include, for example, a stress-inducible promoter).

The nucleotide sequences homologous to the target sequences may be isogenic with the target sequences to thereby promote the frequency of homologous recombination.

Homologous nucleotide sequences that are not strictly isogenic to the target sequences can also be used. Although mismatches between the homologous nucleotide sequences and the target sequences can adversely affect the frequency of homologous recombination, isogenicity is not strictly required and substantial homology may be sufficient. For the purposes of the present invention, the level of homology between the homologous sequences and the target sequences may be at least about 90% identity, at least about 95% identity, at least about 99% identity or 100% identity.

A targeting nucleotide sequence can be comprised in a vector. Representative vectors include plasmids, cosmids, and viral vectors. Vectors can also comprise nucleic acids including expression control elements, such as transcription/translation control signals, origins of replication, polyadenylation signals, internal ribosome entry sites, promoters, enhancers, etc., wherein the control elements are operatively associated with a nucleic acid encoding a gene product. Selection of these and other common vector elements are conventional and many such sequences can be derived from commercially available vectors. See, for example, Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000).

A targeting vector can be introduced into targeting cells using any suitable method known in the art for introducing DNA into cells, including but not limited to microinjection, electroporation, calcium phosphate precipitation, liposome-mediated delivery, viral infection, protoplast fusion, and particle-mediated uptake.

Optionally, a targeting DNA is co-administered with a recombinase, for example recA, to a target cell to thereby enhance the rate of homologous recombination. The target cell(s) may already comprise, or have been transformed to comprise suitable recombinase target sequences, if required. For example, a recombinase protein(s) can be loaded onto a targeting DNA as described in U.S. Pat. No. 6,255,113. To enhance the loading process, a targeting DNA can contain one or more recombinogenic nucleation sequences. A targeting DNA can also be coated with a recombinase protein by pre-incubating the targeting polynucleotide with a recombinase, whereby the recombinase is non-covalently bound to the polynucleotide. See, for example, A. Vergunst et al (1998), *Nucleic Acids Res.* 26:2729 and A. Vergunst and P. Hooykaas (1998), *Plant Molec. Biol.* 38:393 406, International patent publications WO 99/25821, WO 99/25840, WO 99/25855, and WO 99/25854 and U.S. Pat. Nos. 5,780,296, 6,255,113, and 6,686,515.

According to an alternative embodiment for carrying out a method of the invention, a plant with increased stress resistance, relative to a wild-type plant, may be created by inhibiting translation of SAL1 mRNA (or homologue thereof) by RNA interference (RNAi), antisense or post-transcriptional gene silencing techniques. The SAL1 gene or homologue thereof from the species targeted for down-regulation, or a fragment thereof, may be utilized to control the production of the encoded protein. Full-length antisense molecules can be used for this purpose. Alternatively, double stranded oligonucleotides, to sense and/or antisense oligonucleotides, or a combination thereof targeted to specific regions of the SAL1-encoded RNA may be utilized. The use of oligonucleotide molecules to decrease expression levels of a pre-determined gene is known in the art (see, for example, Hamilton, A. J. and Baulcombe, D. C. (1999), "A species of small antisense RNA in posttranscriptional gene silencing in plants", *Science* 286: 950-952; Waterhouse P. M. et al (1998), "Virus resistance and gene silencing in plants can be induced by simultaneous expression of sense and antisense RNA", *Proc. Natl. Acad. Sci. USA* 95:13959-13964; and International patent publications WO 99/53050, WO 99/49029, WO 99/32619). Oligonucleotide molecules may be provided in situ by transforming plant cells with a DNA construct which, upon transcription, produces double stranded and/or antisense RNA sequences, which may be full-length or partial sequences. The gene silencing effect may be enhanced by over-producing both sense and/or antisense sequences (which may be full-length or partial) so that a high amount of dsRNA is produced.

Transgenic plants with one of the transgenes mentioned above can be generated using standard plant transformation methods known to those skilled in the art including, for example, *Agrobacterium*-mediated transformation, cation or polyethylene glycol treatment of protoplasts, electroporation, microparticle bombardment, agitation of cell suspensions in solution with microbeads or microparticles coated with the transforming DNA, direct DNA uptake, liposome-mediated DNA uptake, and the like, as also described in a wide range of publicly available texts, such as: "Methods for Plant Molecular Biology" (Weissbach & Weissbach, eds., 1988); Clough, S. J. and Bent, A. F. (1998) "Floral dip: a simplified method for *Agrobacterium*-mediated transformation of *Arabidopsis thaliana*" *Plant J.* 16, 735-743; "Methods in Plant Molecular Biology" (Schuler & Zielinski, eds., 1989); "Plant Molecular Biology Manual" (Gelvin, Schilperoort, Verma, eds., 1993); and "Methods in Plant Molecular Biology-A Laboratory Manual" (Maliga, Klessig, Cashmore, Gruissem & Varner, eds., 1994). See also Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000), these references being incorporated herein by cross-reference.

The preferred method of transformation may depend upon the plant to be transformed. *Agrobacterium* vectors are often used to transform dicot species. For transformation of monocot species, biolistic bombardment with particles coated with transforming DNA and silicon fibers coated with transforming DNA are often useful for nuclear transformation. However, *Agrobacterium*-mediated transformation of monocotyledonous species, including wheat, are now known (see, for example, International patent publications WO 97/48814; see also Hiei, Y. et al (1994), *Plant J.* 6(2):271-282 and international patent publication WO 92/06205).

DNA constructs for transforming a selected plant may comprise a coding sequence of interest operably linked to appropriate 5' regulatory sequences (e.g., promoters and is translational regulatory sequences) and 3' regulatory sequences (e.g., terminators). In a preferred embodiment, the coding region is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase (NOS) and octopine synthase (OCS) promoters.

Transgenic plants expressing a sense or antisense SAL1-encoding sequence under an inducible promoter are also contemplated to be within the scope of the present invention. Stress-inducible promoters, such as high-light-, drought-, salinity- or temperature-induced promoters are especially contemplated by the present invention. Promoters which may be used according to the invention may include, for example, the ribulose bisphosphate carboxylase (RuBisCo) small subunit gene promoters or chlorophyll a/b binding protein (CAB) gene promoters for expression in photosynthetic tissue; the various seed storage protein gene promoters for expression in seeds; or the root-specific glutamine synthetase gene promoters for expression in the root system of the transformed plant.

The coding region may also operably linked to an appropriate 3' regulatory sequence. For example, the nopaline synthetase (NOS) polyadenylation region or the octopine synthetase (OCS) polyadenylation region may be used.

Using an *Agrobacterium* binary vector system for transformation, the selected coding region, under control of a constitutive or inducible promoter as described above, may be linked to a nuclear drug resistance marker, such as kanamycin resistance. Other useful selectable marker systems include, but are not limited to: other genes that confer antibiotic resistances (e.g., resistance to hygromycin or bialaphos) or herbicide resistance (e.g., resistance to sulfonylurea, phosphinothricin, or glyphosate).

The methods of the present invention can be used to transform any plant cell. In this manner, genetically modified plants, plant cells, plant tissue, seed, and the like can be obtained. According to one embodiment, the plant cell(s) to be transformed may be selected from economically and/or agronomically important plant families, including the Apiaceae, Asteraceae, Brassicaceae, Chenopodiaceae/Amaranthaceae, Compositae, Cucurbitaceae, Fabaceae, Gramineae, Leguminosae, Poaceae, Rosaceae or Solanaceae.

Cells which have been transformed may be grown into plants in accordance with conventional methods as are known in the art (See, for example, McCormick, S. et al (1986), *Plant Cell Reports* 5:81-84). The resulting plants may be self-pollinated, pollinated with the same transformed strain or different strains or hybridised, and the resulting plant(s) having reduced or inactivated activity associated with SAL1 or a homologue thereof identified. Two or more generations may be grown to ensure that this phenotypic characteristic is stably maintained. Alternatively, in vegetatively propagated crops, mature mutant/transgenic plants may be propagated by cutting or by tissue culture techniques to produce identical plants. Selection of mutant/transgenic plants can be carried out and new varieties may be obtained and propagated vegetatively for commercial use.

Plants transformed/mutated by the methods of the invention may be screened based on the lack of SAL1 protein, or homologue thereof, or of its activity or by increased stress (such as drought) resistance, molecular analysis using specific oligonucleotide probes and/or amplification of the target gene.

According to an embodiment of the invention the resulting plant has increased resistance to drought, salinity, temperature stress, light stress or any other abiotic or biotic stress relative to a wild-type plant, or any combination thereof. According to a specific embodiment of the invention, the resulting plant has at least increased drought resistance relative to a wild-type plant.

In the course of the present studies, mutations affecting activity of SAL1 in plants were also found to affect flowering time, as well as leaf shape, in a characteristic fashion, and to dramatically affect the metabolism of the mutant plants, as compared to the wild-type.

In particular, flowering time was significantly delayed in all SAL1 mutants studied, by about 4-5 weeks for the plants studied (thereby providing a delay in flowering of approximately 100%). Depending on the mutation or exogenous nucleic acid causing the delayed flowering time, and the plant into which the mutation or exogenous nucleic acid is introduced, flowering time may be expected to be delayed by different amounts of time, for example flowering time may be delayed by from about 7 days to about 100 days, such as by about 14 days to about 80 days, by about 21 days to about 60 days, by about 25 days to about 50 days, by about 30 days to about 40 days, by about 10 days, about 20 days, about 25 days, about 30 days, about 35 days, about 40 days, about 45 days, about 50 days, about 60 days, about 80 days or about 100 days. Altered activity of SAL1, including, but not limited to overexpression, may also advance the onset of flowering time by similar time margins.

Leaf shape was also affected significantly, resulting in leaves with increased thickness than those of wild-type plants, and which were also shorter and rounder with more lobed edges. The surface of the leaves observed was often undulating and the petiole length reduced, giving the leaf rosette a lettuce-like appearance. Increased undulation of the leaf surface could increase the boundary layer effect, decreasing transpiration.

Metabolomic analysis revealed that both mutants exhibit a similar, dramatic reprogramming of metabolism, including increased levels of the stress tolerance-implicated polyamine, putrescine, and the accumulation of a number of unknown, potential osmoprotectant carbohydrate derivatives.

Plant parts, including but not restricted to leaves, stems, roots, tubers, flowers, fruits and seeds obtained from plants obtained by the methods of the present invention are also provided.

Methods for Detecting Mutations in SAL1 or Homologues Thereof

Screening a plant for the presence of at least one mutant allele of a nucleotide sequence encoding SAL1 or a homologue thereof, may comprise analysing DNA of the plant using at least one nucleic acid molecule suitable as a probe or primer which is capable of hybridising to a SAL1 gene or homologue thereof under stringent conditions. In a more specific method, the screening method may comprise the use of at least one oligonucleotide primer pair suitable for amplification of a region of the SAL1 gene or homologue thereof, comprising a forward primer and a reverse primer to detect the presence or absence of a mutation in said region. The region may comprise the whole SAL1 gene or homologue thereof, or may comprise only a portion thereof, such as, for example (and referring to FIG. 10), the nucleotide region comprising exon 3, the intron betweens exons 3 and 4, exon 5, the intron between exons 5 and 6, exon 6, and the intron between exons 6 and 7, or any combination thereof.

DNA from the subject to be assessed may be extracted by a number of suitable methods known to those skilled in the art, such as are described in a wide range of well known texts, including (but not limited to) Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000), incorporated herein by cross-reference. See also the methods described in Lukowitz, W., Gillmor, C. S, and Scheble, W-R. (2000) "Positional Cloning in *Arabidopsis*: Why It Feels Good to Have a Genome Initiative Working for You" *Plant Physiology* 123, 795-805, and references cited therein.

Once suitable DNA has been isolated, this may be analysed for the presence or absence of a mutation by any suitable method as known in the art, and which method/strategy is employed may depend on the specificity desired, and the availability of suitable sequences and/or enzymes for restriction fragment length polymorphism (RFLP) analysis. Suitable methods may involve detection of labelled hybridisation product(s) between a is mutation-specific probe and at least a portion of the SAL1 gene or homologue thereof or, more typically, by amplification of at least a portion of the SAL1 gene or homologue thereof using either a primer and suitable probe, or using a pair of primers (forward and reverse primers) for amplification of a specific portion of the SAL1 gene or homologue thereof, followed by either direct partial and/or complete sequencing of the amplified DNA, or RFLP analysis thereof. Suitable primer pairs for amplifying portions of the SAL1 gene are provided in Table 1 (see also FIG. 10)—other suitable primers or primer pairs for analysing the SAL1 gene or homologues thereof may be designed based on the SEQ ID NO:1, the sequence provided for At5g63980 (TAIR Sequence: 4010730406, Accession No: NM_125794.4) or homologues thereof (see, for example, FIG. 6B).

The methods and reagents for use in a PCR amplification reaction are well known to those skilled in the art. Suitable protocols and reagents will largely depend on individual circumstances. Guidance may be obtained from a variety of sources, such as for example Sambrook, J. et al., Molecular Cloning, Cold Spring Harbor Laboratory (1989), Sambrook, J. and Russell, D. W. (2001), "*Molecular Cloning: A Laboratory Manual*", 3rd edition, Cold Spring Harbor Laboratory Press, and references cited therein and Ausubel et al. (eds) Current Protocols in Molecular Biology, John Wiley & Sons (2000), incorporated herein by cross-reference.

A person skilled in the art would readily appreciate that various parameters of the PCR reaction may be altered without affecting the ability to amplify the desired product. For example the $Mg^{2+}$ concentration and temperatures employed may be varied. Similarly, the amount of genomic DNA used as a template may also be varied depending on the amount of DNA available.

s Other methods of analysis of the amplified DNA to determine the presence or absence of a mutation are well known to those skilled in the art. For instance, following digestion of the amplified DNA with a suitable restriction enzyme to detect a mutation in the SAL1 gene or homologue thereof, the DNA may be analysed by a range of suitable methods, including electrophoresis. Of particular use is agarose or polyacrylamide gel electrophoresis, a technique commonly used by those skilled in the art for separation of DNA fragments on the basis of size. The concentration of agarose or polyacrylamide in the gel in large part determines the resolution ability of the gel and the appropriate concentration of agarose or polyacrylamide will therefore depend on the size of the DNA fragments to be distinguished.

Detection and/or determination of the existence of a mutation in the SAL1 gene or homologue thereof may be aided by computer analysis using any appropriate software. Suitable software packages for comparison of determined nucleotide sequences are well known in the art and are readily available.

Preferred forms of the present invention will now be described, by way of example only, with reference to the following examples, including comparative data, and which are not to be taken to be limiting to the scope or spirit of the invention in any way.

EXAMPLES

Example 1

Materials and Methods

Plants and Growth Conditions

*Arabidopsis* seed already transformed with the APX2 promoter-luciferase reporter gene (APX2:LUC) construct (Karpinski, S. et al (1999), *Science* 284: 654-657) was mutagenised with ethylmethane sulfonate (EMS) and M2 plants screened in pools derived from 500 M1 parents (see Ball, L. et al (2004), *Plant Cell* 16: 2448-2462). The mutant screen was carried out using a luminescence counter to count photons emitted per seedling in 96-well microtitre plates as described in Rossel, J. B. et al (2004), *Methods in Molecular Biology* 274: 287-300. To confirm the reproducibility of the altered APX2 expression, four-week old *Arabidopsis* plants containing APX2:LUC were imaged using a cooled CCD camera (Model DV 435, Andor Technology, Tokyo, Japan). Prior to imaging, the plants were sprayed with a 1 mM D-luciferin (BIOSYNTH, Staad, Switzerland) solution containing a few drops of Tween® 80 and left in growth light conditions for 5 min. Images obtained using the CCD camera were analysed using Image-Pro software (Media Cybernetics; Carlsbad, Calif., USA). Several mutants with altered APX2:LUC expression were identified, including mutant alx8 which had increased APX2:LUC expression, and which also showed increased drought tolerance, as well as altered leaf shape.

Seed stock for the fry1-1 null mutant, the salk_020882 insertion mutant and wild-type (WT) Columbia plants were obtained from The *Arabidopsis* Biological Resource Centre (Columbus, Ohio). All references to WT here in refer to the Columbia ecotype; salk1 and salk2 refer to two identical plants from the T3 generation of the seed stock of the salk_020882 line. The fry1-1 mutant is in the C24 wild-type background and is the third back-cross.

For growth in soil, in early experiments a few *Arabidopsis* seeds were sprinkled on sterilised soil (1 part vermiculite to 4 parts soil) in pots (4 cm×4 cm×6 cm), and in later experiments the plants were grown on metro mix soil (35% Canadian peat moss, 19% perlite 500, 40% vermiculite, 1.5 $g.L^{-1}$ lime). The seeds were vernalised at 4° C. in the dark for 72 to 96 hours. Seedlings were then transferred to a growth chamber with a 12 hour light/12 hour dark cycle at 100-160 µmol photons. $m^{-2}.s^{-1}$ at approximately 21+/−2° C. A short day cycle was chosen to promote vegetative growth. To promote flowering plants were grown in the same conditions but with 16 hour days. Cling wrap was used to keep the environment humid until seedlings were established. Seedlings were thinned out to one per pot except for mapping populations, which were grown two per pot. Plants were fertilised with 0.5× Hoaglands media once a fortnight (Hoaglands and Amon, 1950). Trays were also rotated from the edges to the centre of the light bank to maintain similar growth conditions for all plants. Also, where possible, plants for the same experiment were grown side-by-side in the same tray, such that they experience the same growth conditions.

For seeds germinated on tissue culture media, surface sterilisation was done in a laminar flow. Seeds were placed in a 1.5 mL Eppendorf® tube and washed with 1 mL of 70% ethanol for 3 minutes. Seeds were spun down in a benchtop centrifuge (14,000 rpm) for 30 seconds and the ethanol removed. Seeds were resuspended and washed in 1 mL of bleach solution (3% sodium hypochlorite, 75% $H_2O$+1 drop Tween® 20 detergent) for 5 minutes. The seeds were spun down as before. Five washes and centrifugation steps were done using 1 mL of sterile water each wash, discarding the water after each spin. The seeds were resuspended in sterile water before being plated out on Murashige and Skoog (MS) (GibcoBRL, USA) plant nutrient agar. MS agar was made up of the following: 4.3 g/L MS salts, 20 g/L sucrose, 1 mL/L vitamins, 7 g/L phytagar, pH adjusted to 5.8 with KOH, in MilliQ treated water. Where selection was required, antibiotics were incorporated in the agar: 30-50 µg/mL kanamycin (MP Biomedical, Solon, Ohio, USA), or 30 µg/mL hygromycin (GibcoBRL). Plates were wrapped in aluminium foil and placed at 4° C. for 72 hours for vernalisation, then either placed in the growth cabinet at 21° C. under 24 hour light at 100 µmol photons.m$^{-2}$.$^{s-1}$ or grown under the same conditions as plants in soil.

Stress Conditions

For drought stress experiments trays were set out under normal growth conditions and biological replicates were distributed randomly across the trays and rotated every two days to control for variability of light intensity, temperature and air exposure across light banks. Plants were watered the day before treatment and at t=0 water excess water was poured out of the trays, meaning plants started the drought experiment at 100% relative soil water content. Individual pots were weighed each day to get a relative water loss % calculated as:

$$\frac{(\text{initial weight(g)} - \text{current weight(g)}) \times 100}{\text{initial weight(g)}} = \text{relative soil water loss (\%)}$$

For cold stress, plants grown in soil were exposed to 24 hours of cold stress (4° C.) with 1 µmol photons.m$^{-2}$.s$^{-1}$ of light.

For salt stress, plants grown in soil were watered from beneath with NaCl solution once every two days.

Stress Treatments of Plants Grown on Media

Seeds were sterilised as normal before being plated out on media containing appropriate concentrations of sucrose, mannitol, LiCl, NaCl or methyl viologen. Plates were then vernalised and grown as normal. Effects on germination and seedling growth were observed.

DNA Manipulations

*Arabidopsis* DNA extractions

Rough DNA Extraction

To a small amount of plant tissue, 40 µL of 0.25M NaOH was added. The sample was grinded using a yellow P20 tip till the pigment went into solution. Samples were heated to 100° C. for 30 seconds before 40 µL of 0.25M HCl and 204 of 0.5M Tris-HCl, pH8 with 0.25% Triton® X-100 was added. Samples were mixed by inversion then heated to 100° C. for 2 minutes.

Extraction Method for DNA

This extraction was adapted from Weigel and Glazebrook, *Arabidopsis*: a laboratory manual, (Cold Spring Harbor Press, 2002). Tissue and extraction buffer (200 mM Tris-HCl pH 7.5, 250 mM NaCl, 25 mM EDTA, 0.5% SDS) were shaken in 2 mL tubes using a paint shaker and two glass beads. This ground and lysed the tissue. This was then centrifuged at maximum speed for 5 minutes in a microcentrifuge, and 300 µl of supernatant was transferred to a 1.5 mL Eppendorf® tube. 300 µl of isopropanol was added to precipitate the DNA and the DNA was then pelleted by centrifugation at maximum speed (Eppendorf® centrifuge) for 5 minutes. The supernatant was discarded and the pellet washed with 70% ethanol. The DNA was then dissolved in 100 µl of TE (10 mM Tris-HCl pH 8.0, 1 mM EDTA).

CTAB extraction of DNA

A small amount of plant tissue, either leaf or inflorescence, was harvested from each plant. 300 µl of CTAB buffer (2% (w/v) cetyl-trimethyl-ammonium bromide (CTAB), 1.4M NaCl, 100 mM Tris HCl pH8.0, 20 mM EDTA) was added to each sample along with a ⅛" steel ball bearing. Samples were then lysed in a TissueLyser® (Qiagen, Hilden, Germany) for 2 minutes at a frequency of 30/sec. Samples were then incubated at 65° C. for between 30 minutes and several hours. Samples were allowed to cool before adding 300 µl of chloroform and vortexing thoroughly. Samples were spun down at 14,000 rpm for 1 minute and the upper aqueous layer transferred to a new Eppendorf® tube. 3000 of isopropanol was added to each sample and mixed by inversion several times. Samples were spun down at 14,000 rpm for 5 min to form a pellet. The supernatant was poured off and the pellet was washed with 500 µl 70% ethanol. Samples were air-dried then dissolves in 100 µl TE buffer (10 mM Tris HCl pH8.0, 1 mM EDTA).

Adaptations for 96-Well Format

The CTAB extraction method was adapted for use in 96-well plates by centrifugation of precipitated DNA by a benchtop 4-15° C. centrifuge with plate holders (Qiagen, Hilden, Germany) and the use of multi-channel, multi-dispensing pipettes.

PCR Amplification and Gel Electrophoresis

Primer Design

Other than those referenced to a paper, primers were designed using sequences published on the TAIR website. Primers were designed using the following conditions: 50 mM salt concentration; GC content approximately 50%; maximum self-complementarity of 8; and maximum 3' self-complementarity of 3. Generally primers had a Tm of 55-60° C. and were around 20 bp long. The possibility of the primers binding and amplifying other products was tested by using BLASTn for 'short, nearly exact matches' on the NCBI website.

Examples of primers (forward—F—and reverse—R) used for amplification and sequencing are provided in Table 1 and a scale depiction of the SAL1 gene, showing introns, exons, primer hybridisation locations, as well as the location of the fry1-3 and salk_020882 T-DNA insertions, the fry1-1, fry1-2 and the alx8 mutations is provided in FIG. 10.

TABLE 1 primers for amplification of portions of the SAL1 gene

| Primer Name | Sequence 5'-3' | $T_m$ (° C.) |
|---|---|---|
| 1F (SEQ ID NO: 5) | CGGACGCAAGTCTTCTTCTC | 60.13 |
| 1R (SEQ ID NO: 6) | CCACCAATGAAAAGGGTTCA | 60.72 |
| 2F (SEQ ID NO: 7) | CCAGTGACCGTTGCTGATTA | 59.72 |
| 2R (SEQ ID NO: 8) | TGAAAATGCTCAGTGTCAGGA | 59.43 |
| 3F (SEQ ID NO: 9) | ACACTTTGGCTACCGAGGAA | 59.73 |
| 3R (SEQ ID NO: 10) | GTGGAGCTTTGACACCGAGT | 50.31 |
| 4F (SEQ ID NO: 11) | TTCTCCTGTAAAAGTGCAAGTCTC | 59.13 |
| 4R (SEQ ID NO: 12) | TGGTGAAATTCGGTGAAAGA | 59.10 |
| 5F (SEQ ID NO: 13) | TGGCTTACGAGAAAGAGCTTG | 59.78 |
| 5R (SEQ ID NO: 14) | AGCAAAGAAGAGGCATCCAA | 59.96 |
| 6F (SEQ ID NO: 15) | CTGAGGGGAGATCAATACGC | 5965 |

TABLE 1-continued primers for amplification of portions of the SAL1 gene

| Primer Name | Sequence 5'-3' | $T_m$ (° C.) |
|---|---|---|
| 6R (SEQ ID NO: 16) | TGCTCAGCTATGGAGTCACG | 60.16 |
| proF (SEQ ID NO: 17) | ACACGCCATCATCAATCTA | 54.85 |
| 1-2R (SEQ ID NO: 18) | CCCTTTATACTTAGCCCAAA | 54 |
| FRY1exon1F (SEQ ID NO: 19) | ACTCGCTGCTCGTCTCTGTC | 60.00 |
| realtimeFRY1R (SEQ ID NO: 20) | AGAACGATGCCTCTTCAGGA | 59.95 |

For SSLP mapping, primers were designed around InDels as published in the Monsanto SNP and Ler Collections on the TAIR website. Some polymorphisms were also found in the TAIR polymorphism database. Primers were designed to produce a 200-300 bp product and to have a Tm of 57° C. Sequence for the region was taken from the appropriate BAC. For SNP dCAPS primers were designed using the online program dCAPS Finder 2.0 (Neff et al, 2002), the appropriate BAC sequence and Primer 3. dCAPS Primers specific for the alx8 mutant (which create a restriction site in the alx8 mutant product but not in the wildtype, and which is recognized by the XbaI restriction enzyme) were as follows: F: 5'-GAG-GAAGGGAAAGTAGTTCTAG-3' (SEQ ID NO: 21); R: 5'TGCACTITTACAGGAGAAGA-3' (SEQ ID NO:22). The digests were then tested 'in silico' in NEBCutter V2.0; Vinzce et al, 2003).

For recombinant vector construction primers were designed as above but the appropriate spacer and recombination site was added to the 5' end of the primer.

Primers were obtained from Proligo (Lismore, Australia) or Invitrogen (Carlsbad, Calif., USA).

Standard PCR conditions

Standard PCR conditions were used for mapping, confirmation of constructs and screening of segregating populations. All PCR reactions were undertaken in a Peltier Thermal Cycler (MJ Research, BIORAD, Waltham, Mass., USA) or a Palm-Cycler® (Corbett Research, Sydney, Australia). In the event that PCR of a positive control did not produce any product or multiple products, the conditions of amplification were optimised. A temperature gradient with 12 different temperatures was run on the Palm-Cycler®, the $MgCl_2$ content varied from 1-2.5 mM and preference for different Taq polymerases was tested. Reactions generally had the following components: 0.2 mM dNTPs, 1× Taq buffer (as appropriate), 0.5 µM each primer, 2 mM $MgCl_2$ (FisherBiotech, WA, Australia), 1-2 µl sample DNA and 0.25 U Taq (as appropriate). Typical cycle conditions were 2 min at 94° C.; 40 cycles of 30 sec at 94° C., 30 sec at $T_m$-2° C. and 30 sec at 72° C.; 2 min at 72° C.

High Fidelity PCR Conditions

For sequencing and construct production a very accurate and/or long PCR product was required. In these cases, proof reading polymerases were used according to the manufacturer's instructions. These were Pfu DNA Polymerase (Promega, Madison, Wis.), Platinum pa Taq Polymerase (Invitrogen, Carlsbad, Calif.) and Phusion® High-Fidelity DNA Polymerase (Finnzyme, Espoo, Finland).

Electrophoresis

For nucleic acid separation and quantification, samples were run on agarose gels with a Precision Molecular Mass Standard Ladder (BioRad, USA) and a 1 kb DNA Ladder (Promega, USA). A homemade ladder of lambda DNA digested with HindIII and EcoRI were also used. For standard PCR, electrophoresis was performed in 0.5-2% (w/v) agarose gels (Fisher Biotech, WA, Australia) with 0.5 ng/mL Ethidium Bromide (Biorad) incorporated in the gel for visualization. When high resolution was required, such as dCAPS separation, 3-4% (w/v) gels were made with Agarose-1000 (GibcoBRL, Invitrogen, Rockville, Md., USA). Gels were made with and run in 1×TBE buffer (89 mM Tris base, 89 mM boric acid, 2 mM EDTA, pH 8.0) or 1×TAE buffer (40 mM Tris-acetate, 20 mM $Na_2EDTA$, pH8.5). Gels were run in a traditional electrophoresis set-up or in the Super 120 High Performance Gel System (6 mgel, Biokeystone, El Monte, Calif., USA), which can be run at up to 300V. For separation of plasmid digest, 0.7-1.0% gels were run for 6 hours at 4° C. at 100V.

Loading buffer (70% glycerol, 30% $H_2O$, bromophenol blue) was added to PCR product before loading. Gels were imaged over a UV light source.

Purification and Gel Extraction of DNA Fragments

Before use in ligations or sequencing, DNA fragments were purified from agarose gel or PCR mix. This process removes primers, nucleotides, enzymes, mineral oil, salts, agarose, ethidium bromide and other impurities.

For small fragments of 70-10 kp the Wizard® SV Gel and PCR Clean-Up System or the QIAquick® Gel Extraction Kit or PCR Clean-Up Kits (Qiagen) was used as per manufacturers instructions. In brief, appropriate bands were cut out of the gel and dissolved in buffer containing guanidine isothiocyanate. The dissolved gel or PCR product was then passed through a column containing a silica membrane in the presence of chaotropic salts. The membrane, which was bound with the DNA, was then washed before the DNA is eluted in sterile $dH_2O$.

For gel extraction of DNA fragments 100 bp-10 kbp, the Ultrafree-DA® Centrifugal Filter Unit (Millipore) was also used as per manufacturer's instructions. This kit differs in that a gel nebuliser utilises gel compression to extract the DNA from the agarose. DNA was then purified by adding 1/10 volume of 3M Na-acetate, mixing, adding 2.5 volumes of 100% ethanol and precipitating the DNA at −20° C. for 3 hours. DNA was pelleted by centrifugation at maximum speed for 15 minutes in a benchtop centrifuge. The pellet was washed with 70% ethanol. The DNA was then dissolved in sterile $dH_2O$.

The QIAEX® II Kit was used for gel extractions of bands known to be larger than 10 kb and was used as per manufacturer's instructions. This kit uses silica beads to bind the DNA rather than a silica membrane, preventing the shearing of larger DNA fragments as it passes through the membrane.

Yields were then quantified using the nanodrop Spectrophotometer (Genomic Solutions, Melbourne, Australia).

Positional Cloning and Complementation is Genomic DNA was extracted from the F2 population of the cross between alx8 (Col-0 background) and wildtype Landsberg erecta. The leaf phenotype of the F2, or their progeny for wildtype F2, was used to determine their genotype at the alx8 mutation site. An initial screening was done with markers described by Lukowitz et al (Lukowitz, W., C. S. Gillmor, et al (2000), "Positional cloning in *Arabidopsis*. Why it feels good to have a genome initiative working for you", Plant Physiology 123(3):795-805). Markers were designed around SSLP and SNPs found in the Cereon database. dCAPS primers were designed with the help of dCAPS Finder 2.0 (Neff et al, 2002). PCR, digestion and gel electrophoresis were performed using standard methods.

Vector Manipulations

Restriction Digest

All enzymes were from Promega and used per manufacturers instructions except for a few modifications. Restriction digests were carried out for fine mapping using dCAPS markers. In this case 10 μl of PCR product was digested with 1 unit of the appropriate enzyme at 37° C. for 1 hour to overnight. Restriction digest of plasmids, such as BACS, were carried out on 1 μg of DNA and 5 units of enzyme. Digestions were stopped by heating at 65° C. for 15 minutes or freezing at −20° C.

Dephosphorylation

Digested fragments were dephosphorylated using Calf Intestine Alkaline Phosphatase (CIAP; Promega) as per manufacturer's instructions. The reaction was repeated twice before being stopped using the supplied stop buffer. The solution was then cleaned by phenol:chloroform:isoamyl alcohol (25:24:1) extraction and a sodium acetate and 100% ethanol precipitation. The pellet was washed in 70% ethanol before being air-dried and resuspended in sterile water.

Vector Ligation

Prepared inserts and plasmids were ligated using T4 ligase (Promega) as per manufacturer's instructions. The ratio of 3:1 of insert:vector DNA was used predominantly over 1:1 or 1:3 ratios and the ligation took place at 4° C. overnight.

Vector Recombinations

For vectors that required recombination the insert was amplified using high fidelity conditions and primers containing the attB recombination sequence. Recombination is reactions were undertaken using the Gateway® system (Invitrogen) as per manufacturer's instructions. In brief, 50 fmol of an appropriate insert was recombined with 50 fmol of the vector pDONR/Zeo (Invitrogen), which contains the corresponding attP recombination sequences, using 2 μl of the BP clonase enzyme in a 10 μl reaction. This is referred to as the BP reaction and results in an attL recombination sequence. The reaction was left at 25° C. overnight, then stopped by incubation with 1-2 μg proteinase K at 37° C. for 10 minutes. After transformation into competent *E. coli* and incubation with selection, the plasmid was purified and the insert was confirmed. The isolated plasmid was then recombined with the destination vector in the LR reaction. Destination vectors, such as pHellsGate 8 (pHG8; donated by Peter Waterhouse and Chris Helliwell, PI, CSIRO), contain the attR recombination sequences. These then recombine with the attL sites in the donor plasmid containing the insert to get attB sequences again. The LR reaction is the same as the BP reaction but requires LR clonase. Again equal moles of pDONR-insert and pHG8 were recombined overnight to get pHG8-insert. This plasmid was then used to transform *E. coli*, amplified under selection, isolated and confirmed.

Competent *E. coli*

To make competent *E. coli*, 5 mL of LB was inoculated with 5 μL, of DH5α cells and incubated overnight at 37° C. with moderate shaking (200 rpm). This starter culture was then used to inoculate 200 mL of LB which was incubated at 37° C. with moderate shaking for 3-4 hours, until the culture had an OD600 of 0.6. The culture was then incubated on ice for 30 minutes before being pelleted at ~3,000 g at 4° C. for 20 minutes. The pellets were resuspended in 200 mL ice-cold water before being pelleted again in the same conditions. This cycle was repeated two more times with the last resuspension being in 20 mL ice cold 10% glycerol. The cells were pelleted again at 4° C., but at ~2,000 g for 10 minutes, and resuspended in 1 mL ice cold 10% glycerol. This resuspension was then distributed into 50 μL aliquots which were snap frozen in liquid nitrogen and stored at −80° C.

*E. coli* Transformation

For difficult transformations, commercial competent cells, One Shot OmniMAX™—T1R Chemically Competent Eco (Invitrogen) were used. 100 μl of the cells were thawed on ice and ~100 ng of ligation mix was added. Cells were then left on ice for 30 minutes before being heat shocked at 42° C. for 30 seconds. Cells were then put back on ice for 2 minutes before adding 250 μl of the SOC medium supplied. The cells were then allowed to recover at 37° C. with shaking for 1-2 hours.

For most transformations, homemade competent cells were used. An aliquot of 100 μL competent cells was defrosted on ice and ~100 ng of plasmid DNA was added and mixed with the pipette tip. The cells were then snap frozen in liquid nitrogen before being incubated in a 37° C. water bath for five minutes. Then 1 mL of LB was added to the cells and they were incubated at 37° C. with shaking for 1-2 hours. Two different volumes of cells were then plated onto appropriate selective media and incubated at 37° C. overnight.

Bacterial Growth and Glycerol Stocks

All bacterial liquid cultures were grown in Luria-Bertani (LB) media, made up of the following: 10 g/L tryptone-bacto (BactoLaboratories, Australia), 5 g/L yeast extract (Bacto-Laboratories) and 5 g/L NaCl in MilliQ treated water. If LB agar was needed, 15 g/L agar (Lener Davis Gelatin, Australia) was added to broth. All media was sterilised by autoclaving before use. Antibiotics were used at the following concentrations: 100 μg/mL spectinomycin (Sigma), 100 μg/mL ampicillin (Sigma) and 150 μg/mL rifampicin (Sigma), 30-504 ml kanamycin (MP Biomedical, Solon, Ohio, USA), 50 g/mL zeomycin (Invitrogen, Carlsbad, Calif., USA). For zeomycin selection, low salt LB was used: 10 g/L tryptone-bacto (BactoLaboratories, Australia), 5 g/L yeast extract (BactoLaboratories) and 5 g/L NaCl in MilliQ treated water. For blue-white selection, plates also contained 0.5 mM IPTG (isopropyl-b-D-thiogalactoside; Fisher Biotech) and 80 μg/mL X-gal (5-bromo-4-chloro-3-indolyl-beta-D-galactopyranoside; Progen Bioscience, QLD, Australia).

Liquid cultures of *E. coli* were incubated overnight at 37° C. with shaking, plates of *E. coli* were incubated at 37° C. overnight, plates of *Agrobacterium* were incubate at 28° C. for several days and liquid cultures of *Agrobacterium* were incubated with shaking at 28° C. for 16-20 hours.

Glycerol stocks of bacterial cultures were made by combining 700 μL of culture with 700 μL glycerol solution (65% glycerol v/v, 0.1M MgSO4, 0.025M Tris-Cl, pH8). Stocks were then stored at −80° C.

Colony PCR

Colony PCR was undertaken to screen colonies for the presence of the plasmid and the insert. PCR conditions were as normal but volumes were made up to 20 μl per reaction and a small amount of cell transferred from the colony to the PCR using a pipette tip.

Plasmid Isolation

For most applications plasmids were isolated from 3-5 mL of liquid culture, grown overnight from a single colony or glycerol stock, using the GeneElute™ Plasmid Miniprep Kit (Sigma). In brief, cells were pelleted and lysed using a modified alkaline-SDS lysis method. The plasmid DNA was then adsorbed onto a silica membrane in the presence of high salts. The membrane was then washed before the plasmid DNA was eluted with sterile $dH_2O$.

For applications where a large amount of plasmid was required, such as preparation of BAC DNA, a large scale alkaline lysis protocol was used. This protocol was based on one obtained from the Lab of Cellular and Molecular Regulation, NIH (Bethesda, Mass., USA). A 500 mL culture with selection was grown overnight at 37° C. and 200 rpm. 250 mL of cells were then pelleted at 6000 g for 15 minutes at 4° C., the supernatant discarded and the bottle was placed on ice. Cells were then resuspended in 2 mL room temperature 10 mM EDTA, pH 8.0, and left at room temperature for 5 minutes. 40 mL of lysis solution (0.2M NaOH, 1% SDS) was then added and the bottle left at room temperature for 5 minutes. 30 mL of ice-cold neutralization solution (11.5% (v/v) acetic acid, 1.9M K-acetate) was then added and the bottle left on ice for 15 minutes. Cell debris was then pelleted at 30,000 g for 20 minutes at 4° C. The supernatant was moved to a new bottle and the process repeated. DNA was then precipitated out of the supernatant by adding 45 mL of isopropanol and pelleted at 6,500 g for 15 minutes. The pellet was then dissolved in 9 mL of 10 mM tris/50 mM EDTA and 4.5 mL of 7.5M K-acetate was added. The solution was then frozen at −70° C. for 30 minutes, thawed and centrifuged at 4,000 g for 10 minutes. The DNA was then precipitated by adding 27 mL of 100% ethanol and the DNA was pelleted at 4,000 g for 10 minutes. The pellet was then dissolved in 700 µL of 50 mM Tris/50 mM EDTA, pH 8.0 and 10 µL, of 10 ng/µL RNAse was added. The sample was then incubated at 37° C. for 1 hour to allow the breakdown of RNA. The sample was then cleaned by adding 700 µl of phenol:chloroform:isoamyl alcohol (25:24:1), mixing and centrifugation at 14,000 rpm for 5 minutes in a microcentrifuge. The top layer was then cleaned again in 700 µl chloroform:isoamyl alcohol. The DNA was then precipitated from the top layer by the addition of 700 µl isopropanol and pelleted by centrifugation at 14,000 rpm for 20 minutes. The supernatant was the removed and the pellet washed with 500 µl of 70% ethanol and spun for 10 minutes at 14,000 rpm. The supernatant was again removed and the pellet air dried before being resuspended in 100 µl sterile $H_2O$.

Diagnostic Digests

To confirm the identity of a plasmid and the presence of the insert, isolated plasmid was digested overnight and run on a 1% agarose gel. The expected pattern of bands was identified using NEBCutter V2.0 (New England Biolabs; Vinzce et al, 2003).

Competent *Agrobacterium*

Competent *Agrobacterium tumefaciens* were made from a 500 mL culture, grown is overnight at 28° C. 250 mL of culture was then chilled on ice and pelleted for 5 minutes at 4° C. at 3,000 g. Pellets were resuspended in 1 mL ice-cold 20 mM $CaCl_2$ and dispensed in 0.1 mL aliquots before being frozen in liquid nitrogen and stored at −80° C.

*Agrobacterium* Transformation

Homemade competent *Agrobacterium tumefaciens* cells were transformed with the isolated plasmid. 100 µl of competent cells were thawed on ice and ~1 µg of plasmid was added. The cells were then heat shocked at 37° C. for 5 minutes before adding 1 mL of liquid LB. Cells were allowed to recover at 28° C. with shaking for 2-4 hours. A negative control of competent *Agrobacterium* cells without any plasmid was included. Cells were then spread on LB agar plates with kanamycin selection for the plasmid (50 µg/mL); and rifampicin (100 µg/mL) and gentamycin (25 µg/mL) selection for *Agrobacterium*. Plates were then incubated at 28° C. for 2-3 days or until colonies appeared. Colonies were screened for the insert by colony PCR using insert specific primers. These colonies were also used to inoculate a 5 mL starter culture of liquid LB with selection (50 µg/mL kanamycin, 100 µg/mL rifampicin, 25 µg/mL gentamycin). Cultures were grown at 28° C. overnight with shaking.

*Arabidopsis* Transformation

*Arabidopsis* to be transformed was grown on soil and the first flowering bolts cut back to encourage multiple secondary bolts. Plants were dipped when there are many flower clusters and any developed siliques are cut off. *Arabidopsis* was then transformed using a modified protocol from Clough and Bent (1998). A 5 mL starter culture with selection was used to inoculate 500 mL liquid LB. This was then grown overnight at 28° C. with shaking.

The 500 mL culture was pelleted in a RC 5C Plus centrifuge (Sorvall) using an SLA-3000 rotor at 4,000 rpm for 20 minutes at room temperature. The pellet was then resuspended in 500 mL of 5% (w/v) sucrose solution. The detergent Silwet® L-77 (Lehle Seeds, Round Rock, Tex., USA) was then added to a final concentration of 0.05% (v/v). Flowers were dipped in the solution for 5-10 seconds with gentle agitation before being laid flat in a tray under cling wrap to maintain humidity. Plants were stood up the next day and the process repeated a week later. After allowing seed set for two weeks plants were transferred to a dark, dry cupboard for drying of the seeds.

Seeds were plated on selection to isolate transformants, which were then transferred to soil.

Sequencing

DNA fragments or plasmids were sent with the appropriate primers to the Biomolecular Resource Facility (JCSMR, ANU, Canberra) or the Australian Genomic Resource Facility (UQ, Queensland) to be sequenced.

Alternatively, DNA was prepared in a 20 µL sequencing reaction made up of the following: 0.5 µM primer, 1× buffer, 2 µL DNA and 1.5 µL Big Dye®. The reaction proceeded as follows: 96° C. for 2 minutes and 40 cycles of: 96° C. for 5 seconds, 50° C. for 15 seconds, 60° C. for 3½ minutes. PCR product was then purified using an EDTA purification. To the 20 µL, 5 µL of 0.125M EDTA and 60 of room temperature 100% ethanol was added. The sample was mixed and left to precipitate at room temperature for 40 minutes under foil. The labelled DNA was then pelleted at maximum speed for 20 minutes and washed with 70% ethanol before being centrifuged again for 5 minutes. The supernatant was removed and the pellet dried using a Speedi-Vac®. The sample was then given to Yang for sequencing.

Thermal Asymmetric Interlaced (Tail)-PCR

Protocol was adapted from (Liu Y-G, Mitsukawa N, Oosumi T, and Whittler, R F (1995) "Efficient isolation and mapping of *Arabidopsis thaliana* T-DNA insert junctions by thermal asymmetric interlaced PCR", *The Plant Journal* 8: 457-463). As described in Liu et al. 1995, a sequential use of three primers (LBa1—5'-TGGTTCACGTAGTGGGC-CATCG-3' (SEQ ID NO: 23); LBb1—5'-GCGTGGAC-CGCTTGCTGCAACT-3' (SEQ ID NO: 24); and LBc1—5'-GGACTCTTGTTCCAAACTGG-3' (SEQ ID NO:25)) specific to the left border of the T-DNA insert with an arbitrary degenerate primer, AD2 (5'-NGTCGA(G/C)(A/T)GANA(A/T)GAA-3' (SEQ ID NO: 63), with 128-fold degeneracy, that would bind to *Arabidopsis* sequences in a series of three PCR reactions was performed. The primary reaction was 20 µL and contained 1×PCR buffer, 200 µM each dNTP, 2 mM $MgCl_2$, 0.2 µM LBa1, 3 µM AD2, 0.8 U F1 Taq and about 20 ng genomic DNA. Two reactions were performed for each sample, one was diluted 50-fold for the next PCR and the other kept to run on the final gel.

The secondary reaction was 20 µL. It contained 1×PCR buffer, 200 µM each dNTP, 2 mM $MgCl_2$, 0.2 µM LBc1, 2 µM AD2, 0.6 U F1 Taq and 1 µL of diluted PCR product from the primary reaction. Two reactions were performed for each sample, one was diluted 10-fold for the next PCR and the other kept to run on the final gel. The tertiary reaction was 100 µL and using the same conditions as the secondary reaction, except the third LB-specific primers together with AD2 was used.

All amplified products were analysed by agarose gel electrophoresis. Insertion-specific products were identified by the size difference between bands in the secondary and tertiary reactions. Appropriate bands were gel-excised using a QIAquick® Gel Extraction Kit (Qiagen) and sequenced (AGRF, Brisbane, Australia).

SAL1 Protein Analysis

To produce recombinant SAL1 protein, total RNA was extracted from Col-0 and alx8 leaves using Plant RNeasy® Kit with the on-column DNAse digestion step (Qiagen) and was used for first-strand cDNA synthesis (SuperScript® II, Invitrogen) as per manufacturers instructions. The complete SAL1 coding sequence was amplified from the cloned Col-0 and alx8 SAL1 cDNAs with the primers SacII-SAL1 F1 (5% ctccgcggtggtatggcttacgagaaagagc-3') (SEQ ID NO: 26) and EcoRI-SAL1 (5'-gctcgaattctcagagagagaagctttctc-3') (SEQ ID NO: 27), then cloned into the pHUE vector (Baker et al., 2005). Recombinant proteins were expressed in *E. coli* strain BL21(DE3) (Novagen) after induction with 1 mM IPTG and purified by affinity chromatography using His-Bind resin according to the manufacturer's instructions (Novagen). Authentic SAL1 protein without the tag was recovered by enzymatic cleavage and assayed for phosphatase activity against 3'-Phosphoadenosine 5'-phosphate (PAP) (Murguia et al., 1995), *Science* 267, 232-234) and anti-SAL1 polyclonal antibodies (IMVS, Adelaide) were isolated from the IgG fraction of inoculated rabbit serum by immunoaffinity purification.

For western blots, 20 µg of the leaf protein extract was resolved on a gradient gel, electrotransferred to a nitrocellulose membrane, and probed with 1:1,000 dilution of purified polyclonal antibodies against the recombinant SAL1 protein. After washes with 0.05% (v/v) Tween® PBS, blots were incubated with 1:10,000 dilution of HRP-conjugated goat anti-rabbit IgG and developed using the Super Signal West Femto Chemilumiscent detection kit (Pierce).

Gene Expression Analysis

Precautions Taken when Handling RNA

Due to the abundance of RNAse enzymes in the environment a number of precautions were taken to prevent RNA degradation from occurring. Gloves were always worn when handling RNA and care was taken to work in a clean environment where possible. Samples were kept on ice, stored at $-80°$ C. and the number of freeze-thaw cycles limited. RNAse-free water was either obtained commercially or made by treatment of MilliQ H2O with 0.2% (v/v) diethylpyrocarbonate (DEPC, Sigma). DEPC-treated water was stirred overnight before being autoclaved to destroy any remaining DEPC before use. Glassware was baked at 180° C. overnight and plasticware was soaked in dilute $H_2O_2$ overnight before being rinsed with DEPC-treated water several times.

RNA Extraction

RNA was extracted using the Plant RNeasy® Kit (Qiagen, Germany). In brief, no more than 100 mg of frozen tissue was ground into powder using sterile micropestles. The sample was lysed and denatured in the guanidine isothiocyanate (GITC)-containing buffer supplied, which also inactivates any RNAses. The sample was then applied to a QIAshredder®, which removes insoluble material and shears genomic DNA. The elute was mixed with 100% ethanol to precipitate the RNA and the mixture was put through a RNeasy® Mini-column, where the RNA binds a silica-gel membrane. The membrane was washed and treated with RNAse-free DNAse I (Qiagen) for approximately 20 minutes and washed again before the RNA was eluted in RNAse-free $H_2O$.

RNA Precipitation

To concentrate and clean RNA a protocol from the Current protocols in Molecular Biology (Ausubel et al, 1998) was used. In brief, 1/10 volume of Na acetate, pH 5.2 was added to the RNA. The sample was vortexed briefly to mix before adding 2.5 volumes of ice-cold 100% ethanol. Again the sample was mixed by vortex and placed at $-20°$ C. for 30 minutes to facilitate RNA precipitation. The RNA was then pelleted at maximum speed in a benchtop centrifuge for 5 minutes. The supernatant was removed and the pellet washed with 70% ethanol before being centrifuged again. The supernatant was removed and the RNA dried in a Speedi-Vac® for 5 minutes at medium heat before being dissolved in RNAse-free $H_2O$.

cDNA Synthesis cDNA synthesis was carried out according to a protocol acquired from Christian Delessert (Plant Industry, CSIRO, Canberra, Australia). 1 µg of T23V primer was added to 1 µg of RNA and incubated at 70° C. for 10 minutes to allow primer binding. Then the reaction was made up to 30 µL containing: 1× the appropriate buffer, 10 mM dithiothreitol, 0.17 mM RNAse-free dNTPs (Invitrogen), 100 units of SuperScript® II (Invitrogen) and RNAse-free $H_2O$ to 30 µL. The reaction was then incubated at 45° C. for 2 hours and diluted to 200 µL in sterile milliQ $H_2O$. The cDNA was then ready for real time RT-PCR analysis.

Real Time RT-PCR

Real time reverse transcription Polymerase Chain Reaction (real time RT-PCR) was used to measure transcript abundance.

Primer Design

Appropriate primers for real time RT-PCR were designed using the Primer3 program (www-genome.wi.mit.edu/cgi-bin/primer/primer3_www.cgi) with the following conditions:
product size approximately 250 bp
melting temperature ($T_m$) approx. 60° C.
GC content approximately 50%
maximum self-complementarity of 4
maximum 3' self-complementarity of 3

Gene sequences used were the spliced cDNA sequence, obtained from TAIR. If possible the primers were designed either side of an intron to allow DNA contamination to be detected. The specificity of the primers was checked by a 'Blastn' search on the National Center of Biotechnology Information website (NCBI, http://www.ncbi.nlm.nih.gov/). All primers were ordered from Proligo (Australia). Examples of some of the primers used are given in (Rossel, J. B., P. B. Walter, et al. (2006), *Plant, Cell and Environment* 29(2): 269-281). Examples of other primers used include:

```
APX2 (At3g09640),
5'-GGCTGGGACATTTGATGTG-3'          (SEQ ID NO: 28)
and

5'-AGGGAACAGCTCCTTGATAGG-3';       (SEQ ID NO: 29)

APX1 (At1g07890),
5'-CCACTCGCATTTCTCCAGAT-3'         (SEQ ID NO: 30)
and

5'-TCGAAAGTTCCAGCAGAGTG-3';        (SEQ ID NO: 31)
```

-continued

```
sHSP (At2g29500),
5'-CCTGGATTGAAGAAGGAGGAAG-3'        (SEQ ID NO: 32)
and

5'-TAGGCACCGTAACAGTCAACAC-3';       (SEQ ID NO: 33)

ZAT10 (At1g27730),
5'-AGGCTCTTACATCACCAAGATTAG-3'      (SEQ ID NO: 34)
and

5'-TACACTTGTAGCTCAACTTCTCCA-3';     (SEQ ID NO: 35)

cyclophilin (At2g29960),
5'-TCTTCCTCTTCGGAGCCATA-3'          (SEQ ID NO: 36)
and

5'-AAGCTGGGAATGATTCGATG-3';         (SEQ ID NO: 37)

DREB2A (At5g05410),
5'-AGACTATGGTTGGCCCAATG-3'          (SEQ ID NO: 38)
and

5'-TCGAGCTGAAACGGAGGTAT-3';         (SEQ ID NO: 39)

HSP70 (At3g09440),
5'-GCTGCTATTGCTTACGGTCTTG-3'        (SEQ ID NO: 40)
and

5'-CTCTCGGGTTTCCACTAATGTC-3'.       (SEQ ID NO: 41)
```

To check the accuracy and efficiency of the primers, a standard curve was performed with 100, 25, 5 and 1 ng of cDNA. Each concentration was done in duplicate. The R2—value, reaction efficiency and melt curves are automatically formulated by the Rotorgene® 5 Program. For accurate primers the R2—value must be >0.99, the reaction efficiency must be >95% and the melt curve must indicate only one product being amplified. Only if these conditions are met are the primers used for real time RT-PCR.

Real Time RT-PCR Set-Up

Real time RT-PCR reactions were performed in the Rotor-Gene® 2000 or Rotor-Gene® 3000 (Corbett Research, Australia). In some cases, triplicates of each cDNA sample were performed. Alternatively, duplicate reverse transcriptions were performed and two technical replicates of each reverse transcription resulted in four replicates per RNA sample.

Each sample was tested with both the primers for the gene of interest and those for the 'housekeeper' gene. Real time RT-PCR allows the quantification of mRNA abundance in a particular tissue following various treatments relative to a housekeeper gene, whose expression does not change. This is done by measuring the rate of amplification of the transcripts over repeated cycles by measuring the incorporation of a fluorescent dye, SYBR green, into the transcripts. This dye binds all dsDNA molecules and only emits a fluorescent signal when bound.

To perform the reaction SYBR® Green JumpStart™ Taq ReadyMix™ (SigmaAldrich) or Roche LightCycler4800 SYBR Master (Roche, Basel, Switzerland) was used as per manufacturer's instructions. For Sigma the master mix contained 10 mM Tris-HCl, pH 8.3, 50 mM KCl, 3.5 mM $MgCl_2$, 0.2 mM each dNTP, 0.25 units Taq DNA polymerase, Jump-Start Taq antibody and SYBR Green I. For Roche the contents of the master mix were undisclosed. A typical 10 µL reaction contained 25 ng cDNA, 0.2 µM each primer and 0.9× Master mix. Typical cycle conditions were as follows:

95° C. for 2 min (initial activation of Taq DNA polymerase)

Cycle repeated 45 times: 95° C. for 15 s (denaturing), 55° C. for 30 s (primer binding), 72° C. for 30 s (elongation and reading of fluorescence) and 80° C. for 15 s (reading of fluorescence)

60° C. for 2 min (final elongation step)

Melt Curve analysis by ramping to 99° C., increasing 1° C. with each 5 s step.

Analysis

Real time RT-PCR results were analysed using the Rotor-Gene® 5 program (Corbett Research). For each reaction the melt curve was checked to make sure a single product was made with each set of primers and that there was efficient amplification of the product. Analysis methods used for real time RT-PCR were as previously described (Rossel, J. B., P. B. Walter, et al. (2006), Plant, Cell and Environment 29(2): 269-281; Pfaffl, M. W. (2001), "A new mathematical model for relative quantification in real-time RT-PCR", Nucleic Acids Research 29(9)).

is For the comparative Ct method the threshold value for the amplification reaction was set at a point where all samples are undergoing an exponential rate of amplification. Threshold cycle (Ct) values are the number of cycles taken for a particular sample to reach the threshold value, where the amount of fluorescence, and hence the amount of dsRNA, is the same for each sample. These Ct values are then transferred to Excel (Microsoft, USA). Outliers, with Ct values differing more than 0.5, in each set of triplicates were deleted. The resulting data set is then normalised by comparing the expression of the gene of interest, at a certain time point and conditions, with the expression of the house keeper gene, at the same time and conditions. This is done by deducting the average Ct value of the housekeeper in that sample from each Ct value replicate of the gene of interest:

$$\Delta Ct = Ct(\text{gene of interest}) - \text{average } Ct(\text{housekeeper})$$

These values are then compared to the control sample, usually t=0. This is done by subtracting the control value from each sample value to get ΔΔCt.

$$\Delta\Delta Ct = \Delta Ct(\text{gene of interest}) - \Delta Ct(\text{Control})$$

These values are then used to calculate the absolute values using the formula: 2-ΔΔCt. As a result, the control value becomes 1 and all other samples are given a value relative to the control value.

For the comparative quantification method the program analyses samples compared to a user-defined control sample, usually t=0. It then calculates the comparative concentration using the formula:

$$\text{Comparative concentration} = \text{Amplification}^{(\text{ControlTakeOff}-\text{ThisSampleTakeOff})}$$

The take off value is calculated using the rate of fluorescence increase over cycles. The maximum rate is termed the peak rate and the take off rate is taken to be 80% below the peak rate. The take off value is the number of cycles that have occurred when the reaction reaches the take off rate.

The amplification is the average amplification efficiency for all samples for a particular primer set. This is calculated as the average of the fold increase of fluorescence during the four cycles following the take-off point. Ideally this value would be 2 during the exponential phase of the reaction. An average amplification efficiency and confidence interval is also given for each primer set with increasing confidence interval values indicating more variability between samples.

The computer derived comparative concentrations for each sample were then exported to Excel and normalised against those of the housekeeper. This results in the change in expression as a percentage or fold-change relative to the control. The standard deviation for each set of replicates was also calculated using the Excel function. Results were then plotted as a column graph using Excel. Where appropriate the results for multiple biological replicates were averaged and the standard deviation between experiments calculated using the STDEVPA function, which measures the standard deviation based on the entire population given as arguments.

Northern Blot

Northern Blots were used to investigate to what extent genes were expressed and whether splice variants occurred.

RNA extractions were performed as above using the RNeasy® Kit only three QIAShredder® columns were used per biological replicate and the elute put through the one RNeasy® Column to maximise the concentration of the resulting elutant. 20 µg of RNA for each sample was then precipitated as above and resuspended in 5 µL of RNAse-free water.

Gel electrophoresis was performed with the concentrated RNA in RNAse-free conditions. A gel was made by melting 2.25 g agarose in 125 mL DEPC-treated H2O. The mixture was cooled before adding 15 mL 10×MOPS (0.4M MOPS, 0.1M sodium acetate, 0.01M EDTA), 7.5 mL formaldehyde and 2 µL of Ethidium Bromide (EtBr). The gel was set in a normal gel electrophoresis tank before being equilibrated in 1×MOPS with 1 µL/100 mL EtBr added.

To each 20 µg of RNA, 9 µL of formaldehyde, 25 µL of formamide and 4.2 µL of 10×MOPS were added. The samples were then vortexed to mix and heated at 55° C. to denature the RNA. 0.5 µL of EtBr and 2 µL of loading buffer (1 mM EDTA pH 8.0, 50% glycerol, 2.5 mg/mL bromophenol blue, 2.5 mg/mL xylene cyanol) were added to each sample before loading then on the gel. The gel was run at 100V for several hours until the dye had moved ⅔rds of the way down the gel. The RNA was then quickly photographed under UV illumination to check the quality and quantity of the RNA.

The RNA was transferred to a nylon membrane (Hybond®-N, Amersham Biosciences, Buckinghamshire, UK) by gravity blotting with 20×SCC overnight. The nylon membrane was then wrapped in cling wrap and the RNA was fixed to the membrane by UV illumination at 1200V. The membrane was then stored in the dark until use.

A probe was made by amplifying SAL1 from Col-0 WT cDNA using the primers Fry1-1F (5'-AACCCATTTTG-TAAATCTTCC-3') (SEQ ID NO: 42) and Fry1-rt2R (5'-CAGAGAAACAAAGAACGTACGAGA-3') (SEQ ID NO:43) and a 40 µL reaction. The PCR product was run on a gel and purified using a gel extraction kit. The probe was then labeled with radioactive α32P-dCTP using the Prime-a-gene® Labeling System (Promega) as per manufacturer's instructions. The procedure was undertaken as described in (Rossel J. B., Wilson I. W., and Pogson B. J. (2002), "Global changes in gene expression in response to high light in *Arabidopsis*", Plant Physiol. 130: 1109-1120).

Microarrays

RNA for microarrays was extracted as above using the RNeasy® Kit. The concentration and purity of the RNA was then measured using a Nanodrop® Spectrophotometer. The quality of the RNA was also checked by gel electrophoresis of 3 µg of RNA. In brief, a 1% gel was made by melting high quality Agarose-1000 in 1×MOPS buffer. The mixtures was cooled to 55° C. before adding warm formaldehyde to a final concentration of 18% (v/v) and pouring into the gel cast. Once set the gel was equilibrated with 1×MOPS running buffer. The RNA, in 10 µL, was combined with 20 µL of loading buffer (52% formamide, 1×MOPS, 17% formaldehyde, 7% glycerol, 0.02 mg/mL EtBr, touch of bromophenol blue), heated for 5 min at 70° C. and then cooled on ice for 2 minutes. Samples were then run in the gel for several hours at 90V, till the dye had travelled ⅔ of the gel length.

If the RNA needed to be more concentrated the volume was decreased in a Speedi-Vac® at medium heat for a short period of time. The quality and quantity of RNA was also tested on a RNA 6000 Nano LabChip® using the Agilent 2100 Bioanalyser system (Santa Clara, Calif., USA) according to manufacturer's instructions. This system separates RNA molecules based on their size through electrophoresis of a gel matrix in capillary tubes. Each sample and a ladder are heat denatured before being run in different tubes. An intercalating dye in the gel matrix labels the RNA and the quantity and weight is read as it comes through the capillary.

Once the quality of the RNA was confirmed the RNA was prepared for use in the Affymetrix GeneChip® Expression Analysis System (Santa Clara, Calif., USA) using the manufacturers kits and instructions. In brief, 5 µg of RNA was reverse transcribed using a T7-Oligo(dT) primer and Superscript II, called the first strand synthesis. This results in the RNA being bound to a complementary DNA strand. A second strand of cDNA was then synthesised to replace the RNA in the second strand synthesis. This synthesis uses RNAse H to remove the RNA before rebuilding the second strand as DNA using T4 DNA polymerase. The reaction components are then removed from the cDNA by use of a cDNA binding column which was washed, dried and the cDNA eluted.

Biotin labeled cRNA was then amplified from the cDNA using an in vitro transcription (IVT) process. This process uses biotinylated nucleotide analog/ribonucleotide mix and T7 RNA polymerase. The cRNA was then purified using a column that binds cRNA and a small aliquot was run through the Bioanalyser to confirm the quality and quantity of the product.

The biotin labelled cRNA was also quantified by nanodrop spectrophotometry and the purity confirmed. The yield was adjusted for unlabelled RNA present due to total RNA being used in the original sample. This was done using the formula:

$$\text{Adjusted cRNA yield} = RNAm - \text{total } RNAi$$

where RNAm is the amount of cRNA measured after the IVT reaction and clean-up (µg) and total RNAi is the original starting amount of RNA (µg).

20 µg of the cRNA was then fragmented into 35-200 bp fragments by $Mg^{2+}$ metal-induced hydrolysis. A small aliquot was run in the Bioanalyser to confirm fragmentation had occurred.

To confirm the quality of the RNA, a small amount of fragmented cRNA from one sample was then hybridised to a TestArray3. The process was the same as for the ATH1 chips.

For the ATH1 GeneChip®, 15 µg of each sample of fragmented cRNA was hybridised overnight (16 hrs) at 45° C. with rotation. The GeneChip® were then washed in a non-stringent wash using a Fluidics Station 400. The GeneChip® were then stained with streptavidin phycoerythrin (SAPE), which binds to the biotin labelled cRNA. The signal was then amplified by the addition of a primary antibody that binds the SAPE. A Biotinylated secondary antibody that binds the primary antibody was then added and finally SAPE that binds the secondary antibody. The GeneChip® was then washed to get rid of excess SAPE before being scanned. Phycoerythrin fluoresces at 570 nm, so the GeneChip® was scanned at this wavelength. The results were then analysed.

A number of controls are added throughout the above steps. Four polyA RNA control were added during the first strand synthesis to ensure the production of labelled-cRNA if effective. These controls are from four genes of *B. subtilis* that are not present in eukaryotic cells. They are also added at varying concentrations to ensure that the process is effective for low, medium and high abundance transcripts. In the final analysis of the array the intensity readings of these genes should have a linear relationship to their original concentrations.

A set of hybridisation controls were added to the fragmented cRNA before hybridisation. These again have a range of concentration to ensure the relationship between hybridisation and signal intensity is linear. Three of the controls are from *E. coli* and one is from the P1 bacteriophage.

Finally, biotinylated B2 oligonucleotides were also added to the hybridisation mixture. These bind in a checkerboard fashion around the outside of the array, to allow automatic alignment of the grid to identify the probe sets.

Analysis, including MASS normalisation, statistical analysis and false discovery correction rate, was carried out as previously described (Rossel et al (2007), *The Plant Cell*, 19: 4091-4110).

Morphological and Physiological Measurements
Leaf Measurements

Total water potential was measured using a custom built thermocouple psychrometer (Morgan, (1991), *Australian Journal of Plant Physiology*, 18, 249-257). Leaf discs were placed into the equilibration chambers for 4 h at 22° C. A Peltier cooling current was passed through the thermocouple and the electromotive force (emf) read as a needle deflection in a microvoltmeter (HR 33 Dew Point, Wescor). The leaf water potential (MPa) was calculated by interpolation of the emf to a standard curve. Soil water potential was measured using a pressure plate apparatus (Klute (1986), *Methods of Soil Analysis, Part 1. Physical and Mineralogical Methods—Agronomy Monograph no. 9* (Klute, A., ed. Madison, Wis., USA: American Society of Agronomy—Soil Science Society of America, pp. 635-662).

A number of physiological measurements of leaf samples were also made. The thickness and surface area of leaves were recorded. In early experiments, the relative water content of leaf samples was measured by recording their fresh weight, drying them in a paper bag for 3 days at 60° C. and then recording their dried weight. Their relative water content (RWC) was then calculated using the following formula:

$$RWC\ (\%) = (FW-DW)/FW$$

In later experiments, rosette leaves from the same plants were excised, the fresh weight ($F_w$) recorded and incubated in water for at least 4 hours at 4° C. in the dark. The leaves were blotted and the turgid weight ($T_w$) measured. Finally, leaves were dried at 80° C. overnight and weighed to determine the dry weight ($D_w$). The relative water content (RWC) was calculated as (Jones, (2007), *Journal of Experimental Botany*, 58, 119-130):

$$RWC = \frac{F_w - T_w}{D_w - T_w}$$

Gas Exchange

Gas exchange measurements were done on plants grown in 12 hour days to promote vegetative growth and hence large leaves. The only exception being those plants in the drought timeline experiments that were grown in 16 hour days. Gas exchange was performed with a Li-6400 (Li-Cor, Lincoln, Nebr., USA) as per manufacturer's instructions. This instrument allows a leaf that is attached to the plant to be clamped into a chamber and a range of parameters measured. Within the chamber the light intensity, spectrum, temperature, humidity and $CO_2$ concentration can be controlled. By comparing the amount of $CO_2$ and water vapour going into the chamber and coming out of the chamber the amount of photosynthesis and the conductance of the stomata can be inferred. By changing conditions such as light intensity and $CO_2$ concentration we can see how the stomata respond by plotting the average conductance of the leaf. The chamber is 2 $cm^2$ so if the *Arabidopsis* leaf does not fully cover this area the conductance is adjusted for the leaf area inside the chamber.

High Performance Liquid Chromatography (HPLC)

The carotenoid profile of leaf material was analysed by HPLC. In brief, leaf material was ground in 500 μL of a 60/40 (v/v) mixture of acetone/ethyl acetate. This was diluted with 400 μL of $dH_2O$ and centrifuged at maximum speed in a benchtop centrifuge for 3 minutes. Carotenoids were fractionated and assayed using an Agilent HPLC and photodiode array detector as described (Pogson, B. J., Niyogi, K. K., Bjorkman, O., and DellaPenna, D. (1998), "Altered xanthophyll compositions adversely affect chlorophyll accumulation and nonphotochemical quenching in *Arabidopsis* mutants", *Proc. Natl. Acad. Sci. U.S.A.* 95: 13324-13329). Carotenoids were identified by comparison of their spectra and retention times to standards and the peak areas recorded for quantification using molar extinction coefficients.

Carbon-13 Measurements

The amount of $^{13}C$ in leaf tissue give an indication of the average stomatal aperture over a plants life as when the stomata are open it will discriminate in favour of $^{12}C$ over $^{13}C$. Leaf samples were weighed to get their fresh weight and dried for 3 days at 60° C. in a paper bag. The dried samples were then ground using a mortar and pestle and the powder was used for determine to ratio of $^{12}C$ to $^{13}C$ in the sample.

Chlorophyll Content

Total chlorophyll content was measured by absorbance at 647 nm for chlorophyll a and 663 nm for chlorophyll b. To extract the chlorophyll 10-20 μg of leaf tissue was ground with a ball bearing and 700 μL of extraction buffer (80% acetone, 2.5 mM sodium phosphate buffer pH 7.8) in the Tissue-Lyser. Samples were then centrifuged at maximum speed in a benchtop centrifuge for 5 minutes. The absorption of the extract was then measured at 647 nm, 663 nm and 750 nm. The absorbance at 750 nm is background absorbance and hence was subtracted from the absorbance at 647 nm and 663 nm. To calculate the total chlorophyll content the following equation was used:

$$\text{Total chlorophyll } (\mu g/mg\ FW) = 17.76(A647 - A750) + 7.34(A663 - A750)$$

Anthocyanin Content

Total anthocyanin content was measured by absorbance at 530 nm. Approximately 30 mg of tissue was ground in 300 μL of acidified methanol (1% HCl) in the Tissue-Lyser using a ball bearing. To extract the anthocyanins, 250 μL of chloroform and 200 μL of MilliQ $H_2O$ was added and vortexed. The mixture was then centrifuged at maximum speed in a benchtop centrifuge for 5 minutes. 200 μL of the aqueous phase was then removed and the absorbance measured at 530 nm and 657 nm. Absorption was measured using either 96-well plates in a plate reader or in individual cuvettes. The absorbance due to anthocyanins was then calculated by subtracting the absorbance due to haze in the sample (at 657 nm) from the absorbance at 530 nm. The concentration of anthocyanins was measured by the equation:

$$C = A/\epsilon L \times \text{vol}/1000 \times MW \times 1/\text{weight} \times D \times 10^6$$

where C is concentration (μg/g); A is absorbance; $\epsilon$ is 26 9000, the constant for the most abundant anthocyanin, cyaniding-3-glucoside; L is the path length of the cuvette; vol is the total volume of extract (mL); MW is 449, the molecular weight of cyaniding-3-glucoside; weight is the original sample weight (g); and D is the dilution factor (if used).

Ascorbate Assays

Frozen leaf tissue was assayed for ascorbate content and the redox status of the ascorbate pool. Tissue was ground in liquid nitrogen using a mortar and pestle before weighing out about 50 mg of powder into a frozen 1.5 mL Eppendorf® tube. Four volumes of extraction buffer (2% w/v metaphosphoric acid in milliQ $H_2O$; SigmaUltra, SigmaAldrich, St. Louis, Mont., USA) was added and the sample vortexed to mix thoroughly. Samples were then centrifuged at maximum speed (16.1×g) in a benchtop centrifuge at 4° C. for 4 minutes. 50 µL of the extract was then added to 485 µL of assay buffer (67.5 mM $KH_2PO_4$, 32.9 mM $K_2HPO_4$, 1.27 mM EDTA) and tapped to mix. The reduced ascorbate content was then measured by absorbance at 265 nm and 415 nm. The ascorbate pool was then oxidised by addition of 33.3 U of ascorbate oxidase in assay buffer (5 µL at 6.67 U/µL, Calzyme Laboratories, San Luis Obispo, Calif., USA) and the absorbance measured. Another sample was reduced with 5 µL of 0.2M dithiothreitol in assay buffer for 20 minutes and the absorbance measured. Appropriate blanks were used. The total volume of the extract was also calculated.

To determine the amount of ascorbate present the absorbance at 265 nm was normalised against background absorbance and absorbance at 415 nm. This gives an ascorbate concentration that can then be used to calculate mg/100 g FW tissue. The amount of the ascorbate pool that is reduced can be calculated as the original sample concentration minus the oxidised sample concentration. The total amount of ascorbate present can be measured as the reduced sample concentration minus the oxidised sample concentration.

Oxygen Radical Adsorption Capacity (ORAC) Assay

The ORAC assay is a measure of the antioxidant capacity of a substance and is widely used to determine the antioxidant capacity of foods. For *Arabidopsis* an extract of the plant material was tested. This extract can either be membrane bound; from the plasma membrane, chloroplast thylakoids and other endomembranes; or soluble; from the cytosol, vacuole, chloroplast stroma and so on. The assay measured the fluorescence of an oxidation sensitive fluorescent molecule, Phycoerythrin (R-PE; Sigma). A free radical generator, AAPH (Sapphire BioScience), is added to the R-PE and as a result the fluorescence slowly declines. The plant extract is then added and will either decrease the rate of decline or increase it, depending on whether it has more antioxidant capacity or oxidation capacity respectively. As a standard, an antioxidant, Trolox (Fluka), is used instead of the plant extract. Trolox is a vitamin E derivative. The antioxidant capacity of the extract can then be quantified as µmol Trolox equivalent/g fresh weight tissue by comparing the area of each curve.

To make the extract, 20-100 mg of mature but not senescing leaves were frozen in liquid nitrogen and their fresh weight determined in a pre-weighed Eppendorf® tube. The frozen tissue was then ground to a fine powder and re-suspended in 400 µL sterile milliQ $H_2O$. The water-insoluble material was pelleted in a benchtop centrifuge at maximum speed at 4° C. for 30 minutes. The supernatant was removed and diluted with PBS (phosphate buffered saline; 75 mM, pH 7.0) to a concentration of 10 mg original fresh weight/mL. For the lipid soluble extract the above pellet was washed two times in $dH_2O$ before being re-suspended in 400 µL acetone. The solid materials were then pelleted in a benchtop centrifuge at maximum speed for 10 minutes at room temperature. The supernatant was removed and diluted with PBS to a concentration of 10 mg fresh weight/mL.

For the assay itself an Eclipse spectrophotometer (Cary) was used that can mix samples in the cuvette using a small stirring rod and can measure fluorescence of four samples at once. Hence a blank, standard and two samples can be run simultaneously. These are made up as follows:

1. Blank—2738 µL 3.38 mg/L R-PE+150 µL 1×PBS+150 µL 320 mM AAPH
2. Standard—2738 µL 3.38 mg/L R-PE+150 µL 20 µM Trolox+150 µL 320 mM AAPH
3. Sample—2738 mL 3.38 mg/L R-PE PBS+150 µL Sample+ 150 µL 320 mM AAPH First, the R-PE and sample/Trolox/PBS is added to the stirred cuvette and the fluorescence stabilized at ~800, over about 20 minutes. The AAPH is then added quickly to all cuvettes and the decline of fluorescence intensity measured until it reaches zero. The area under each curve is integrated, adjusted for the dilution factor and the antioxidant capacity calculated.

ABA Measurements

ABA content in leaves was measured using the Phytodetek Eliza based assay (Agdia, Elkhart, Ind., USA). For ABA extraction, ~100 mg leaf tissue was harvested and immediately frozen in liquid nitrogen. The tissue was ground using the Qiagen TissueLyser and a ball bearing to a fine powder. The frozen powder was suspended in 1 mL extraction solution (80% HPLC-grade methanol, 100 mg/L butylated hydroxytoluene, 500 mg/L citric acid monohydrate) and then rotated for 24 hours in the dark at 4° C. Samples were then centrifuged at 1000×g for 20 minutes, before the supernatant was transferred to a new tube. The supernatant was dried down to ~50 µL in the dark using a SpeediVac® on medium heat to removed the methanol. The remaining liquid was then diluted to 1 mL with TBS buffer (3.03 g/L Tris base, 5.84 g/L sodium chloride, 0.2 g/L magnesium chloride hexahydrate, 0.2 g/L sodium azide, pH 7.5). A 1:100 dilution in TBS buffer of each sample was used for the assay. Assay was performed as per manufactures instructions. Plates were read at 405 nm in a Platereader.

A number of variations of the extraction protocol were trialed, including drying down samples completely before resuspension, filtering the extract and centrifugation of the extract. Tissue weights of 20, 100 and 200 mg and dilutions of 1:10 and 1:100 were also trialed.

Imaging

Scanning Electron Microscopy

Procedures were performed with the help of Dr Cheng Huang, ANU Electron Microscopy Unit.

Cryogenic Scanning Electron Microscopy was used to image the abaxial surface of leaves. In brief, small pieces of mature leaf were stuck to a mount with a mixture of tissue freezing medium and carbon paste, to help conductance. The samples were then frozen in liquid nitrogen under a vacuum to allow rapid freezing and prevent water crystal formation. The samples were then heated in a vacuum to −90° C. to etch, that is to get rid of water crystals on the sample surface. The sample was then returned to −160° C. before coating with gold particles. The sample was then imaged in a Cambridge S360 (SEM; 1987; Leica/Cambridge, Wetzlar, Germany).

The same process was used to look at the cross-section of the flowering bolt and mature leaves. However these samples were freeze fractured. In brief, once mounted and frozen in the vacuum, the top of the samples was knocked, such that the sample snapped and a cross-section was exposed.

Transmission Electron Microscopy

Fixing Leaf Samples

Small pieces of mature leaf were embedded in resin to allow electron microscopy of the leaf cross section. First the samples, ~3 mm×3 mm, were washed in a buffer of 0.1M cacolydehyde, 4% formaldehyde and 2.5% glutaraldehyde for 2 hours under a weak vacuum. This was then removed and the samples washed in 0.1M cacolydehyde three times for 15 minutes. The sample was then fixed with 0.1M oacic acid and 0.05M cacolydehyde buffer for 90 minutes. Samples were then washed in $H_2O$ three times for 15 minutes. Samples were then put through an ethanol gradient starting with 70% ethanol and moving through 80%, 90%, 95% and three lots of 100% ethanol. Each wash was left for at least 15 minutes. The samples were then washed in 100% acetone for 15 minutes to replace the ethanol. The samples were then exposed to increasing levels of resin (epon aldehyde) diluted with acetone. The first was ⅓ resin: ⅔ acetone, then ½ resin: ½ acetone, then ⅔ resin: ⅓ acetone. Each was for at least 30 minutes and was rotated to mix. Samples were then exposed to pure resin three times for more than 2 hours to get rid of any acetone. Sample were then loaded into sample moulds with new resin and baked overnight at 60° C.

Sectioning and Staining

Thin sections of the embedded leaf material were cut for TEM and light microscopy using an Ultracuts® Ultramicrotome (Reichert, Depew, N.Y., USA). A glass knife was made for cutting slices onto water. Sections were flattened using heat before being picked up on a specimen support grid. Samples were then left to dry overnight before staining in 6% (v/v) uranyl acetate in water for 20 minutes in the dark. Samples were rinsed in $dH_2O$ several times before staining in a lead citrate stain for 10 minutes. The stain was removed by rinsing in $dH_2O$ before being dried.

Imaging

Images were taken using a Hitachi H7100FA (125 kV TEM; 1995; Tokyo, Japan) attached to a SIS Megaview® III Widefield CCD camera (1300×1024 pixel, 12 bit; Soft Imaging Systems Corporations, Lakewood, Colo., USA).

Light Microscopy

Procedures were performed with the help of Lily Shen, ANU Electron Microscopy Unit.

Cross sections of the leaf, cut with the ultramicrotome, were dried on a glass slide and stained with toluidine blue, before being rinsed with dH2O. Images of the mounted slide lit from beneath were taken using a Zeiss Axioskop® (Carl Zeiss Inc., Oberkochen, Germany) with a SPOT CCD camera (1300×1240, 36 bit colour; (Spot Images Corporation, Chantilly, Va., USA). Images were then processed with SPOT Advanced Software.

Luciferase Imaging

Luciferase activity in transgenic plants was detected in vivo using a cooled CCD camera. Plants were sprayed liberally with 0.5 mM luciferin (Biosynth, Switzerland), in water and containing a few drops Tween® 80 (Laboratory Supply, Australia), both 15 minutes and immediately before imaging. Plants were left in the dark for several minutes until chlorophyll fluorescence had ceased before taking exposures varying from 2 to 10 seconds. These were then integrated to increase image intensity. A cooled CCD camera (Andor Technology, Japan) was used and images were processed using ImagePro® Plus 4.5.1 (Media Cybernetics, USA).

Extraction and Analysis of Metabolites/Solutes

Approximately 50 mg fresh weight of leaf tissue was extracted and analysed by GC-MS essentially as described by Roessner-Tunali et al. (2003), *Plant Physiology*, 133:84-99). Briefly, tissue was frozen in liquid $N_2$, then ground in a Retsch ball mill for 3 min at 15 oscillations/s. Tissue powder (~50 mg) was then extracted at 70° C. for 15 min with 0.5 mL 85% (v/v) MeOH/$H_2O$ containing 0.2 mg/mL ribitol as an internal standard. Insoluble material was then pelleted by centrifugation at 20,000 g for 10 min. A 100 μL aliquot of the supernatant was then dried under vacuum and the dried metabolite extract derivatised by methoximation with 20 μL of 20 mg/mL methoxyamine.HCl in anhydrous pyridine (30° C., 90 min). To convert reactive functional groups containing reactive hydrogens to their trimethylsilyl (TMS) derivatives, 30 μL of MSTFA was added to the reaction is mixture and allowed to react for 30 min at 37° C. The reaction was then allowed to equilibrate for at least 4 hours prior to GC-MS analysis. 1 μL was injected into the GC-MS and a 45 min temperature program used to separate analytes on a 30 m Varian Factor Four 5 ms GC column with 10 m integrated guard column. Quadrupole-MS data was acquired in the full-scan mode with a scan range from 40 to 600 m/z.

Data analysis was carried out by using freely available AMDIS software to automatically deconvolute and integrate peaks and match against an in-house database of authentic mass spectra and retention indices. Statistical analysis was carried out using custom PHP scripts to automatically process AMDIS batch reports and visualisation in Microsoft Excel.

Example 2

Results

After EMS mutation of *Arabidopsis thaliana* seeds, several mutants with altered APX2:LUC expression were identified, including mutant alx8 which had increased APX2:LUC expression. These plants showed increased drought tolerance—after 9 days of withholding water, the leaves of the alx8 mutant remained turgid, green and viable whereas wildtype leaves had wilted and died (see FIG. 7). ABA levels have been found to be higher in alx8, although at the same time, components in both the ABA-dependent and ABA-independent pathways are up regulated ((Rossel, J. B., P. B. Walter, et al. (2006), *Plant, Cell and Environment* 29(2): 269-281). For instance the high light response genes, ZAT10 and APX2, are both up-regulated in alx8. However, ZAT10 is considered to be in the ABA-independent pathway (Zhang, J. Z., et al (2004), "From Laboratory to Field. Using Information from *Arabidopsis* to Engineer Salt, Cold, and Drought Tolerance in Crops", *Plant Physiol.* 135(2): 615-621), while APX2 is ABA-dependent (Rossel et al, 2006). Up-regulation of stress response genes is consistent with previous fry1 mutants, although the stress response genes that are up regulated in each mutant are not identical, for instance RD29A is up regulated in fry1-1 (Xiong, L. M. et al. (2001), "FIERY1 encoding an inositol polyphosphate 1-phosphatase is a negative regulator of abscisic acid and stress signaling in *Arabidopsis*" *Genes & Development* 15(15): 1971-1984) but not in alx8 (Rossel et al, 2006). Similarly, the increased stress tolerance observed in alx8 is a novel trait. alx8 also has an unusual cabbage-like leaf morphology. Studies of F1 and F2 plants showed that the increased APX2:LUC expression and upregulation of other stress genes, drought tolerance and altered leaf shape cosegregated. This is consistent with a lesion in an early step of drought- or high-light stress signalling networks which is associated with a single genetic locus.

Alx8 is a Point Mutation in SAL1

The location of the alx8 point mutation was identified by positional cloning and sequencing. A mapping population was created by crossing alx8, in the Col-0 background, with wildtype Landsberg erecta. The F1 was wildtype in leaf phenotype, development and APX2 expression (data not shown), confirming a recessive mutation. The F1 individuals were allowed to self-fertilise and the segregating F2 generation was sown on soil. Individuals from the F2 generation homozygous for the alx8 mutation were identified by leaf morphology, which has been shown to segregate with drought tolerance and increased APX2 expression (Rossel et al, 2006). First pass mapping with 22 primers distributed across the *Arabidopsis* genome was performed with 400 mutant F2 individuals. This indicated that the mutation was linked to the lower half of chromosome 5. Further linkage analysis with more markers in this region gave a region of interest of 617 kb. Fine mapping of approximately 4000 F2 individuals was undertaken with two markers flanking the 617 kb region, MUB3 and MMI9.

Figure 2:
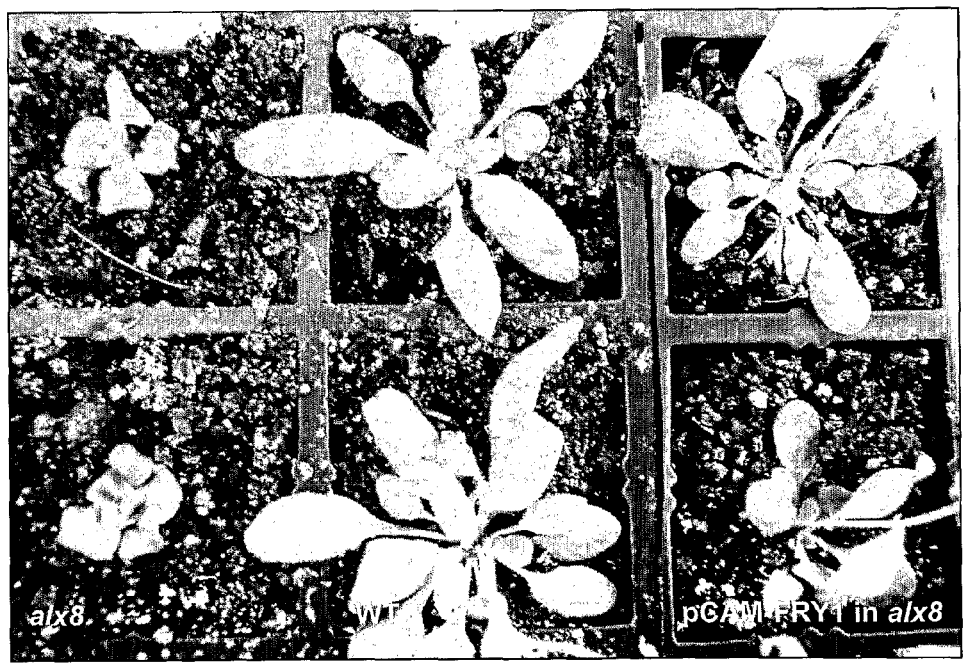
FIG. 2—Confirmation of Point Mutation in the SAL1 Gene in Alx8

To confirm the location of the alx8 mutation a wildtype copy of the SAL1 gene and promoter was used to complement the mutant phenotype. Both of the two confirmed individual alx8 transformants had wildtype leaf morphology and development. The progeny of the complemented alx8 segregated for the alx8 mutant phenotype and showed the normal wild-type leaf morphology (see FIG. 2). This confirmed that the mutation in SAL1 was indeed responsible for the mutant phenotype. Wildtype plants were also transformed with this construct but showed no change in leaf morphology, APX2 expression or development.

Figure 1B:
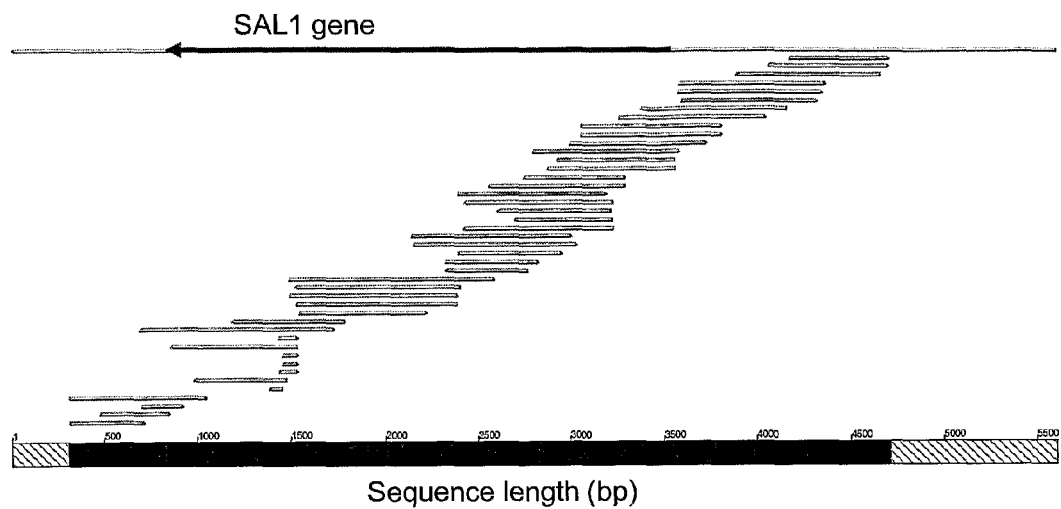
FIG. 1—Identification of Point Mutation in the SAL1 Gene in Alx8
A. Chromatograph profiles showing the sequence of the region of a point mutation in Col-0 wild type and multiple alx8 individuals from backcrossed generations and Col-0 wild type containing an APX2-LUC construct. Bottom line indicates consensus sequence as calculated by Contig Express® (Invitrogen, Carslbad, Calif., USA). Second bottom line is the sequence of the SAL1 gene from The *Arabidopsis* Information Resource (TAIR). Solid boxes indicate the site of the point mutation and dashed outline boxes an introduced mutation for dCAPS primers. All sequences except APX2-LUC are in reverse orientation ie. 3' to 5' and as sequences complimentary to SEQ ID NO:1 (thus, the point mutation is shown as C>T instead of G>A). The sequences shown in the "Col-0 wild type", "alx8—original line (M6 pool)" and "alx8—1$^{rst}$ backcross" chromatograph profiles show sequencing for nucleotides 1201 to 1248 of SEQ ID NO:1. The sequences shown in the "alx8—3$^{rd}$ backcross with dCAPS (a->g)", "alx8—4$^{th}$ backcross with dCAPS (a->g)" and "Col-0 WT with APX2-LUC" chromatograph profiles show sequencing for nucleotides 1207 to 1254 of SEQ ID NO:1.
B. Alignment of all sequences of alx8 individuals and the SAL1 gene+3 kb promoter from TAIR. Arrow shows orientation of gene sequence 5' to 3'.

Sequencing of the alx8 gene and 2 kb of promoter revealed a single nucleotide polymorphism of a guanine to adenine at the $1226^{th}$ base pair of the At5g63980.1 genomic sequence (TAIR Sequence: 4010730406 (Apr. 17, 2007), Accession#: NM_125794.4; SEQ ID NO:1; FIG. 3). This results in an amino acid change of glycine to aspartic acid at the $217^{th}$ amino acid of the coding sequence (TAIR accession: 4010745380 (Aug. 16, 2007); SEQ ID NO:2; FIG. 4). This mutation was confirmed to be the only mutation in SAL1 by further sequencing of the promoter and genomic sequence of multiple mutant plants. Four backcrossed generations were also screened for the mutation, by used of derived cleaved polymorphic sequences (dCAPS, Neff et al (1998)) markers, to confirm that the leaf phenotype was inherited with the mutation (see FIG. 1A). That is, that no other mutation in the plant was causing the mutant phenotype.

A number of mutants in SAL1 have previously been identified, including the temperature sensitive mutation, high expression of osmotic stress regulated gene expression 2 (host; Xiong et al, 2004) and the firey 1 mutants (fly1: Xiong et al, 2001). The fry1-1 mutation results in a change of the $341^{st}$ amino acid from tryptophan to a stop codon, resulting in a truncated protein missing an α5 helix which is required for enzyme activity (Xiong et al, 2001). Using in silico protein modelling against the known structure of the yeast homology, HAL2, the alx8 mutation was localized to a conserved β-sheet internal to the protein. This domain has no known function.

Salk_020882 Mutants

In the course of genotyping the alx8 mutant, further genotyping and phenotyping of recombinants allowed the area of interest to be narrowed to the BAC clone MBM17 and seven genes. A number of T-DNA insertion lines were ordered for these genes, in the hope of phenocopying the alx8 phenotype. One line, SALK_020882, phenocopied the alx8 phenotype with altered leaf morphology and delayed development (see FIG. 10). This line contains an insertion in the At5g63980 gene, known as SAL1 (FRY1/HOS2). To confirm allelism a cross was performed between alx8 and SALK_020882. All progeny had the same altered leaf morphology and delayed development of the two parents indicating that the two mutants are allelic. SALK_020882 plants (two particular lines were studied here, referred to as salk1 and salk2) were also found to be more drought tolerant than Col-0 wildtype plants (FIGS. 12 and 15). These mutants comprise a T-DNA insertion line in the Col-0 ecotype obtained from the *Arabidopsis* Biological Resource Centre (ABRC). Homozygous plants have altered cabbage-like leaf morphology, like alx8 (see FIG. 10), and are kanamycin resistant. The mutation is allelic to alx8 and these mutants show drought tolerance (see FIGS. 11, 12 and 15). Northern blots indicate that SAL1 mRNA is still present in the SALK_020882 line but multiple splice variants are present, in comparison to the Col-0 wild-type and the alx8 mutant that have only one.

The insertion site given by The *Arabidopsis* Information Resource (TAIR) is given in FIG. 9A. This was established by single pass sequencing from the LB of the T-DNA insert. This gave the complementary sequence, ie. towards the 5' end of the gene.

To confirm the location of the insertion Tail PCR was performed from the LB of the insert on DNA from one plant. This resulted in the insertion site shown in FIG. 9B. The sequence was obtained from both sides indicating the possibility of a double insert. The sequence obtained also indicated the deletion of 11 bp around the insertion site (see FIG. 9B compared to FIG. 9A).

The SAL1 Protein is Absent in Alx8 and Fry1-1

The recombinant protein for wild-type SAL1 and mutated ALX8 were produced as fusions to poly-histidine tagged ubiquitin. Both fusion proteins were successfully produced in *E. coli* and their calculated masses (~52 kD) corresponded to the expected sizes based on the amino acid sequence plus the 14 kD tag (data not shown). Although many different induction conditions were attempted, only the SAL1 (wild-type) fusion gene was successfully purified in the soluble fraction. This protein also showed similar PAP phosphatase enzymatic activity (16.6±SE 3.65 mmole $PAP.h^{-1}$.mg protein, n=3) to that previously reported (Xiong et al., 2001).

Western blot analysis was performed to determine the abundance of the SAL1 protein in wild-type and mutant plants. Authentic SAL1 recombinant protein was recovered after cleavage of the tag rendering a polypeptide of the expected molecular mass based on the amino acid sequence (37 kD) (FIG. 11A, lane 10). This protein was used to raise polyclonal antibodies, which were immunoaffinity purified against SAL1. A single 37 kD band, whose size corresponded to that of the recombinant protein, was detected in the total soluble protein extract of both wild-type plants but not in the mutants (FIG. 11A). Also, the SAL1 protein was not present in the total protein extract of alx8 but was in the wild-type Col-0 (FIG. 11B).

Alx8, Salk_020882 and Fry1-1 are Drought Tolerant

Figure 8A:
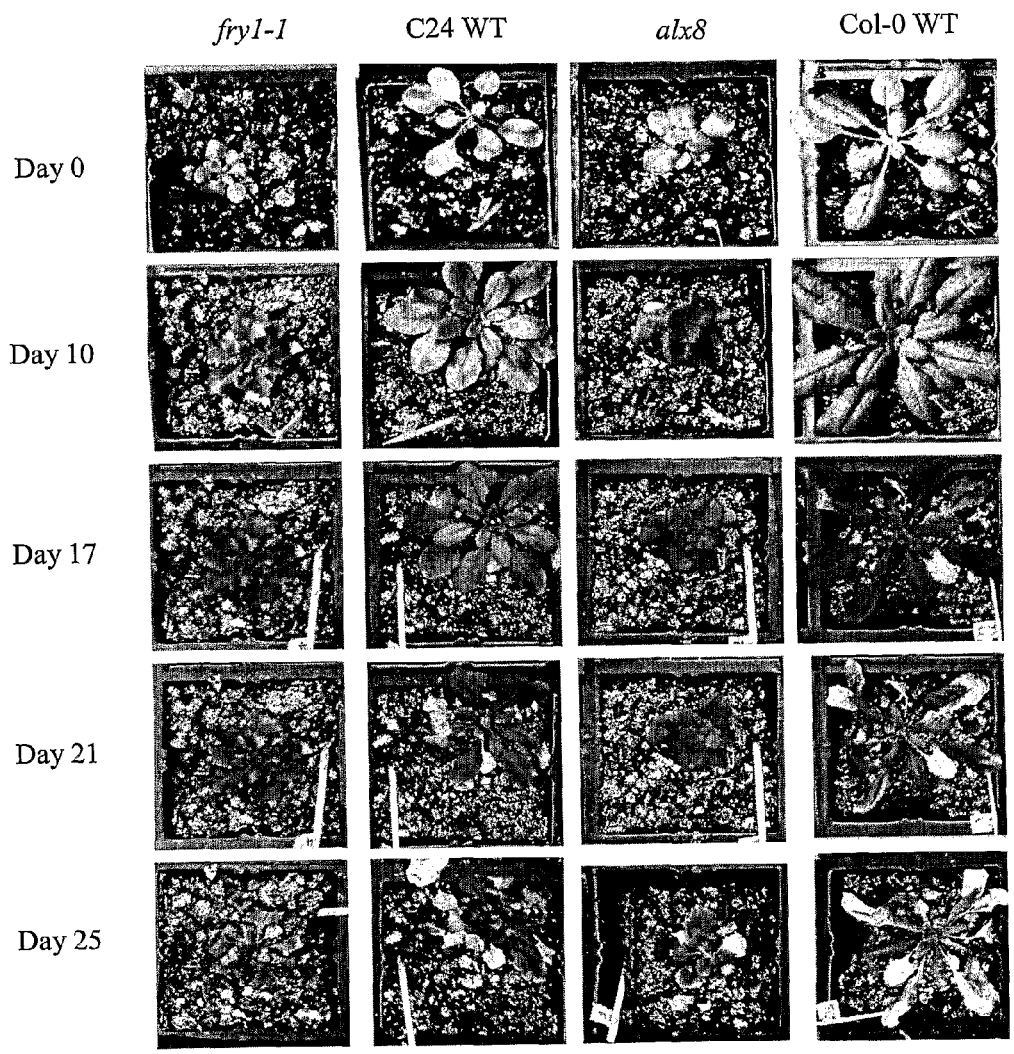

The fry1-1 mutant is a mutant *Arabidopsis thaliana* line that has increased expression of the stress response gene RD29A under normal conditions and also after cold, salt and osmotic stress and ABA treatment. This was found to be due to a point mutation resulting in a stop codon in the sixth exon of the SAL1 protein (At5g63980). This results in a truncated protein that does not contain a conserved α-helix containing a WD-$X_{11}$-GG motif required for coordination of metal ions and phosphate and also nucleophilic water activation. As a result the protein has no activity against $IP_3$ or PAP. The fry1-1 mutant was reported to have increased stress sensitivity to salt, cold and osmotic stress (Xiong, L. M. et al. (2001), *Genes & Development* 15(15): 1971-1984). This mutant also shows similar altered leaf morphology displayed by the alx8 and salk_020882 mutants. In the present studies, fry1-1 plants were found to be similarly drought tolerant as the alx8 and salk_020882 mutants compared to wild-type plants when subjected to a drought treatment at a similar developmental age (see FIG. 7) or chronological age (FIG. 8A). See also FIG. 15A. FIG. 8A shows that, whilst the Col-0 and C24 wild-type plants exhibit chlorotic and withered leaves after 21 days of water deprivation, the alx8 and fry1-1 plants only show signs of withering after 25 days, and FIG. 15A shows that the alx8, salk__020882 and fry1-1 plants do not show withering or chlorotic signs after 18 days, whereas the wild-type plants (Col-0 and Col-24 plants) showed withering and chlorosis after 18 days. As shown in FIG. 15A, which illustrates the results of water deprivation for 18 days, followed by re-hydration for 3 days, alx8, salk__020882 and fry1-1 plants recovered vigor within 3 days, whereas the Col-0 and C24 wild types show little, if any signs of recovery, most of the leaves being bleached and withered. This pattern was reproduced in more than 10 different experiments, with at least four plants per experiment.

Alx8, Salk__020882 and Fry1-1 and Drought Tolerance

Figure 8B:
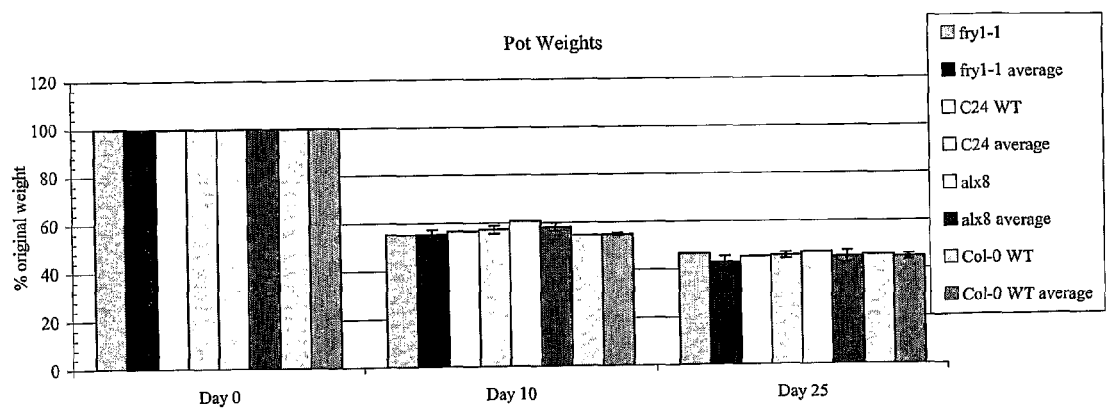

Despite both alx8 and fry1-1 being loss of function alleles (and the salk-020882 being presumed to be a loss of function allele), the seedling stage of fry1-1 has previously been described as being drought sensitive (Xiong et al, 2001), whereas soil grown mature alx8 plants are drought tolerant (Rossel et al, 2006), as are salk-020882 plants. The description of fry1-1 (by Xiong et al, 2001) is based on increased ion leakage from 1 week old seedlings to immersion in solution containing PEG. However no difference in the transpiration rates of detached shoots of fry1-1 and C24 wildtype was seen, indicating no change in stomatal control. To investigate the difference between fry1-1 and alx8 in this regard, the transpiration of detached rosettes of alx8, fry1-1, Col-0 wildtype and C24 wildtype was monitored by water loss. No significant difference was seen between the four types either in the initial phase or the secondary phase, indicating that water loss by transpiration and from the cuticle are similar.

fry1-1 mutants were then tested for soil based drought tolerance by withholding water from mature vegetative plants for 28 days. In multiple experiments fry1-1 was more drought tolerant than C24 wildtype (See, for example, FIGS. 7, 8A and 15A). To ensure both sets of plants were being exposed to the same stress, the relative water content of the soil was approximated by pot weight calculated as % of original pot weight. There was no significant difference in the water content of the soil between fry1-1 and C24 wildtype plants throughout the experiment (FIG. 8B). This was converted to soil water potential and again there was no significant difference between the soil water potential. Similarly, no significant difference in the soil water content of alx8 or salk-020882 plants and Col-0 wildtype plants has been seen in multiple experiments (FIGS. 8B, 15B and 21C). To ensure the tolerance of alx8 is not just a result of its developmental delay or smaller size, the drought tolerance of alx8 at a number of developmental stages was tested. alx8 was more drought tolerant than Col-0 wildtype at 2, 4, 6 and 8 weeks old. alx8 was also more drought tolerant than Col-0 wildtype when both plant types had six leaves; both were mature and vegetative; and when both were at the same developmental stage, just starting to bolt (FIG. 21). When the plants were just commencing to flower (FIG. 21A) the plants were of roughly the same rosette area and size, yet after 9 days of withholding water, alx8 and salk__020882 were both more turgid and green than the wild-type Col-0, although pots lost water at similar rates (FIG. 21C). Similarly, alx8 and fry1-1 plants grown to the same mature green stage of development, at which wild-type plants were 8 weeks old and alx8 plants 4 weeks old, were more drought tolerant (FIG. 21B). Water loss of detached rosettes was measured for the four genotypes to determine whether leaf and rosette shape alters the rate or water loss, or whether they differentially regulate water flux through stomatal control (the initial phase of water loss) or cuticular evapo-transpiration (the second phase of water loss). No significant difference was seen between the four lines in either phase (FIG. 21E). Thus, the changes in leaf morphology and rosette shape do not affect the rate of water loss from detached plants. Finally, drought tolerance was assessed for plants of the same age for which there was 1 Col-0 plant per pot compared to 2 alx8 plants per pot to equate for the difference in plant size and again alx8 was more tolerant than Col-0 to withholding of water. This indicates that it is not developmental delay of alx8 or a difference in the soil water content that results in the drought tolerance of alx8. Furthermore, transpiration from cut rosettes does not always correlate with drought tolerance of soil grown plants.

To quantify the extent of the drought tolerance of alx8 plants, a measure for plant viability using chlorophyll fluorescence was undertaken. The alx8 plants were shown to survive drought for 40-50% longer than Col-0 (data not shown).

In a different experiment, leaf relative water content (RWC) was measured under non-stressed conditions and after 12 days of drought (FIG. 16A). As expected the leaf RWC of alx8 did not change significantly during the drought while the leaf RWC of wild-type decreased significantly. Leaf water potential, or the chemical potential of water divided by the partial molar volume, was calculated for the same plants using a thermocouple psychrometer (FIG. 16B). The higher water potential of alx8 plants grown under drought conditions correlated with the maintained turgor while water-stressed wild-type plants had significantly lower leaf water potential.

Finally, water loss of detached rosettes was measured for the fry1-1 and alx8 mutants, and their respective wild-types (C24 and Col-0) to determine whether they differentially regulate water flux through stomatal control, the initial phase of water loss, or cuticular evapo-transpiration, the second phase of water loss. No significant difference was seen in either phase (data not shown).

SAL1 is a Highly Conserved Protein

The SAL1 protein is highly conserved through all living creatures. Hence homologues are present in all crop species for which substantial sequence information is available. It is expected that SAL1 and homologues thereof will be present in all plant species. This is indicated in the alignment in FIG. 5 of homologous proteins in plants that have been sequenced. Expressed Sequence Tags (ESTs) of other plant species were searched for the SAL1 mRNA and many homologous sequences were found (FIGS. 6A-6C).

There are also several homologous genes to SAL1 in the *Arabidopsis* genome.

Molecular Effects of the Alx8 Mutation

The expression of 13 stress response genes was measured in fry1-1 and alx8. Only a limited number of these genes had increased expression in the mutants under normal conditions: COR47 in fry1-1; and APX2, RAP2.6, ZAT10, ZAT12 and DREB2A in alx8. The expression of RD29A was increased in fry1-1 but not increased in alx8. The stress response genes HSP70, KIN1, CORM and ADH were not substantially upregulated under normal conditions in fry1-1 (Xiong et al, 2001). Similarly, sHSP, GST6 and APX1 were not substantially upregulated in alx8 under normal conditions. This is surprising give the constitutive higher levels of $IP_3$ in these mutants and indicates that $IP_3$ signalling may be involved in only some stress response pathways. To further investigate the upregulation of stress response pathways, as well as other non-stress related pathways, global expression was measured by microarrays.

Of the approximately 24,000 gene products quantified on the ATH1 GeneChip® (Affymetrix, Santa Clara, Calif., USA), 1414 genes were significantly upregulated more than 2-fold in alx8 leaf tissue relative to their expression in Col-0 wildtype. 1033 Genes were significantly downregulated more than 2-fold. In fry1-1 under normal growth conditions 1099 genes were significantly upregulated, and 745 downregulated, more than 2-fold relative to C24 wildtype. This bias towards upregulation fits with the proposed role of SAL1 as a negative regulator of signalling pathways. The overlap between expression changes in alx8 and fry1-1 was surprisingly limited—of the upregulated genes, only 727 were shared in common between the two mutants and, of the downregulated genes, only 395 were shared in common. These differences of regulation are not the same as the differences between the C24 and Col-0 wildtypes. Hence, this demonstrates the extent to which a similar mutation can cause different expression patterns in different ecotypes.

A number of stress response genes were upregulated in alx8, including those involved in both ABA-dependent pathways, for example:

upregulation of tonoplast aquaporin (TIP5;1) which is normally downregulated by sucrose, salt and $H_2O_2$, by ABA; and the negative regulator of flowering, CONSTANS-LIKE 9 (COL9), was highly upregulated in alx8. Overexpression of COL9 results in downregulation of CO and FTP and delayed flowering while a T-DNA knockout has early flowering (Xiao-Fei Cheng, Zeng-Yu Wang (2005), "Overexpression of COL9, a CONSTANS-LIKE gene, delays flowering by reducing expression of CO and FT in *Arabidopsis thaliana*" *The Plant Journal* 43 (5): 758-768). This result correlates with observations made throughout these studies which show that flowering in the SAL1 mutants studied is delayed by four to five weeks compared to wild-type plants. FIG. 15 shows alx8 and corresponding Col-0 wild-type plants at 2, 3, 5 and 8 weeks of age.

There was increased expression of APX2 (fold change=9.3, p-value=0.003); ZAT10 (fold change=5.00, p-value=0.028) and RAP2.6 (fold change=3.1, but large standard deviation) in alx8. Interestingly the expression of both COR47 and RD29A did not increase significantly in either alx8 or fry1-1. The lack of induction of RD29A was confirmed by real time RT-PCR. Hence it may be differences in growth or perturbations in the environment during experimental manipulations that result in the induction of these two genes in fry1-1. The absence of any change in the arrays for NCED3, GST6, APX1, RD29A and DREB2A in alx8 under well-watered conditions was also consistent with published results (Rossel et al., 2006).

A number of stress response genes were up-regulated in alx8 including transcription factors such as ZAT10, ZAT12, MYC2 and HB6. Other stress response genes up-regulated included: several early light inducible proteins, ELIPs; the aquaporin TIP5;1; stress signaling kinase SnRK2.2; stress inducible proteins, VSP1 and VSP2; and antioxidant enzymes CSD1 and CSD2.

To further investigate the type of pathways that are constitutively upregulated in alx8 genes whose expression was upregulated more than 25-fold were compared for their expression in other arrays stored in public databases using Genevestigator®. Despite the increased ABA content of alx8 there was no strong correlation between the expression patterns of alx8 with those in response to ABA. Only 10% of the genes were also upregulated by ABA, a similar number to those that are normally downregulated by ABA.

There was no strong correlation with any other hormone treatment either. There was some correlation between the expression patterns of alx8 and the response to abiotic stresses such as osmotic, wounding, heat, oxidative, cold and salt but it was not strong. Twelve percent of the up-regulated genes in alx8 were ABA-inducible, but a similar number were down-regulated by ABA. Similarly, there was no strong correlation with other hormone treatments, except for a slight correlation with jasmonic acid treatment.

Effect of SAL1 on Stomata

Previously, alx8 was shown to have lower stomatal conductance relative to Col-0 wildtype at range of different light intensities (Rossel et al, 2006). This decrease could be caused by a number of factors, including changes to the morphology, physiology and molecular profile of the plant.

The reduced conductance could be due to altered density, size and/or morphology of the alx8 stomata. Hence cryogenic scanning electron microscopy (SEM) was undertaken to look at the stomata. The stomata were normal in appearance, and were not clustered as seen in other mutants with stomata development mutations. Neither were the stomata located in a pit, which would decrease conductance by increasing resistance due to the boundary layer effect. Stomata of alx8 were also a similar size to those in Col-0 wildtype. Using SEM the stomatal density on the abaxial surface of leaves was calculated and found to be slightly higher in alx8 that on Col-0 wildtype plants. This is a much smaller increase compared to mutants such as stomatal density and distribution 1 (ssd1; AT1G04110), which has a 2.5-fold higher stomatal density on the abaxial side (Schlüter et al, 2003). Furthermore there was also an increase in number of epidermal cells resulting in a similar stomatal index in both alx8 and Col-0 wildtype. This was further confirmed by epidermal peels of stomata in alx8 and Col-0 wildtype plants grown in a different experiment. This time there was no significant difference in the stomatal density between Col-0 wildtype and alx8. Again the stomatal index was comparative between the two plant types. This emphasizes the importance of the stomatal index as a measure of stomatal number in comparing tissues of plants with altered development. Despite leaves being of a similar age they may differ in their stage of expansion, resulting in a higher cell density. If the number of stomata were a factor in the drought tolerance of alx8, it would be expected that alx8 would have a lower stomatal index than Col-0 wildtype. This is not the case and hence there may be an alteration in the function of the stomata.

Conductance can also be decreased by a reduction in stomatal aperture. Carbon-13 discrimination was used to see if there was a difference in the average stomatal aperture over the lifetime of the plant. When the stomata are open and gases are freely exchanged in and out of the stomatal pore the plant will preferentially fix $^{12}CO_2$ over $^{13}CO_2$ due to the discrimination by RUBISCO. However when the stomata are closed, the access to gases is limited and the plant is forced to use $^{13}CO_2$. Hence the ratio of $^{13}C$ to $^{12}C$ in the plant can be used to indicate the average stomatal conductance of the plant. Under normal growth conditions it was found that there was no difference in $^{13}CO_2$ discrimination between wildtype and alx8. This indicates that the average stomatal aperture is comparable between wildtype and alx8 under normal growth conditions. This was confirmed by measuring the aperture of stomata by epidermal leaf peels over a nine hour period. Again, no significant difference in aperture was seen between alx8 and Col-0 wildtype during the time course.

To see if there was any significant difference in stomatal aperture in response to drought $^{13}CO_2$ discrimination was performed on plants that had been under drought stress for 20 days. Only the tissues developed during the drought treatment were harvested. The $\delta^{13}C$ of drought affected plants was higher than control plants for both Col-0 wildtype and alx8, indicating that stomatal aperture had been reduced. The $\delta^{13}C$ of drought affected alx8 was not higher than that of drought affected Col-0 wildtype, indicating that alx8 does not have a smaller stomatal aperture during drought. Hence it seems that the decreased conductance observed for alx8 is due to factors other than stomatal aperture.

Leaf Morphology

It is well established that the morphological changes, such as succulence, increased leaf hairs can alter drought tolerance. The leaf morphology of alx8 is considerably altered to that of Col-0 wildtype plants. The leaves are shorter and rounder with more lobed edges. The surface of the leaf is often undulating and the petiole length reduced, giving the rosette a lettuce-like appearance. The SALK_020882 mutant shows similar leaf morphology (see, for example, FIG. 12) as does the fry1-1 mutant (see, for example, FIGS. 7 and 8A). Increased undulation of the leaf surface could increase the boundary layer effect, decreasing transpiration.

Leaf thickness was measured and found to be significantly greater in alx8 than Col-0 wildtype plants (FIGS. 18A and B). This thickness means that water vapour has a larger distance to travel to the stomatal opening and may inhibit water loss from the leaf. Increased leaf thickness also results in a decreased surface area to volume ratio, which could reduce water loss across the cuticle. Cross sections of the leaf examined by light microscopy also indicated a number of changes to the internal structure of the leaf including a disorganised vascular bundle, altered cell shape and smaller chloroplasts in alx8 (FIG. 18B). The cuticle is another possible source of water loss from leaves. However there is no visible difference in the cuticle thickness or structure in alx8 compared to Col-0 wildtype. Furthermore there is no significant change in regulation of cuticle synthesis genes such as WAX2 (At5g57800), CUT1/CER6 (At1g68530) and CER1 (At1g02205) in alx8 relative to Col-0 wildtype.

Although delayed in development and appearing smaller due to changes in leaf and rosette shape, alx8 plants had accumulated similar rosette fresh and dry mass as wild-type by eight weeks of growth (data not shown).

Cellular Morphology and Osmotic Potential

The chloroplasts of both Col-0 wildtype and alx8 were more closely examined by transmission electron microscopy and alx8 chloroplasts were found to lack starch granules. This inhibition in the accumulation of starch was further confirmed for alx8, as well as for fry1-1 by iodine staining (FIG. 19). Plants typically accumulate transitory starch in their leaves during the day and degrade it at night. As expected, wildtype leaves showed an increase of starch in the evening compared with morning. Likewise, alx8 and fry1-1 leaves had accumulated more starch in the evening than the morning. However, the amount present was substantially less than in wildtype plants under well watered conditions.

This decrease in starch correlates with an increase in expression of β-amylases, BMY1 and BMY8, in alx8. These enzymes hydrolyse transitory starch to maltose and β-limit dextrin, which may increase the intracellular osmotic potential of the plant cells. The metabolic profile of alx8, fry1-1 and their respective wildtypes under well-watered growth conditions was analysed by GC-MS.

All four lines had different profiles as indicated by principal components analysis (PCA), with a degree of overlap between C24 and Col-0 (FIG. 20). Both mutants were clearly separated from their respective wild-types by the first principal component (PC 1; accounting for 47.2% of total variance) representing the largest class separation observable by PCA. Interestingly, alx8 and fry1-1 were clearly separated by the second principal component (PC 2; accounting for 25.1% of total variance) while the two wild-types were not. In the SAL1 mutants there were significant increases in the levels of the polyamine, putrescine in alx8 and fry1-1 (Table 2). This correlated with an increase in expression of the rate limiting polyamine biosynthesis gene arginine carboxylase, ADC2 (6.43-fold) and a decrease in expression of the enzyme that converts spermidine to spermine, ACL5 (−3.90-fold). There was no significant difference in the proline abundance in alx8 relative to Col-0 despite an increase in the proline biosynthesis gene, pyrroline-5-carboxylate reductase (3.61-fold). In both alx8 and fry1-1 there were changes in abundance of a large number of sugars, including strongly decreased levels of fructose, galactose, glucose cellobiose and a large number of unknown sugars and sugar derivatives; and dramatic accumulation of a number of unknown sugars/sugar derivatives that were at undetectable or near-undetectable levels in wild-type plants (Table 2). Also striking were strong decreases in the organic acids citrate, isocitrate, fumarate and malate and strong increases in a number of metabolites of unknown class, some with spectral homology to indole-related compounds (Table 2).

TABLE 2

Characteristic metabolic profiles of SAL1 mutants

| | | alx8 vs Col-0 | | fry1-1 vs C24 | |
|---|---|---|---|---|---|
| Metabolite Class | Metabolite Name | Fold Difference | p-value | Fold Difference | p-value |
| Organic Acids | Citrate | <0.01 | <0.001 | 0.09 | 0.009 |
| | Fumarate | 0.03 | 0.003 | 0.08 | 0.001 |
| | Isocitrate | 0.05 | 0.014 | 0.03 | 0.004 |
| | Malate | 0.08 | <0.001 | 0.21 | 0.021 |
| Polyamines | Putrescine | 15.2 | 0.008 | 5.23 | 0.001 |
| Carbohydrates | [Unknown Disaccharide] RI = 2869 | 0.01 | <0.001 | 0.01 | <0.001 |
| | Glucose | 0.03 | <0.001 | 0.09 | <0.001 |
| | [Unknown Disaccharide] RI = 1946.9 | 0.04 | 0.001 | 0.11 | <0.001 |
| | [Unknown Sugar] RI = 2116.9 | 0.05 | <0.001 | 0.19 | 0.001 |
| | [Unknown Sugar] RI = 2122.6 | 0.05 | <0.001 | 0.16 | 0.001 |
| | Cellobiose | 0.06 | 0.047 | 0.06 | 0.007 |
| | Galactose | 0.11 | 0.001 | 0.09 | <0.001 |
| | Fructose | 0.16 | <0.001 | 0.29 | 0.002 |
| | [Unknown Disaccharide] | 0.16 | 0.044 | 0.3 | 0.035 |

TABLE 2-continued

Characteristic metabolic profiles of SAL1 mutants

| Metabolite Class | Metabolite Name | alx8 vs Col-0 Fold Difference | p-value | fry1-1 vs C24 Fold Difference | p-value |
|---|---|---|---|---|---|
| | [Unknown Monosaccharide] RI = 2730.9 | 0.32 | 0.002 | 0.14 | 0.001 |
| | [Unknown Similar to Galactinol] RI = 1777.7 RI = 2963 | 0.41 | 0.007 | 0.07 | 0.003 |
| | [Unknown Sugar] RI = 2094.1 | 0.45 | 0.012 | 0.66 | 0.041 |
| | [Unknown Putative Disaccharide] RI = 2836.1 | 0.45 | 0.009 | 0.22 | <0.001 |
| | [Unknown Disaccharide] RI = 2534.4 | 5.63 | <0.001 | 5.97 | 0.001 |
| | [Unknown Disaccharide] RI = 2544.4 | 13.92 | <0.001 | 5.39 | 0.002 |
| | [Unknown Putative Disaccharide] RI = 2808.4 | 50.86 | <0.001 | 22.62 | 0.002 |
| | [Unknown Putative Disaccharide] RI = 2923.4 | 75.11 | 0.001 | 26.13 | 0.018 |
| | [Unknown Putative Disaccharide] RI = 2898.4 | 155.75 | <0.001 | 227.13 | 0.001 |
| | [Unknown Sugar] RI = 2149.9 | 168.5 | <0.001 | 60.67 | 0.001 |
| | [Unknown Probable Disaccharide] RI = 2748.9 | 313.1 | <0.001 | 136.59 | <0.001 |
| | [Unknown Putative Disaccharide] RI = 2997.5 | 2767.48 | <0.001 | 5684.57 | <0.001 |
| | [Unknown Putative Disaccharide] RI = 2915.4 | 4624.26 | <0.001 | 456.97 | 0.001 |
| Unknown Class | [Unknown] RI = 2656.2 | 13.33 | <0.001 | 34.94 | 0.026 |
| | [Unknown] RI = 3116.0 | 778.55 | <0.001 | 92.18 | <0.001 |
| | [Unknown] RI = 2656.2 | 1027.05 | <0.001 | 1100.47 | 0.006 |
| | [Unknown Possibly Indole Related] RI = 1404.6 | 99.82 | 0.002 | 26.54 | 0.005 |
| | [Unknown Related to Tryptamine] RI = 1505.1 | 16.38 | 0.003 | 32.48 | 0.001 |
| | [Unknown Possibly Indole Related] RI = 1389.1 | 200.04 | <0.001 | 104.69 | 0.002 |

Fold differences and p-values (n = 5) are shown for the major (most intense) metabolite differences that were common to both alx8 and fry1-1.
Unknown metabolites (enclosed in square brackets) were annotated based on the similarity of their mass spectra to reference spectra in the NIST05 mass spectral library.
Retention indices are given for unknown metabolites.
RI = "Retention Index".

Discussion

Drought tolerance of alx8 mutants appears to be due to a reduction in transpiration under stress conditions, resulting in higher relative water contents in leaves and soil. However, the reduction in transpiration does not seem to be due to an increase in drought induced stomatal closure. Both carbon discrimination and cut rosette dehydration experiments indicated less stomatal closure in alx8 compared to that in Col-0 wildtype under drought conditions. Hence the reduction of water loss is due to other morphological, physiological or molecular changes in alx8 or a combination thereof.

Changes to the structural morphology of alx8 could cause a reduction in the loss of water under drought stress. Increased leaf thickness and a disorganised vascular bundle may slow the movement of water through the plant and the diffusion of water vapour through the sub-stomatal chambers. Similarly, there may be changes in the root morphology of alx8 that alter water uptake and translocation under water stress conditions.

Despite a lack of induction of known stress response genes there are still a number of changes in the metabolic profile of alx8 that are related to stress responses, including an increase in polyamines, trehalose, sugars and glycerol.

The accumulation of osmoprotectants in alx8 and fry1-1 is likely to be a contributing factor to their drought tolerance. The level of the polyamine, putrescine, was 15.2-fold (p-value=0.008) higher in alx8 than in its respective wild-type, Col-0. Correspondingly, alx8 has higher expression of the polyamine biosynthetic enzyme ADC2, which is normally up-regulated in response to osmotic stress (Perez-Amador, M. A., et al (2002, *Plant Physiology*, 130, 1454-1463). Constitutively high putrescine levels have been reported in a drought tolerant wheat variety and in oxidative stress tolerant variety of the weed, *Conyza bonariensis* (Ye et al., (1997), *Plant Physiology*, 15, 1443-1451). Increased polyamine levels by over-expression of biosynthetic enzymes has previously been shown to induce tolerance to a range of abiotic stresses, including drought (Kurepa et al., (1998), *Plant Cell Physiology*, 39, 987-992; Kasukabe et al., (2004), *Plant and Cell Physiology*, 45, 712-722). Although the exact role of putrescine in tolerance remains uncertain, potential roles have been reported as a direct or indirect anti-oxidant defense (Ye et al., 1997) and as a regulator of spermine and spermidine synthesis during drought that provide an antisenescence effect at the whole-plant level, resulting in phenotypically normal plants (Capell et al., (2004), *Proceedings of the National Academy of Science USA*, 101, 9909-9914).

Levels of a number of sugars are also altered in alx8 leaf tissue, including large increases in a number of unidentified sugars (Table 2). These changes inversely correlated with decreased accumulation of transitory starch in the chloroplasts of alx8 (FIG. 19). Sugars may play an important role in the osmotic stress response as osmoprotectants, protecting macromolecules and preventing membrane fusion (Bartels and Sunkar, (2005), *Critical Reviews in Plant Sciences*, 24, 23-58). Hence, the altered sugar composition in alx8 leaf tissue may be involved in its drought tolerance.

The pre-acclimation to drought conditions and altered development of alx8 does not affect the water balance of the plant under watered conditions. However it may explain the temporarily delayed growth of alx8 as resources are allocated to stress tolerance mechanisms and not into growth. This effect is temporary as by the later stages of development the dry weights of the rosettes of alx8 and fry1-1 are similar to their respective wild-types.

The differences observed in metabolites for the alx8 and fry1-1 mutants are already present under normal growth conditions, indicating a pre-acclimation to drought. This pre-acclimation of the mutants does not affect the water balance of the plants under well watered conditions. No difference in leaf water potential or relative water content was seen. Similar stomatal apertures were also present between alx8 and the Col-0 wildtype under these conditions, as shown by carbon discrimination and epidermal leaf peels.

As the photosynthetic rate is similar between alx8 and the Col-0 wildtype under these conditions, the delayed development of alx8 is probably due to the re-assignment of resources and activation of growth suppressive pathways rather than a lack of resources. Loss-of-function mutations in SAL1 resulted in up-regulation of >1000 genes and down-regulation of 500-1000 genes under non-stressed growth conditions compared to wild-type plants. The role of SAL1 as a regulator of gene expression in both stress and development is reinforced by its negative role in post-transcriptional gene silencing (Gy et al., (2007), *Plant Cell*, tpc.107.055319) and the altered morphology and flowering time of SAL1 mutants. In fact, just 7.6% of the 2447 genes differentially regulated in alx8 are classified as stress response genes (data not shown) and most of these are not inducible by ABA. This suggests that not all stress response pathways are constitutively activated in alx8 under non-stressed growth conditions. For example, APX2, RAP2.6, sHSP and DREB2A are induced between 2- and 20-fold in non-stressed leaves, but high light stress (HL) results in 25- to 700-fold induction of the same genes, demonstrating other pathways that regulate these genes are stress-inducible (Rossel et al., 2006). Secondly, the expression of dehydration-responsive RD22 is up-regulated by ABA (Yamaguchi-Shinozaki et al., (1992), *Plant and Cell Physiology*, 33, 217-224) and this induction is partially dependent on the transcription factor MYC2, which when over-expressed results in constitutive induction of RD22 (Abe et al., (1997), *Plant Cell*, 9, 1859-1868; Abe et al., (2003), *Plant Cell*, 15, 63-78). However in alx8 despite a 8.2-fold increase in MYC2 expression, the expression of RD22 is down-regulated −3.7-fold. Likewise, there is no significant induction of ADH1 or KIN2/COR6.6, which have been shown to be ABA-responsive and MYC2-regulated (Abe et al., 2003). This indicates a need for the interaction of multiple pathways in addition to the ABA-independent pathways constitutively activated in alx8 and fry1 for full activation of the stress response.

Of the known stress responsive transcription factors, a small subset are significantly up-regulated in alx8 under non-stressed conditions, including two zinc finger transcription factors, ZAT10 and ZAT12. Both ZAT10 and ZAT12 are involved in the abiotic stress response pathways such as drought and high light (Sakamoto et al., (2004), *Plant Physiology*, 136, 2734-2746; Davletova et al., (2005), *Plant Physiology*, 139, 847-856; Rossel et al., (2007), *The Plant Cell*, 10.1105/tpc.1106.045898). Overexpression of ZAT10 induces expression of APX2 and 18% of the genes up-regulated in HL (Rossel et al., 2007). Correspondingly, 24.6% of the genes up-regulated by HL are also up-regulated in alx8 further emphasizing the overlap between drought and HL stress response networks. High levels of expression of SAL1 in the vascular tissue (Xiong et al., 2001), suggests a role in the transduction of signals during drought stress. This localization correlates with increased $H_2O_2$ production and antioxidant enzyme expression in the bundle sheath seen in response to other abiotic stresses, such as HL (Karpinski et al., (1999), *Science*, 284, 654-657; Rossel et al., 2007). Furthermore, APX2 and ZAT10 expression is largely localized to the vasculature, which may indicate a role for SAL1 in the control of similar ROS-mediated responses.

Drought induces an increase in ABA and typically there is a corresponding increase in expression of rate limiting ABA biosynthetic enzymes, NCED3 and NCED1 (Iuchi et al., (2001), *Plant Journal*, 27, 325-333). However these genes are not up-regulated in alx8 nor is there down-regulation of genes involved in ABA catabolism, in fact the catabolic enzyme CYP707A1-4 is up-regulated (data not shown). Hence, the increase of ABA content in alx8 (Rossel et al. 2006) does not appear to be transcriptionally regulated.

The majority of the up-regulated (66%) and down-regulated (53%) genes in fry1-1 were co-expressed in alx8 compared to wild-type. However, there were differences in gene expression and metabolic profile between alx8 and fry1-1, which is interesting given they are both loss-of-function mutations in the same gene. C24 and Col-0 had unique, although similar metabolite profiles and thus it is possible that ecotype differences subtly alter the role of SAL1 and the effects of its loss in each ecotype.

An additional interesting observation during these studies is that the SAL1 mutants studied had delayed flowering times relative to wild-type plants, and that this correlated with strong upregulation of the negative regulator of flowering, CONSTANS-LIKE 9 (COL9). This may have application in many aspects of agriculture, including delaying flowering (and therefore, typically, senescence) in pasture plants, producing plants with extended growth periods which may allow for greater yields or larger parts (such as flowers, stems, leaves, tubers, etc.). Increasing the expression of SAL1 in plants may have a converse effect.

CONCLUSION

SAL1 mutants survive a prolonged drought 40-50% longer than wild-type plants and whilst development is altered, the leaf and stem biomass in fully mature plants is unchanged. Without wishing to be bound by theory, we hypothesize that the SAL1 protein has a role in the negative regulation of pathways controlling morphological, physiological and molecular changes whose activation results in enhanced induction of stress networks. The result is enhanced tolerance to drought rather than an avoidance response. This is indicated by a degree of pre-acclimation, such as the constitutive up-regulation of stress response genes such as the antioxidant APX2, accumulation of osmoprotectants such as polyamines and sugars, and accumulation of abscisic acid under non-stressed conditions. Thus, SAL1 appears to negatively regulate drought tolerance and as a consequence, mutants maintain full turgor and water potential under water stress.

It will be appreciated that, although specific embodiments of the invention have been described herein for the purpose of illustration, various modifications may be made without deviating from the spirit and scope of the invention as defined in the following claims.

The invention claimed is:

1. A method for obtaining a plant with increased drought resistance relative to a wild-type plant, comprising:
   (a) introducing at least one mutation or exogenous nucleic acid into the genome of one or more plant cells which results in reduced activity associated with SAL1 or a homologue thereof in said one or more plant cells, wherein said homologue has inositol polyphosphate 1-phosphatase activity and 3'(2'),5'-bisphosphate nucleotidase activity;
   (b) regenerating one or more plants from said one or more plant cells; and
   (c) selecting one or more plants that have increased drought resistance relative to a wild-type plant,
   with the proviso that said mutation is not selected from the following:
   a mutation in SEQ ID NO:1 resulting in a stop codon instead of a codon encoding a tryptophan residue at position 341 in SEQ ID NO:2;
   a guanine to adenine mutation at position 736 of SEQ ID NO:1;
   a mutation in SEQ ID NO:1 resulting in a glutamic acid to lysine substitution at position 126 of SEQ ID NO:2;
   a 6.7 kb T-DNA insertion between the fifth and sixth exons at position 1518 of SEQ ID NO:1;
   a T-DNA insertion between positions 734 and 735 of SEQ ID NO:1;
   a T-DNA insertion replacing nucleotides 735-745 of SEQ ID NO:1;
   a cytosine to thymine mutation at position 731 of SEQ ID NO:1;
   a mutation in SEQ ID NO:1 resulting in an alanine to valine substitution at position 124 of SEQ ID NO:2;
   a guanine to adenine mutation oat position 1226 of SEQ ID NO:1; and
   a mutation in SEQ ID NO:1 resulting in a glycine to aspartic acid substitution at posision 217 of SEQ ID NO: 2.

2. The method of claim 1, wherein said at least one mutation is introduced by exposing said one or more plant cells to chemical or physical mutagenic means or insertional mutation means such as transposons or T-DNA.

3. The method of claim 1, comprising introducing a mutation into a nucleotide sequence encoding SAL1 or a homologue thereof in said one Or more plant cells.

4. The method of claim 3, wherein said mutation comprises an insertion, deletion or substitution of one or more nucleotides.

5. The method of claim 3, wherein said mutation is a SAL1 null mutation.

6. The method of claim 1 wherein said plant is selected from the Apiaceae, Asteraceae, Brassicaceae, Chenopodiaceae/Amaranthaceae, Compositae, Cucurbitaceae, Fabaceae, Gramineae, Leguminosae, Poaceae, Rosaceae or Solanaceae.

7. The method of claim 6, wherein said plant is a member of the Brassicaceae family.

8. A plant with increased drought resistance relative to a wild-type plant, obtained by the method of claim 1.

9. The plant of claim 8, wherein said plant is selected from the Apiaceae, Asteraceae, Brassicaceae, Chenopodiaceae/Amaranthaceae, Compositae, Cucurbitaceae, Fabaceae, Gramineae, Leguminosae, Poaceae, Rosaceae or Solanaceae.

10. The plant of claim 9, wherein said plant is a member of the Brassicaceae family.

\* \* \* \* \*